(12) United States Patent
Evseenko

(10) Patent No.: US 11,420,964 B2
(45) Date of Patent: Aug. 23, 2022

(54) COMPOSITIONS AND METHODS FOR MODULATING INFLAMMATORY AND DEGENERATIVE DISORDER

(71) Applicant: University of Southern California, Los Angeles, CA (US)

(72) Inventor: Denis Evseenko, Tarzana, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/519,016

(22) Filed: Nov. 4, 2021

(65) Prior Publication Data

US 2022/0048901 A1 Feb. 17, 2022

Related U.S. Application Data

(63) Continuation of application No. 16/898,236, filed on Jun. 10, 2020, now abandoned, which is a continuation of application No. PCT/US2019/020058, filed on Feb. 28, 2019.

(60) Provisional application No. 62/636,325, filed on Feb. 28, 2018.

(51) Int. Cl.
| | |
|---|---|
| *C07D 417/12* | (2006.01) |
| *A61P 19/02* | (2006.01) |
| *A61K 31/4439* | (2006.01) |
| *A61K 9/00* | (2006.01) |
| *A61K 9/16* | (2006.01) |
| *A61K 31/444* | (2006.01) |
| *A61K 45/06* | (2006.01) |
| *C07D 401/12* | (2006.01) |

(52) U.S. Cl.
CPC .......... *C07D 417/12* (2013.01); *A61K 9/0019* (2013.01); *A61K 9/16* (2013.01); *A61K 31/444* (2013.01); *A61K 31/4439* (2013.01); *A61K 45/06* (2013.01); *A61P 19/02* (2018.01); *C07D 401/12* (2013.01)

(58) Field of Classification Search
CPC .. C07D 417/12; C07D 401/12; C07D 213/81; C07D 277/42; C07D 413/12; C07D 417/14; A61K 9/0019; A61K 9/16; A61K 31/4439; A61K 31/444; A61K 45/06; A61K 9/5031; A61K 31/506; A61K 31/427; A61P 19/02; A61P 35/00
See application file for complete search history.

(56) References Cited

U.S. PATENT DOCUMENTS

| | | |
|---|---|---|
| 2004/0077875 A1 | 4/2004 | Das et al. |
| 2006/0199960 A1 | 9/2006 | Jaeschke et al. |
| 2009/0048313 A1 | 2/2009 | Dickson et al. |
| 2010/0029709 A1 | 2/2010 | Menet et al. |
| 2014/0170165 A1 | 6/2014 | Lu et al. |

FOREIGN PATENT DOCUMENTS

| | | |
|---|---|---|
| EP | 0001727 A2 | 5/1979 |
| EP | 2682390 A1 | 1/2014 |
| WO | 2005/079802 A1 | 9/2005 |
| WO | 2013082324 A1 | 6/2013 |
| WO | 2016/138533 A2 | 9/2016 |

OTHER PUBLICATIONS

Kobayashi, Miki, International Preliminary Report on Patentability and Written Opinion, PCT/US2019/020058, The International Bureau of WIPO, dated Sep. 10, 2020.
Mohammad et al., Chapter 2—General Principles of Suspensions, Pharmaceutical Suspensions, pp. 39-65, First Online: Oct. 8, 2009.
Safdar et al., "New developments and clinical transition of hyaluronic acid-based nanotherapeutics for treatment of cancer: reversing multidrug resistance, tumour-specific targetability and improved anticancer efficacy," Artificial Cells, Nanomedicine, and Biotechnology, 46(8):1967-1980, 2017.
Thomas, Shane, International Search Report & Written Opinion of the International Searching Authority, PCT/US2019/020058, United States Patent & Trademark Office, dated Jun. 17, 2019.
Cielen, Elsie, Supplementary European Search Report, Application No. 19760273.3, European Patent Office, dated Oct. 18, 2021.
Shkhyan, Ruzanna et al., "Drug-induced modulation of gp 130 signalling prevents articular cartilage degeneration and promotes repair," Annals of the Rheumatic Diseases, vol. 77, No. 5, Feb. 7, 2018, pp. 760-769.

*Primary Examiner* — Sarah Pihonak
*Assistant Examiner* — Jason Deck
(74) *Attorney, Agent, or Firm* — Gavrilovich, Dodd & Lindsey LLP

(57) ABSTRACT

The disclosure provides compounds and method useful for modulating gp130 biological activity. The disclosure also provides methods and compositions for treating disease and disorders associated with gp130 activity, particularly those associated with inflammation.

7 Claims, 29 Drawing Sheets

Specification includes a Sequence Listing.

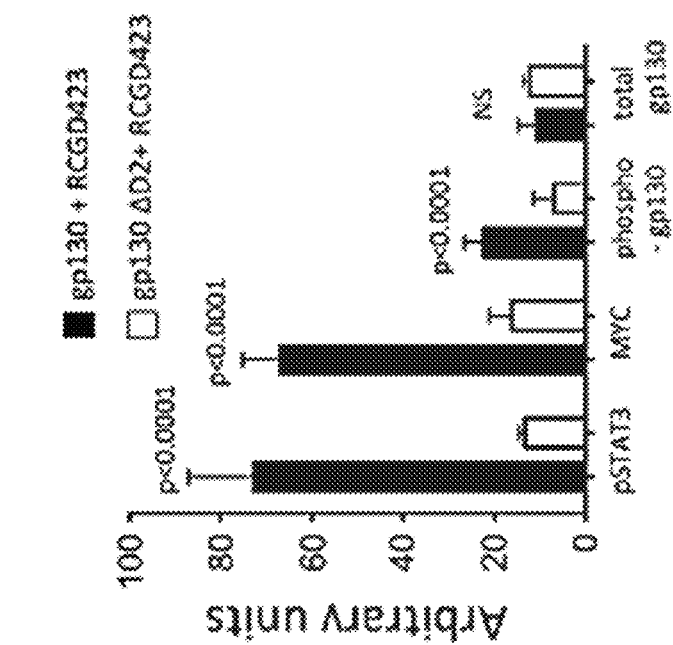
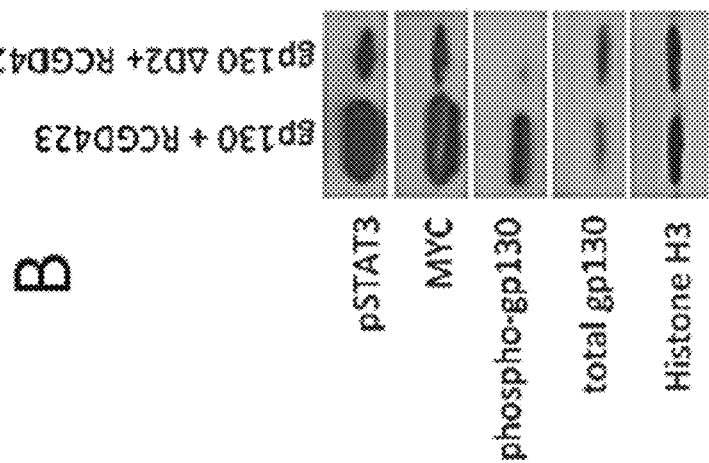
FIG. 7B
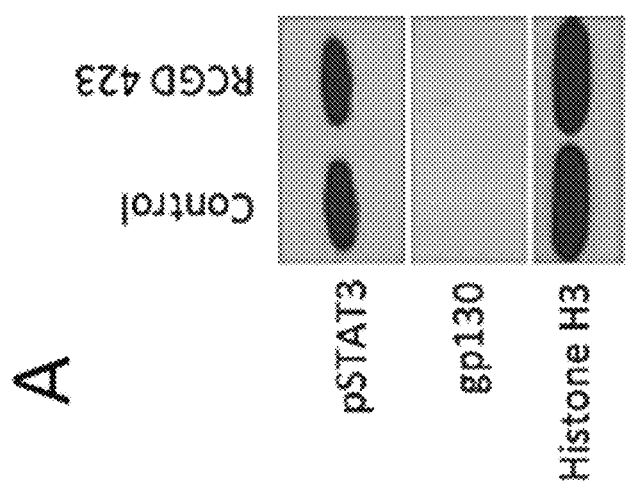
FIG. 7A

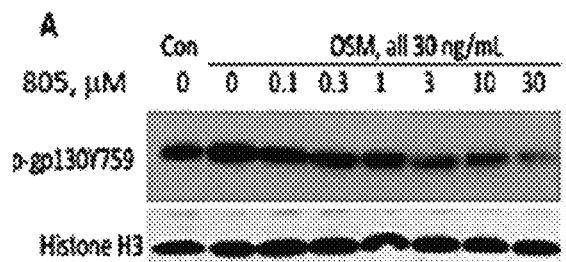
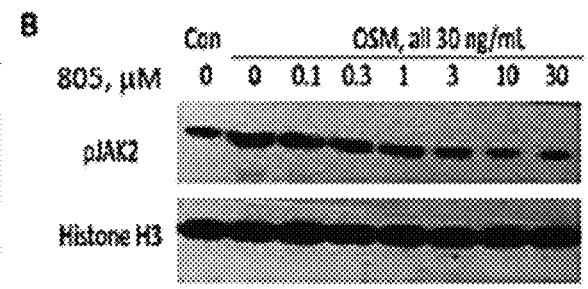
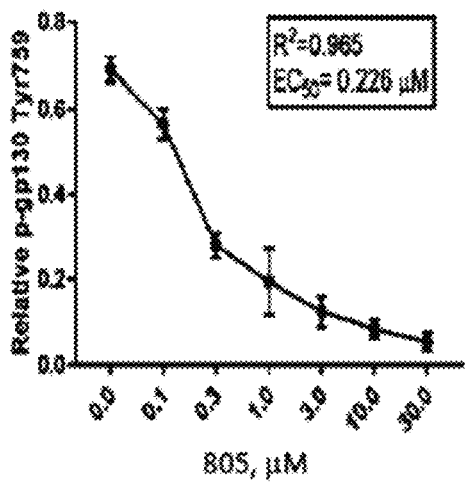
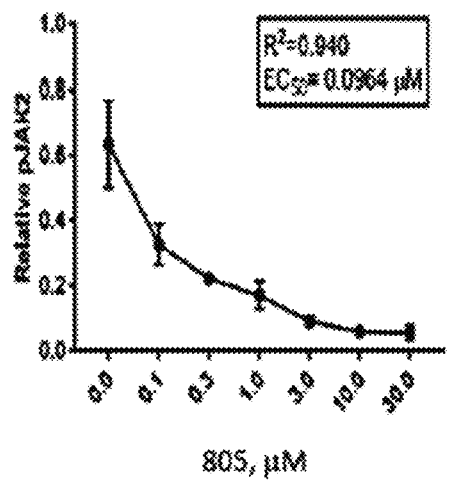
FIG. 25A    FIG. 25B
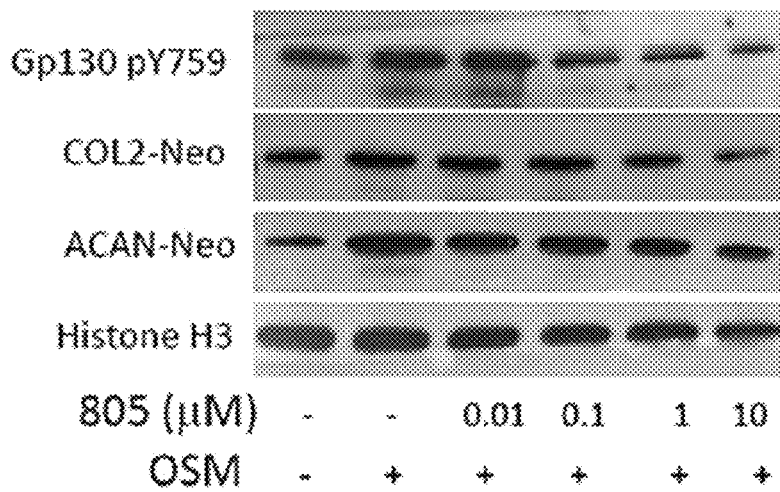
FIG. 26

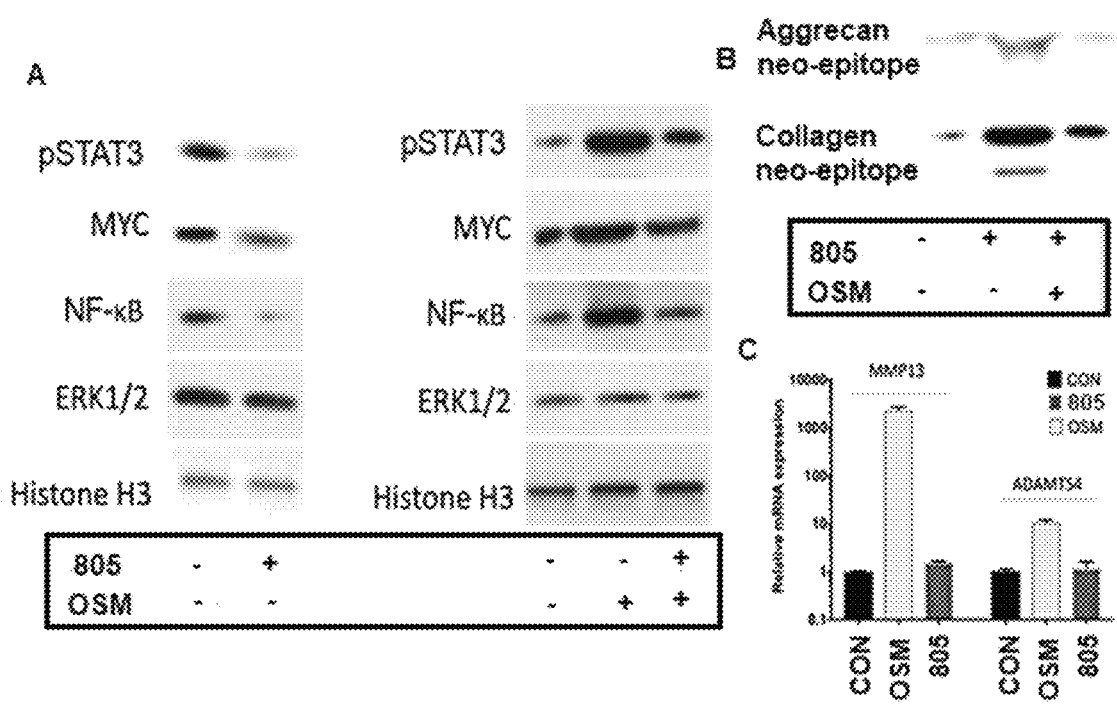
FIG. 27A        FIG. 27B-C

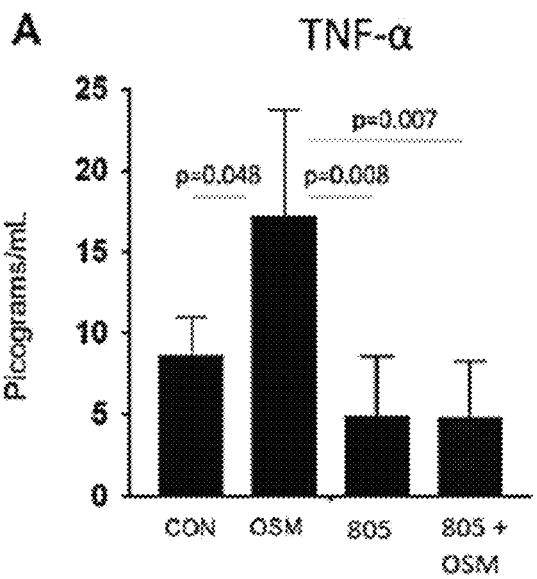
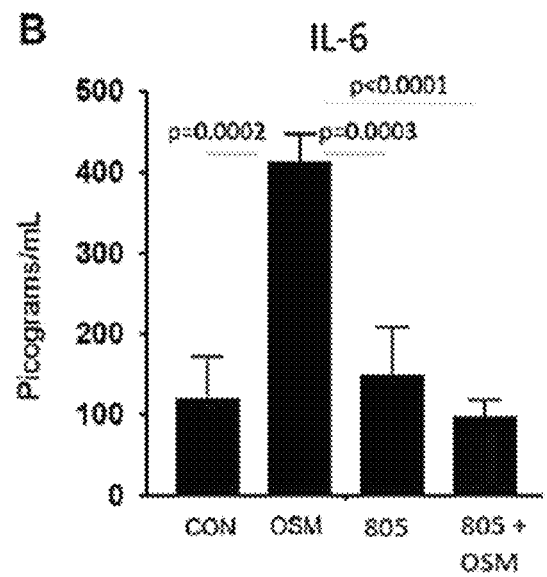
FIG. 33A
FIG. 33B
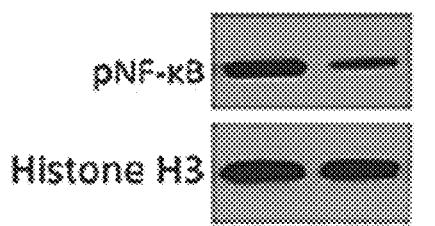
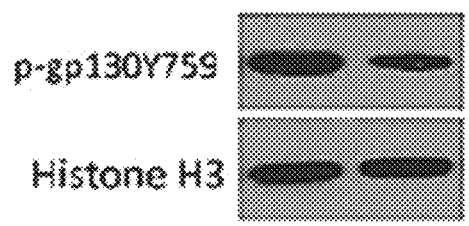
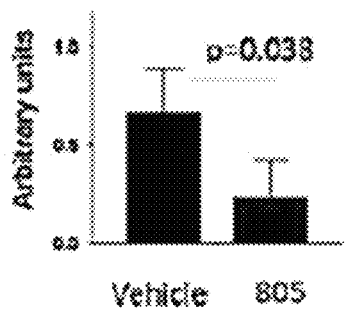
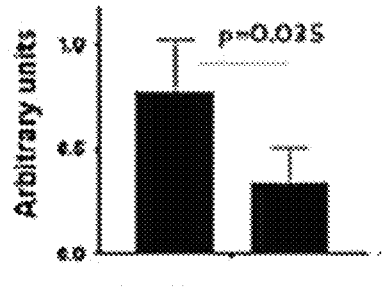
FIG. 34

```
                          SEQUENCE LISTING

<160> NUMBER OF SEQ ID NOS: 4

<210> SEQ ID NO 1
<211> LENGTH: 918
<212> TYPE: PRT
<213> ORGANISM: Homo sapiens

<400> SEQUENCE: 1

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335
```

```
Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750
```

-continued

```
Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 2
<211> LENGTH: 8
<212> TYPE: PRT
<213> ORGANISM: Homo sapiens

<400> SEQUENCE: 2

Glu Thr His Leu Glu Thr Asn Phe
1               5

<210> SEQ ID NO 3
<211> LENGTH: 7
<212> TYPE: PRT
<213> ORGANISM: Homo sapiens

<400> SEQUENCE: 3

Lys Ala Lys Arg Asp Thr Pro
1               5

<210> SEQ ID NO 4
<211> LENGTH: 4
<212> TYPE: PRT
<213> ORGANISM: Homo sapiens

<400> SEQUENCE: 4

Lys Ala Lys Arg
1
```

COMPOSITIONS AND METHODS FOR MODULATING INFLAMMATORY AND DEGENERATIVE DISORDER

CROSS REFERENCE TO RELATED APPLICATIONS

This application is a continuation of U.S. application Ser. No. 16/898,236, filed Jun. 10, 2020, which application is a continuation of International Application Serial No. PCT/US2019/020058, filed Feb. 28, 2019, which application claims priority under 35 U.S.C. § 119 from Provisional Application Ser. No. 62/636,325, filed Feb. 28, 2018, the disclosures of which are incorporated herein by reference.

TECHNICAL FIELD

The disclosure provides compounds and method useful for modulating gp130 biological activity. The disclosure also provides methods and compositions for treating disease and disorders associated with gp130 activity, particularly those associated with inflammation.

BACKGROUND

Osteoarthritis (OA) is a degenerative disease of joints, characterized by progressive loss of cartilage which causes stiffness, swelling and pain. Nearly 10% of the world's population suffers from OA, making it the most common form of arthritis and one of the most common pathological conditions. In the United States, there are over 27 million people affected by OA, with this number projected to climb steeply due to a rapidly aging population and increases in obesity rates. Each year, over $185 billion is spent to treat OA globally, establishing this disease as a major burden on global health and economics.

Currently, there are no disease modifying agents available on the market for the treatment of osteoarthritis. Treatment modalities are focused on lifestyle modifications, pain management and improving joint viscosity, with the overall goal to delay joint replacement surgery. Initial therapies for those with mild osteoarthritis include weight loss, physical therapy and pain management using over-the-counter non-steroidal anti-inflammatory drugs (NSAIDs). As the condition progresses to a moderate stage, opioid-based pain control is introduced, while continuing physical therapy and other exercises. If the disease progresses to a severe stage, intra-articular injections, such as hyaluronic acid, are used to increase joint viscosity. Finally, if none of the previous treatments are able to mitigate pain, total joint replacement surgery is considered. There are over 1 million knee and hip replacements performed each year in the U.S, at a cost of over $50 billion.

These glaring statistics, and the lack of effective treatments that address the causes rather than the symptoms of OA, have not escaped notice by clinicians and researchers. The most effective treatments for cartilage lesions thus far include four main surgical procedures: microfracture, osteochondral autologous transplantation (OATS), autologous chondrocyte implantation (ACI) and fresh osteochondral allograft (FOA). Each of these procedures has major disadvantages that preclude widespread adoption and implementation. Microfracture is technically easy, but is prone to subsequent degeneration in comparison to the other methods, and mostly results in the formation of biomechanically inferior fibrocartilage. OATS is technically difficult, and donor site morbidity increases with the number and size of the osteochondral plugs that are removed for transplantation. ACI is by far the most expensive cartilage defect treatment, and recovery biopsies still display fibrocartilaginous content in place of hyaline cartilage. FOA is also expensive due to specific instrumentation required for the procedure, limited availability of tissue and short shelf-life of material for transplantation (less than 6 weeks). Critically, all of these techniques require surgery in order to be implemented; this fact, in combination with the unconvincing data surrounding their efficacy, has limited the broad implementation of these therapies.

Newer efforts in cell therapy are focusing on transplantation of chondrocytes from other sources or mesenchymal stem cells into the joint. Many groups are optimizing strategies to generate articular-like chondrocytes from pluripotent stem cells for use in cartilage repair. This approach, although promising, will face many of the same hurdles that impede the adoption of existing cell therapies: integration of transplanted cells with existing cartilage, inflammation and graft survival. Other groups are pursuing a strategy similar to microfracture, in that they are attempting to promote the adoption of an articular cartilage fate by mesenchymal stem cells isolated from a variety of sources. Because the starting material for these procedures can be expanded in culture and applied allogeneically, several groups have reached Phase 2 clinical trials with their work in this area. However, as with microfracture, concerns over the ability of the cells to generate true articular cartilage (vs. fibrocartilage) that substantially integrates with surrounding tissue loom.

SUMMARY

The disclosure provides a compound comprising the structure of Formula I, II or III:

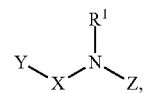

Formula I

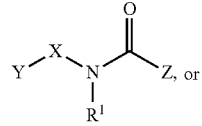

Formula II

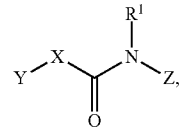

Formula III wherein,
X is:

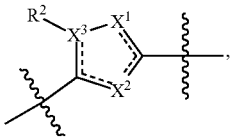

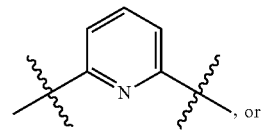

, or

Y is:

, or

;

Z is:

;

X¹ is S, CH, or NH;
X² is S, CH, or N;
X³ is CR² or S;
Y¹ is CR⁷ or N;
Y² is CR⁶ or N;
Y³ is CR⁵ or N;
Z¹ is O or CH;
Z² is O, N, NH or CH;
Z³ is CR⁹ or N;
Z⁴ is CR⁸ or N;
Z⁵ is N or CR¹⁴;
Z⁶ is N or CR¹³;
Z⁷ is N or CR¹²;
Z⁸ is N or CR¹¹;
Z⁹ is N or CR¹⁰;
v is 0 or 1;
$R^1$, $R^2$, $R^8$ and $R^9$ are independently selected from H, D, ($C_1$-$C_3$) alkyl, ($C_1$-$C_3$)alkenyl, halo, cyano, hydroxyl, nitro, thiol, and amino;
$R^3$-$R^7$ and $R^{10}$-$R^{14}$ are independently selected from H, D, ($C_1$-$C_3$) alkyl, ($C_1$-$C_3$) alkenyl, halo, cyano, hydroxyl, nitro, thiol, amino, OC($R^{15}$)$_3$, OCH($R^{15}$)$_2$, OCH2($R^{15}$), wherein n is an integer from 1 to 5; and
$R^{15}$ is independently H, halo, or a ($C_1$-$C_3$) alkyl;
  and wherein the compound interacts with domain 2 of gp130 and which locks gp130 into a non-permissive conformation and/or produce atypical gp130 homodimers. In one embodiment, X is selected from the group consisting of , , , , and

;

and wherein $R^2$ is an H, D, ($C^1$-$C_3$)alkyl, ($C_1$-$C_3$) alkenyl, halo, cyano, hydroxyl, nitro, thiol, or amino. In another or further embodiment, Y is selected from the group consisting of:

, , , , and ;

and wherein v is 0 or 1; $R^3$-$R^7$ are independently selected from H, D, ($C_1$-$C_3$)alkyl, ($C_1$-$C_3$)alkenyl, halo, cyano, hydroxyl, nitro, thiol, amino, OC($R^{15}$)$_3$, OCH($R^{15}$)$_2$, OCH2($R^{15}$), and wherein n is an integer from 1 to 5. In still another of further embodiment of any of the foregoing, Z is selected from the group consisting of:

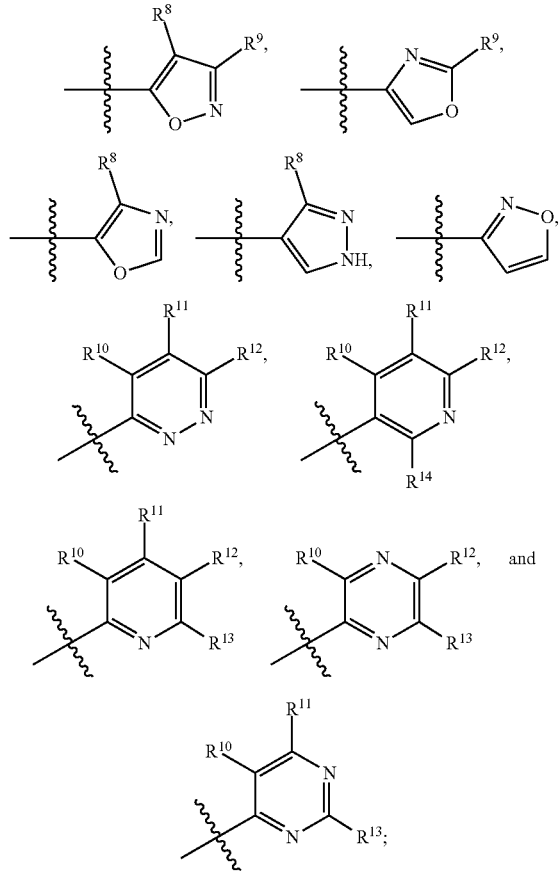

and wherein, $R^8$ and $R^9$ are independently selected from H, D, ($C_1$-$C_3$) alkyl, ($C_1$-$C_3$) alkenyl, halo, cyano, hydroxyl, nitro, thiol, and amino; $R^{10}$-$R^{14}$ are independently selected from H, D, ($C_1$-$C_3$) alkyl, ($C_1$-$C_3$) alkenyl, halo, cyano, hydroxyl, nitro, thiol, amino, $OC(R^{15})_3$, $OCH(R^{15})_2$, $OCH_2(R^{15})$,

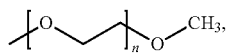

wherein n is an integer from 1 to 5; and wherein $R^{15}$ is independently H, halo, or a ($C_1$-$C_3$) alkyl. In still another or further embodiment of any of the foregoing the compound has a structure selected from the group consisting of:

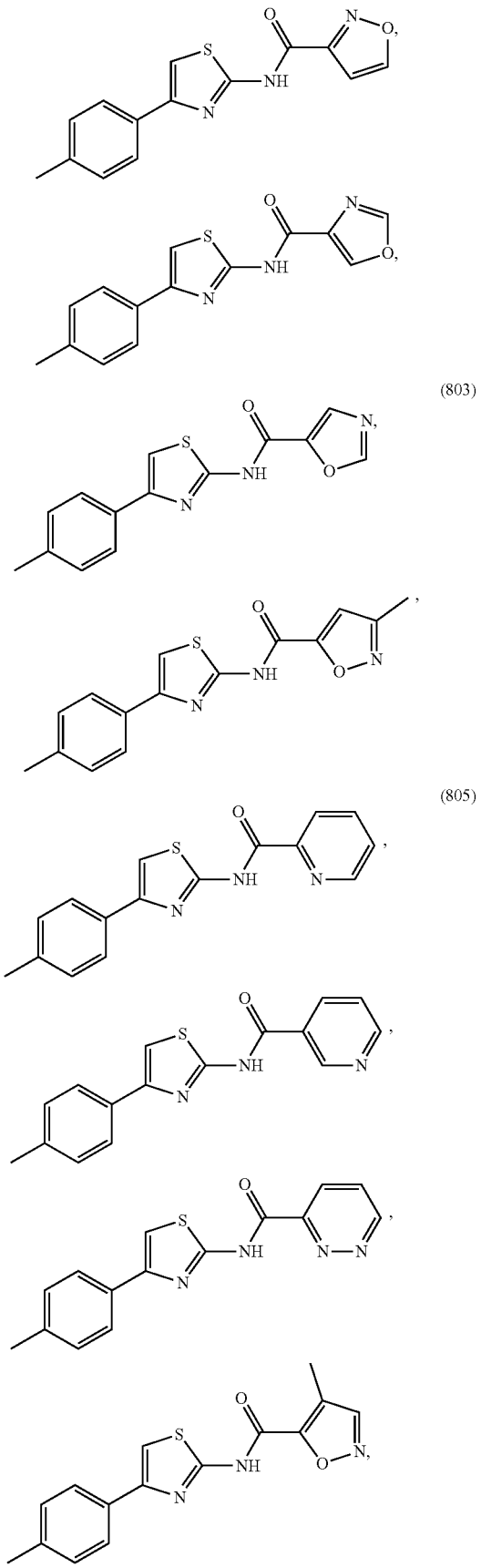

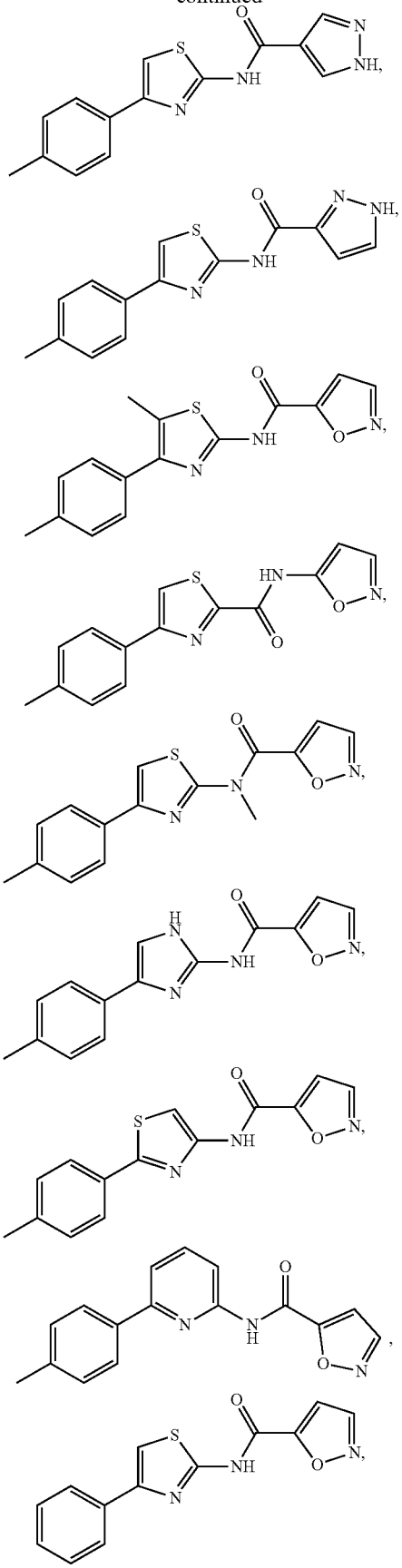
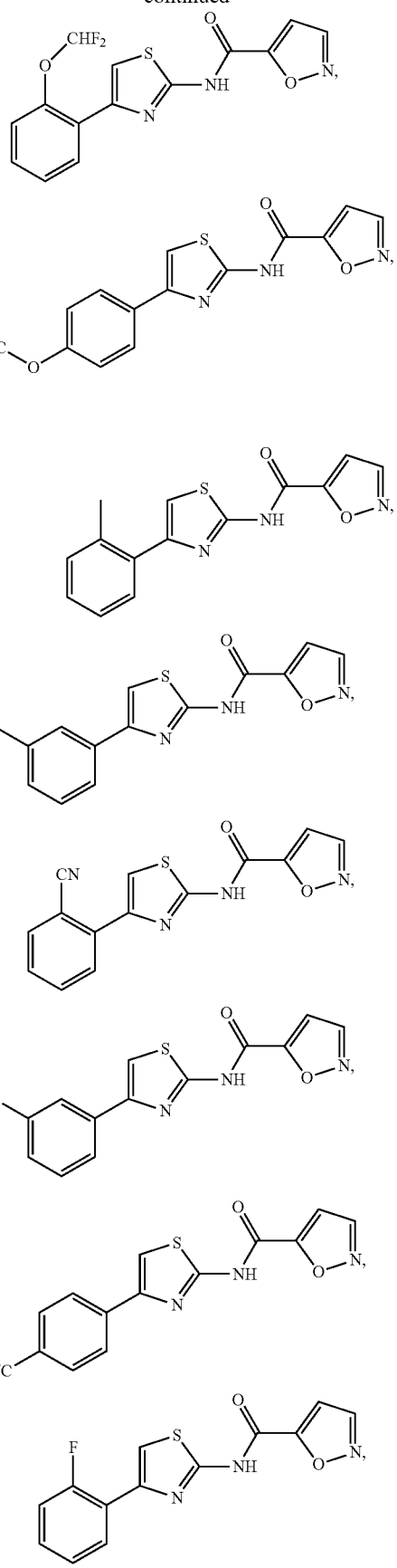

-continued

-continued

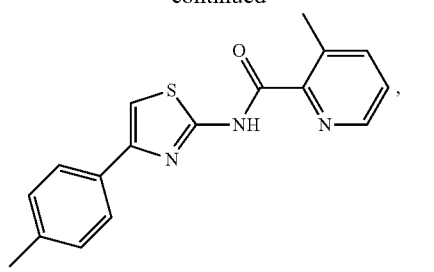

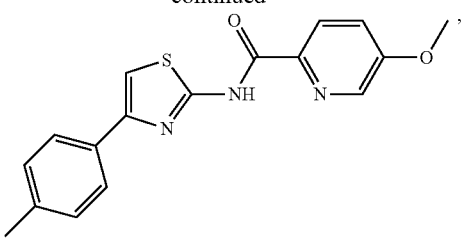

(815)

(839)

In another embodiment, the compound modulates STAT3 and MYC signaling. In one embodiment, the compound does not stimulate STAT3 and MYC signaling. In another embodiment, the compound stimulates STAT3 and MYC signaling.

The disclosure also provides a method of treating an inflammatory disease or disorder or cell-proliferative disease or disorder comprising contacting a subject with a compound as described herein and above. In one embodiment, the inflammatory disease or disorder or cell proliferative disease or disorder is selected from the group consisting of stroke; heart disease; cartilage degeneration; hair loss;

wound healing; arthritis; neurodegenerative disorders; aging; diseases known to be associated with low grade chronic inflammation; immune disorders including psoriasis, rosacea, lupus, rheumatoid arthritis, inflammatory bowel disease; and cancer.

The disclosure also provides a method of modulating IL-6 mediated inflammatory responses in a cell comprising contacting the cell with a compound as described herein and above. In one embodiment, the cell is a chondrocyte.

The disclosure also provides a composition comprising a pharmaceutically acceptable carrier and a compound as described herein and above.

The disclosure also provides a method of treating an acute of chronic inflammatory state comprising contact a subject with a compound or pharmaceutical as described herein and above.

The disclosure also provides a method of decreasing an activated inflammatory pathway in a cell comprising contact the cell with a compound or pharmaceutical as described herein and above.

The disclosure provides a method of inhibiting the production or induction of pro-inflammatory genes, cytokines or mediators comprising contacting a cell or subject with a compound or pharmaceutical as described herein and above.

The disclosure provides a method of inhibiting the production or induction of extracellular matrix degrading enzymes comprising contacting a cell or subject with a compound or pharmaceutical as described herein and above.

DESCRIPTION OF DRAWINGS

FIG. 7A-B shows gp130$^{-/-}$ Ba/F3 cells (A) only increase gp130 signaling in the presence of RCGD 423 and WT gp130 (B).

FIG. 15A-C shows CX-011 has little effect on endogenous levels of proteins mediating pro-inflammatory signals but strongly inhibits increases in these proteins in the presence of OSM (A). CX-011 prevents the breakdown of collagen and aggrecan in pig articular cartilage explants driven by OSM as indicated by lower levels of degeneration epitopes (B) and increase in catalytic enzymes (C).

FIG. 25A-B shows that molecule 805 strongly inhibits OSM-mediated activation of gp130 (A) and its downstream effector JAK2 (B). Adult human articular chondrocytes from three independent donors were used to generate these results.

FIG. 26 shows validations of the effect of molecule 805 on fresh pig cartilage explants. 72 hour exposure to the drug and OSM. 805 strongly prevents the breakdown of collagen and aggrecan in pig articular cartilage explants driven by OSM as indicated by lower levels of degeneration epitopes for aggrecan (aggrecan-neo) and collagen 2 (collagen-neo). Effect is concentration dependent and increases with increase in drug concentration.

FIG. 27A-C shows 805 has little effect on endogenous levels of proteins mediating pro-inflammatory signals but strongly inhibits increases in these proteins in the presence of OSM (A). 805 prevents the breakdown of collagen and aggrecan in pig articular cartilage explants driven by OSM as indicated by lower levels of degeneration epitopes (B) and increase in catalytic enzymes (C).

FIG. 33A-B shows that molecule 805 strongly inhibits OSM-mediated secretion of TNF-α (A) and IL-6 (B). Adult synovial cells from three independent donors were used. Molecule 805 was used at 10 µM.

FIG. 34 shows that oral administration of a single dose of molecule 805 reduced synovial inflammation in rat joints.

DETAILED DESCRIPTION

Figures 1A, 1B:
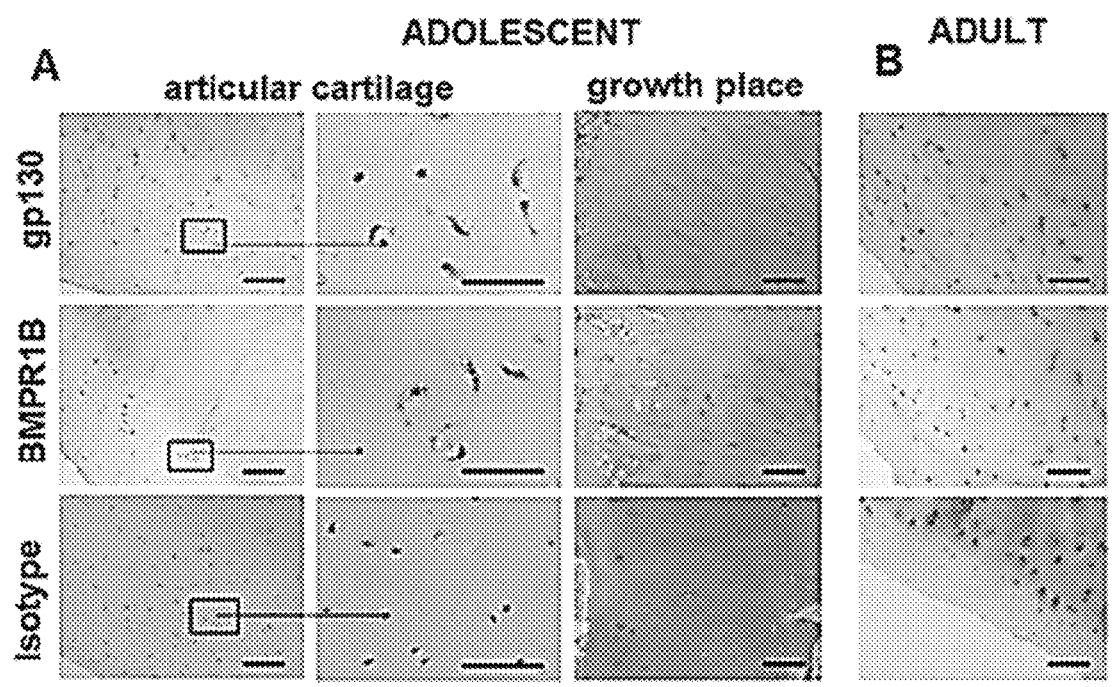
FIG. 1A-B shows (A) Expression of gp130 is enriched on superficial chondrocytes that are also marked by BMPR1B in human adolescents (left two columns) and (B) adults.

As used herein and in the appended claims, the singular forms "a," "an," and "the" include plural referents unless the context clearly dictates otherwise. Thus, for example, reference to "a chondrocyte" includes a plurality of such chondrocytes and reference to "an antagonist" includes reference to one or more antagonists or equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood by one of ordinary skill in the art to which this disclosure belongs. Although many methods and reagents similar to or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The term "alkyl" refers to an organic group that is comprised of carbon and hydrogen atoms that contains single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 2 to 30 carbon atoms, unless stated otherwise. While a $C_2$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of non-conjugation. Additionally, if there is more than 2 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 2 to 30 carbon atoms, unless stated otherwise. While a $C_2$-alkynyl can form a triple bond to a carbon of a parent chain, an alkynyl group of three or more carbons can contain more than one triple bond. Where if there is more than 2 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", refers to a conjugated planar ring system with delocalized pi electron clouds that contain only carbon as ring atoms. An "aryl" for the purposes of this disclosure encompasses from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

The "binding site 1" of the gp130 receptor, or "binding site 1 gp 130 receptor" is a binding pocket within the gp 130 receptor. The sequence for the gp130 receptor is set forth in SEQ ID NO: 1. The sequence for the binding site 1 of the gp130 receptor is set forth in SEQ ID NO:2 and SEQ ID NO:3 and includes amino acids corresponding to positions 173, 174, 175 and 176 in gp130 or amino acid residues KAKR as set forth in SEQ ID NO:4. An amino acid residue in a protein or receptor "corresponds" to a given residue when it occupies the same essential structural position within the protein or receptor as the given residue, for example, in homologous proteins that may have a different numbering convention. The amino acid residues and fragments of gp130 disclosed herein are referred to as corresponding to the entire (918 amino acid) length of gp130 and/or gp130 without the signaling fragment that is 22 amino acid residues in length (e.g, KAKR as set forth in SEQ ID NO:4 is referred to herein as corresponding to positions 173, 174, 175 and 176 and/or positions 151, 152, 153 and 154 in gp130).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "cycloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 7 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cycloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 7 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

"Disease" or "condition" refer to a state of being or health status of a patient or subject capable of being treated with the compounds/molecules or methods provided herein. Disease as used herein may refer to inflammatory diseases and disorders and immune diseases and disorders such as cartilage degenerative disease, joint surface injury or arthritis (including rheumatoid arthritis), psoriasis, inflammatory bowel disease, aging, lupus, rosacea and the like.

For purposes of this disclosure, the term "extended mixed ring system" refers to a group that is comprised of at least 2 ring structures, but no more than 7 ring structures. An "extended mixed ring system" is comprised of at least one ring functional group that is different from another ring functional group. Examples of ring groups include, but are not limited to, cycloalkyl, cycloalkenyl, cycloalkynyl, aryl, and heterocycle. Each ring may be optionally substituted. The rings comprising the mixed extended ring system may be joined so that they are linked, fused, or a combination thereof.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

The term "gp130" as used herein refers to glycoprotein 130, a cell surface receptor that is expressed ubiquitously in the body. Activation of gp130 is essential for several physiological functions, including but not limited to, acute-phase response to injury and infection, fertility, metabolism, haematopoiesis, neuroprotection, anti-angiogenesis, and melanoma and tumor cell suppression. Gp130 is activated by a ligand from the IL-6 family of cytokines, including but not limited to, IL-6, IL-11, leukemia inhibitory factor (LIF), Oncostatin M (OSM), ciliary neurotrophic factor (CNTF), cardiotrophin-1 (CT-1) and cardiotrophin-like cytokine (CLC). Activation of gp130 signaling may be direct, i.e. activation may be triggered by binding of the ligand directly to gp130 (i.e., IL-6 or IL-11, which result in gp130-homodimerization). Activation of gp130 signaling may also be indirect by binding of the ligand to another cell surface receptor, which forms a complex with gp130, thereby activating it. LIF, CT-1, CNTF, OSM and CLC form heterodimers of gp130 and LIFR, whereas OSM may also form a heterodimer of gp130 and OSMR. Therefore, LIF, CT-1, CNTF, OSM and CLC may activate gp130 signaling directly, by binding gp130 first, or indirectly, by binding LIFR/OSMR and then recruiting gp130 to the complex. The ligands of the IL-6 cytokine family trigger the JAK/STAT pathway, the first event of which is the ligand-induced homo- or hetero-dimerization of signal-transducing receptor subunits. All IL-6-type cytokines recruit gp130 to their receptor complexes. They either signal via gp130 alone or in combination with LIFR or OSMR, which are all able to activate Jaks and to recruit STAT proteins. The terms "gp130 receptor," "gp130," gp130 protein," "IL6ST receptor," "IL6ST" or "IL6ST protein" are here used interchangeably and according to their common, ordinary meaning (e.g., transmembrane protein "glycoprotein 130") and refer to proteins of the same or similar names and functional fragments and homologs thereof. The term includes any recombinant or naturally occurring form of, or variants thereof that maintain gp130 activity (e.g. within at least 30%, 40%, 50%, 60%, 70%, 80%, 90%, 95%, or 100% activity compared to gp130). In embodiments, the gp 130 receptor has at least 80%, 85%, 90%, 95%, 96%, 97%, 98%, 99% or 100% sequence identity to SEQ ID NO:1 or a functional fragment thereof (e.g. 700 contiguous amino acids of SEQ ID NO:1, 750 contiguous amino acids of SEQ ID NO:1, 800 contiguous amino acids of SEQ ID NO:1, 850 contiguous amino acids of SEQ ID NO:1 870 contiguous amino acids of SEQ ID NO:1, 880 contiguous amino acids of SEQ ID NO:1, 890 contiguous amino acids of SEQ ID NO: 1, 900 contiguous amino acids of SEQ ID NO:1 or 910 contiguous amino acids of SEQ ID NO:1).

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "heterocycle", as used in this disclosure, refers to ring structures that contain at least 1 noncarbon ring atom. A "heterocycle" for the purposes of this disclosure encompass from 1 to 7 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane, 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

"Inflammation" refers to a complex biological response of a body to a stimulus (e.g., a pathogen, cellular damage or an irritant). Inflammation, when prolonged, can lead to an inflammatory disease or disorder. Factors elicited during an inflammatory reaction include pro-inflammatory cytokines (e.g., TNF-a, IL-1, INF-γ, MCP-1), cellular migration (e.g., monocytes, macrophages, lymphocytes, plasma cells) and serum proteins (e.g., serum amyloid A (SAA) and serum amyloid P (SAP)). Inflammation can be local (e.g., vascular inflammation) or systemic.

"Inflammatory disorder" or "inflammatory disease" refers to a condition characterized by inflammation in a cell, tissue or body. Inflammatory diseases and disorders include, but are not limited to, hypersensitivities (e.g., allergies), asthma, autoimmune disease (e.g., rheumatoid and osteo arthritis, lupus, multiple sclerosis), cancer, diabetes, inflammatory bowel disease (IBD) or cardiovascular disease (e.g., atherosclerosis), NAFLD, NASH, hepatitis, fibrosis, and cirrhosis.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "pharmaceutically acceptable" as in pharmaceutically acceptable salt or pharmaceutically acceptable counter ion, refers to compounds, salts, or ions that are tolerated by a subject for topical, or internal use.

The term "pharmaceutically acceptable salt" refers to making a salt formation of a compound disclosed herein. Salt formation can be used as a means of varying the properties of the compounds disclosed herein, for example, to increase or decrease solubility of the compounds, to improve stability of the compounds, to reduce toxicity of the compounds, and/or to reduce the hygroscopicity of the compounds. There are a wide range of chemically diverse acids and bases, with a range of pKa values, molecular weights, solubilities and other properties, that can used for making pharmaceutically acceptable salts of the compounds disclosed herein. Examples of pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the disclosure can form pharmaceutically acceptable salts with various amino acids. Examples of pharmaceutically acceptable base addition salts include, but are not limited to, aluminum, calcium, lithium, magnesium, potassium, sodium, zinc, and diethanolamine salts. For additional examples of pharmaceutical salts that can used to practice this disclosure, see P. H. Stahl and C. G. Wermuth (eds.), *Pharmaceutical Salts: Properties, Selection, and Use* (2d ed. 2011) Wiley and Sons Publisher, ISBN: 978-3-90639-051-2.

The term "pharmaceutically acceptable counter ion" either refers to pharmaceutically acceptable cations including, but not limited to, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyls, i.e., including, methyl, ethyl, or hydroxyethyl, specifically, trimethyl ammonium, triethyl ammonium, and triethanol ammonium cations); or pharmaceutically-acceptable anions including, but not limited to, halides (e.g., $Cl^-$, $Br^-$), sulfate, acetates (e.g., acetate, trifluoroacetate), ascorbates, aspartates, benzoates, citrates, and lactate.

A "subject" generally refers to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

The term "substantially" as used to modify a term means that the modified term includes minor variations in size, purity, structure and the like by only a minor amount. Accordingly, "substantially homogenous in size" means that the material does not vary by more than 1%, 5%, 10%, 20% or 30% (or any value there between) in size from an average size.

The term "substituted" with respect to heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

A "therapeutically effective amount," refers to an amount of a compound, molecule or composition of the disclosure that reduces a symptom or symptoms (and grammatical equivalents of this phrase) or the severity of or frequency of the symptom(s), or elimination of the symptom(s) associated with a disease or disorder to be treated. A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "unsubstituted" with respect to hydrocarbons, heterocycles, and the like, refers to structures wherein the parent chain contains no substituents.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

A bond indicated by a straight line and a dashed line indicates a bond that may be a single covalent bond or alternatively a double covalent bond. But in the case where an atom's maximum valence would be exceeded by forming a double covalent bond, then the bond would be a single covalent bond.

It should be understood many of the reagents and starting materials used in the Schemes presented herein are readily available from various commercial suppliers, such as Sigma-Aldrich, Alfa Aesar, Tokyo Chemical Industry Co., LTD, etc. Moreover, many of these same reagents and starting materials can be modified to incorporate additional functional groups by using standard organic synthesis reactions.

When a compound disclosed herein contains an acidic or basic moiety, it may also disclosed as a pharmaceutically acceptable salt (See, Berge et al., J. Pharm. Sci. 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)- camphor-10-sulfonic acid, capric acid, caproic acid, caprylic acid, cinnamic acid, citric acid, cyclamic acid, cyclohexane-sulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (+/−)-DL-lactic acid, lactobionic acid, lauric acid, maleic acid, (−)-L-malic acid, malonic acid, (+/−)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The disclosure provides that compounds disclosed herein can have prodrug forms. Prodrugs of the compounds are useful in the methods of this disclosure. Any compound that will be converted in vivo to provide a biologically, pharmaceutically or therapeutically active form of a compound of the disclosure is a prodrug. Various examples and forms of prodrugs are well known in the art. Examples of prodrugs are found, inter alia, in *Design of Prodrugs*, edited by H. Bundgaard, (Elsevier, 1985), Methods in Enzymology, Vol. 42, at pp. 309-396, edited by K. Widder, et al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Prodrugs of compounds disclosed herein can be prepared by methods known to one of skill in the art and routine modifications thereof, and/or procedures found in U.S. Pat No. 8,293,786, and references cited therein and routine modifications made thereof.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy to administer by a syringe. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound, e.g. a compound disclosed herein, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

In a particular embodiment, one or more compounds of the disclosure are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to cells with monoclonal antibodies) can also be used as pharmaceutically acceptable carriers. These can be prepared according to methods known to those skilled in the art, for example, as described in U.S. Pat. No. 4,522,811.

The data obtained from the cell culture assays and animal studies can be used in formulating a range of dosage for use in humans. The dosage of such compounds lies within a range of circulating concentrations that include the $ED_{50}$ with little or no toxicity. The dosage may vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (e.g., the concentration of the test compound which achieves a half-maximal inhibition of symptoms) as determined in cell culture. Such information can be used to more accurately determine useful doses in humans. Levels in plasma can be measured, for example, by high performance liquid chromatography.

Compositions and formulations of one or more compounds disclosed herein can be used in combination with other active agents to treat a disorder or disease in a subject.

It should be understood that the administration of an additional therapeutic agent with a compound of the disclosure encompasses co-administration of these therapeutic agents in a substantially simultaneous manner, such as in a single capsule having a fixed ratio of active ingredients or in multiple, separate capsules for each active ingredient. In addition, administration of an additional therapeutic agent in combination with a compound disclosed herein also encompasses use of each type of therapeutic agent in a sequential manner. In either case, the treatment regimen will provide beneficial effects of the drug combination in treating the disorders described herein.

In a further embodiment, the compounds disclosed herein can be combined with one or more class of therapeutic agents, including, but not limited to, alkylating agents, cancer immunotherapy monoclonal antibodies, anti-metabolites, mitotic inhibitors, anti-tumor antibiotics, topoisomerase inhibitors, photosensitizers, tyrosine kinase inhibitors, anti-cancer agents, chemotherapeutic agents, anti-migraine treatments, anti-tussives, mucolytics, decongestants, anti-allergic non-steroidals, expectorants, anti-histamine treatments, anti-retroviral agents, CYP3A inhibitors, CYP3A inducers, protease inhibitors, adrenergic agonists, anti-cholinergics, mast cell stabilizers, xanthines, leukotriene antagonists, glucocorticoid treatments, antibacterial agents, antifungal agents, sepsis treatments, steroidals, local or general anesthetics, NSAIDS, NRIs, DARIs, SNRIs, sedatives, NDRIs, SNDRIs, monoamine oxidase inhibitors, hypothalamic phosphpholipids, anti-emetics, ECE inhibitors, opioids, thromboxane receptor antagonists, potassium channel openers, thrombin inhibitors, growth factor inhibitors, anti-platelet agents, P2Y(AC) antagonists, anti-coagulants, low molecular weight heparins, Factor VIa inhibitors, Factor Xa inhibitors, renin inhibitors, NEP inhibitors, vasopepsidase inhibitors, squalene synthetase inhibitors, anti-atherosclerotic agents, MTP inhibitors, calcium channel blockers, potassium channel activators, alpha-muscarinic agents, beta-muscarinic agents, anti-arrhythmic agents, diuretics, thrombolytic agents, anti-diabetic agents, mineralocorticoid receptor antagonists, growth hormone secretagogues, aP2 inhibitors, phophodiesterase inhibitors, anti-inflammatories, anti-proliferatives, antibiotics, farnesyl-protein transferase inhibitors, hormonal agents, plant-derived products, epipodophyllotoxins, taxanes, prenyl-protein transferase inhibitors, anti-TNF antibodies and soluble TNF receptors, Cyclooxygenase-2 inhibitors, and miscellaneous agents.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

Traditionally, cartilage has been considered to be a static tissue, with little to no cellular turnover or capacity for repair following injury. However, detailed analysis of articular cartilage tissues from a variety of species has identified a primitive stem/progenitor chondrocyte population located within the layer of cartilage closest to the joint space, termed the superficial zone. These cells are capable of proliferating and producing hyaline matrix, and mouse lineage tracing studies show these cells maintain cartilage throughout life, but it is clear that they lack sufficient capacity to effect substantive regeneration in most injury contexts. Moreover, there is a paucity of information on how to positively identify these cells in humans and understand their biology. Finally, pro-inflammatory signaling that often accompanies cartilage injury is a major inhibitor of proliferation while also driving apoptosis.

The pathogenesis of osteoarthritis (OA) often begins from an injury to articular cartilage, which establishes chronic, low-grade inflammation mediated by interleukin-6/glycoprotein 130 (IL-6/gp130) and other factors that promote matrix degradation over time and eventual destruction of cartilage. IL-6 signaling through IL-6R/gp130 suppresses chondrocyte proliferation, promotes mineralization in articular cartilage, downregulation of matrix proteins and increases expression of matrix-degrading proteases. Moreover, blockade of IL-6 in vivo in mouse models of OA has been shown to be chondroprotective. Importantly, higher serum levels of IL-6 have been correlated with the development of OA in humans, and a monoclonal antibody against IL-6R is currently in Phase III clinical trials for the treatment of hand OA (NCT02477059). Signaling downstream of IL-6/gp130 is mediated by multiple pathways, including signal transducer and activator of transcription 3 (STAT3). STAT3 has been demonstrated to have pleiotropic effects during chondrogenesis and in articular chondrocytes. During chondrogenic differentiation of multipotent mesenchymal stem cells, IL-6/STAT3 signaling promotes chondrocyte commitment and matrix production. Similarly, loss of STAT3 during limb formation results in increased hypertrophy, premature ossification and decreases in expression of the master regulator of chondrocyte identity SOX9. In contrast, in adult articular chondrocytes inhibition of STAT3 downstream of IL-6 is chondroprotective, reducing the severity of OA-like pathology in a mouse model. Together, these data indicate that IL-6/STAT3 signaling can drive matrix loss and development of OA in vivo in both mouse models and humans.

Recent studies have shown that Bone Morphogenetic Protein receptor 1B (BMPR1B) marks superficial chondrocytes throughout human ontogeny and also in rodent joints. As described herein these cells can also be identified by their high level of IL-6 coreceptor gp130 expression and activity. Based on the known role of IL-6/gp130 signaling in hypertrophy and OA pathogenesis, a small molecule screen was performed to identify potential agents to manipulate gp130 signaling. These studies revealed Regulator of Cartilage Growth and Differentiation 423 (RCGD 423), a small molecule modulator of gp130.

RCGD 423 has the general structure of Formula A:

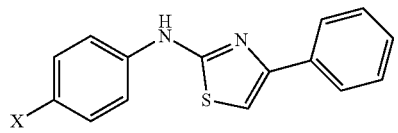

Formula A wherein X is F or Br (see, e.g., WO/2016/138533, which is incorporated herein by reference for all purposes).

In vitro studies demonstrated that RCGD 423 signals through gp130 and interacts with the extracellular region of gp130. Further elucidation of the mechanism of RCGD 423 demonstrated that it promotes the formation of active, ligand-independent gp130 homodimers, thereby distinguishing its activity from IL-6 family cytokines; this was reflected in critical differences in the downstream molecular events of IL-6 family cytokine and RCGD 423 stimulation. Moreover, RCGD 423 actively competes with signaling by pro-inflammatory IL-6 family cytokines by sequestering gp130 away from forming heterodimers with IL-6R. Finally, in a rat model of OA, this molecule evidenced a remarkable ability to prevent cartilage degeneration.

A close analog of RCGD 423 has been shown to stimulate hair cycle in mice through stabilization of MYC protein, thus validating the mechanism of action of this compound in a completely independent system. However, despite these positive results, increases in pSTAT3 and MYC levels may be detrimental in a clinical OA pathology scenario, based on potential pro-degenerative and oncogenic concerns, respectively.

RCGD 423 provided information regarding the specific regulatory pockets/clefts in gp130. Using this information, modeling and bench research led to the identification of small molecules that interacted with the gp130 pockets/clefts. In particular, the research identified a plurality of molecules provided in Table 1. For example, one such molecule CX-011 (also referred to as "B8" herein) and related analogs are shown to be potent inhibitor of pro-catabolic signaling by IL-6 family cytokines and which do not affect levels of pSTAT3 or MYC protein.

In a particular embodiment, the disclosure provides for a compound that interacts with domain 2 of gp130 and which may lock gp130 into a non-permissive conformation and/or produce atypical gp130 homodimers, wherein the compound comprises the structure of Formula I, II or III:

Formula I

Formula II

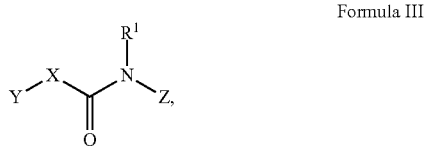

Formula III wherein,

X is

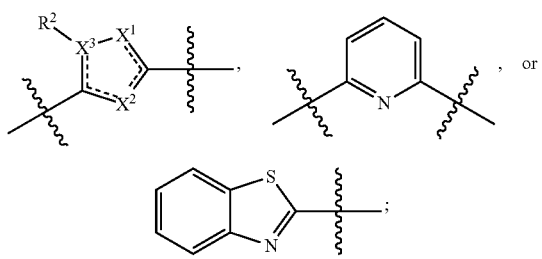

Y is

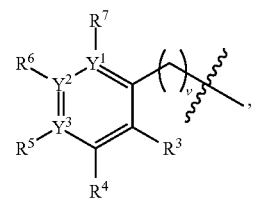

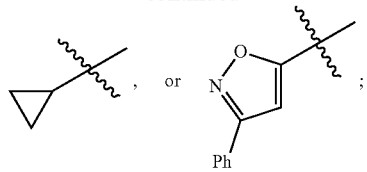

Z is

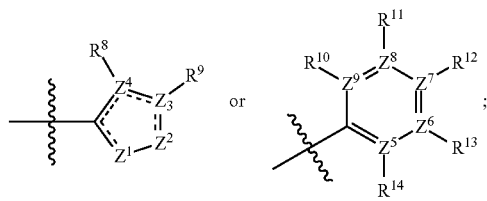

$X^1$ is S, CH, or NH;
$X^2$ is S, CH, or N;
$X^3$ is $CR^2$ or S;
$Y^1$ is $CR^7$ or N;
$Y^2$ is $CR^6$ or N;
$Y^3$ is $CR^5$ or N;
$Z^1$ is O or CH;
$Z^2$ is O, N, NH or CH;
$Z^3$ is $CR^9$ or N;
$Z^4$ is $CR^8$ or N;
$Z^5$ is N or $CR^{14}$;
$Z^6$ is N or $CR^{13}$;
$Z^7$ is N or $CR^{12}$;
$Z^8$ is N or $CR^{11}$;
$Z^9$ is N or $CR^{10}$;
v is 0 or 1;
$R^1$, $R^2$, $R^8$ and $R^9$ are independently selected from H, D, $(C_1-C_3)$ alkyl, $(C_1-C_3)$alkenyl, halo, cyano, hydroxyl, nitro, thiol, and amino;
$R^3$-$R^7$ and $R^{10}$-$R^{14}$ are independently selected from H, D, $(C_1-C_3)$ alkyl, $(C_1-C_3)$ alkenyl, halo, cyano, hydroxyl, nitro, thiol, amino, OC $(R^{15})_3$, $OCH(R^{15})_2$, $OCH2 (R^{15})$,

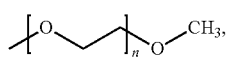

wherein n is an integer from 1 to 5; and
$R^{15}$ is independently H, halo, or a $(C_1-C_3)$alkyl.

In another embodiment, the disclosure provides for a compound that interacts with domain 2 of gp130 and which may lock gp130 into a non-permissive conformation and/or produce atypical gp130 homodimers, wherein the compound comprises the structure of Formula I, II or III:

Formula I

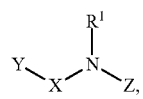

Formula II

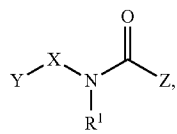

Formula III

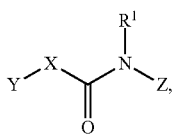

wherein,
X is selected from the group consisting of

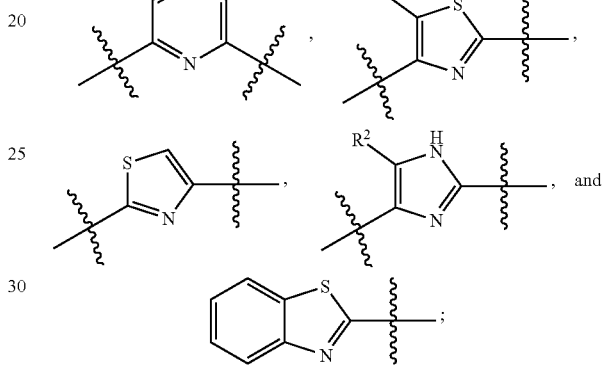

Y is

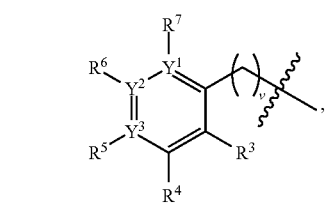

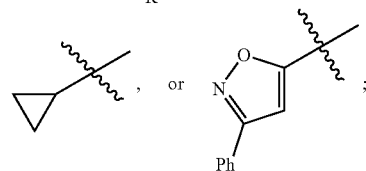

Z is

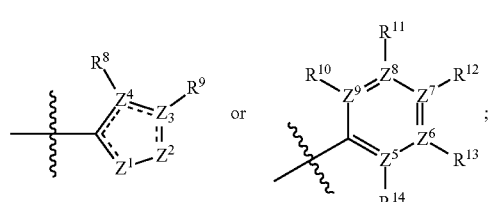

$Y^1$ is $CR^7$ or N;
$Y^2$ is $CR^6$ or N;
$Y^3$ is $CR^5$ or N;

$Z^1$ is O or CH;
$Z^2$ is O, N, NH or CH;
$Z^3$ is $CR^9$ or N;
$Z^4$ is $CR^8$ or N;
$Z^5$ is N or $CR^{14}$;
$Z^6$ is N or $CR^{13}$;
$Z^7$ is N or $CR^{12}$;
$Z^8$ is N or $CR^{11}$;
$Z^9$ is N or $CR^{10}$;
v is 0 or 1;
$R^1$, $R^2$, $R^8$ and $R^9$ are independently selected from H, D, $(C_1-C_3)$ alkyl, $(C_1-C_3)$alkenyl, halo, cyano, hydroxyl, nitro, thiol, and amino;
$R^3$-$R^7$ and $R^{10}$-$R^{14}$ are independently selected from H, D, $(C_1-C_3)$ alkyl, $(C_1-C_3)$ alkenyl, halo, cyano, hydroxyl, nitro, thiol, amino, OC $(R^{15})_3$, $OCH(R^{15})_2$, OCH2 $(R^{15})$,

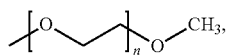

wherein n is an integer from 1 to 5; and
$R^{15}$ is independently H, halo, or a $(C_1-C_3)$ alkyl.

In yet another embodiment, the disclosure provides for a compound that interacts with domain 2 of gp130 and which may lock gp130 into a non-permissive conformation and/or produce atypical gp130 homodimers, wherein the compound comprises the structure of Formula I, II or III:

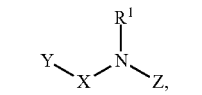 Formula I

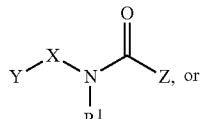 Formula II

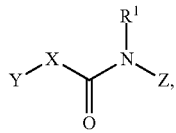 Formula III wherein,
X is

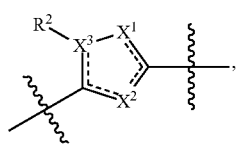

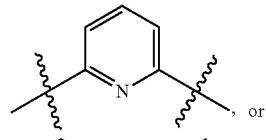, or

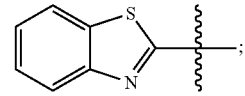;

Y is selected from the group consisting of:

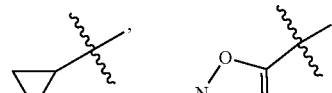

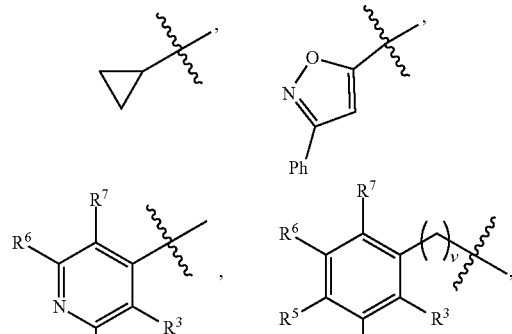

Z is

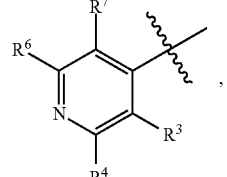 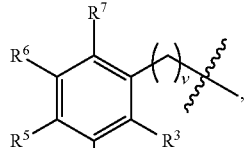 or

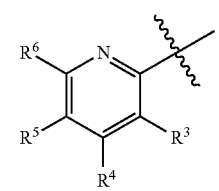 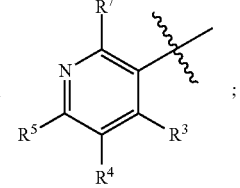

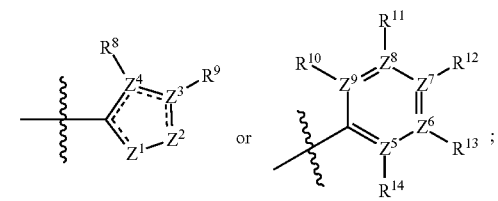

$X^1$ is S, CH, or NH;
$X^2$ is S, CH, or N;
$X^3$ is $CR^2$ or S;
$Z^1$ is O or CH;
$Z^2$ is O, N, NH or CH;
$Z^3$ is $CR^9$ or N;
$Z^4$ is $CR^8$ or N;
$Z^5$ is N or $CR^{14}$;
$Z^6$ is N or $CR^{13}$;
$Z^7$ is N or $CR^{12}$;
$Z^8$ is N or $CR^{11}$;
$Z^9$ is N or $CR^{10}$;
v is 0 or 1;
$R^1$, $R^2$, $R^8$ and $R^9$ are independently selected from H, D, $(C_1-C_3)$ alkyl, $(C_1-C_3)$alkenyl, halo, cyano, hydroxyl, nitro, thiol, and amino;
$R^3$-$R^7$ and $R^{10}$-$R^{14}$ are independently selected from H, D, $(C_1-C_3)$ alkyl, $(C_1-C_3)$ alkenyl, halo, cyano, hydroxyl, nitro, thiol, amino, OC $(R^{15})_3$, $OCH(R^{15})_2$, OCH2 $(R^{15})$,

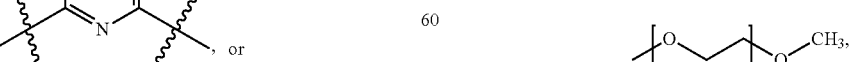

wherein n is an integer from 1 to 5; and
$R^{15}$ is independently H, halo, or a $(C_1-C_3)$alkyl.

In a further embodiment, the disclosure provides for a compound that interacts with domain 2 of gp130 and which can lock gp130 into a non-permissive conformation and/or produce atypical gp130 homodimers, wherein the compound comprises the structure of Formula I, II or III:

Formula I

Formula II

Formula III wherein,

X is

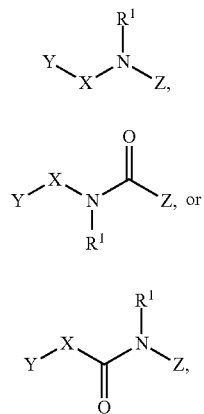

Y is

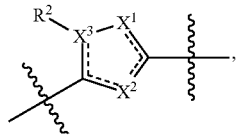

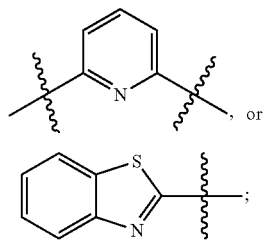

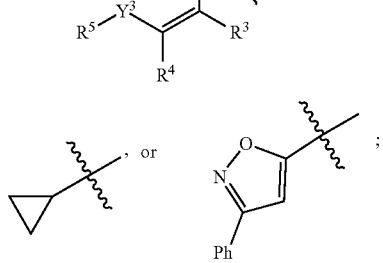

Z is selected from the group consisting of:

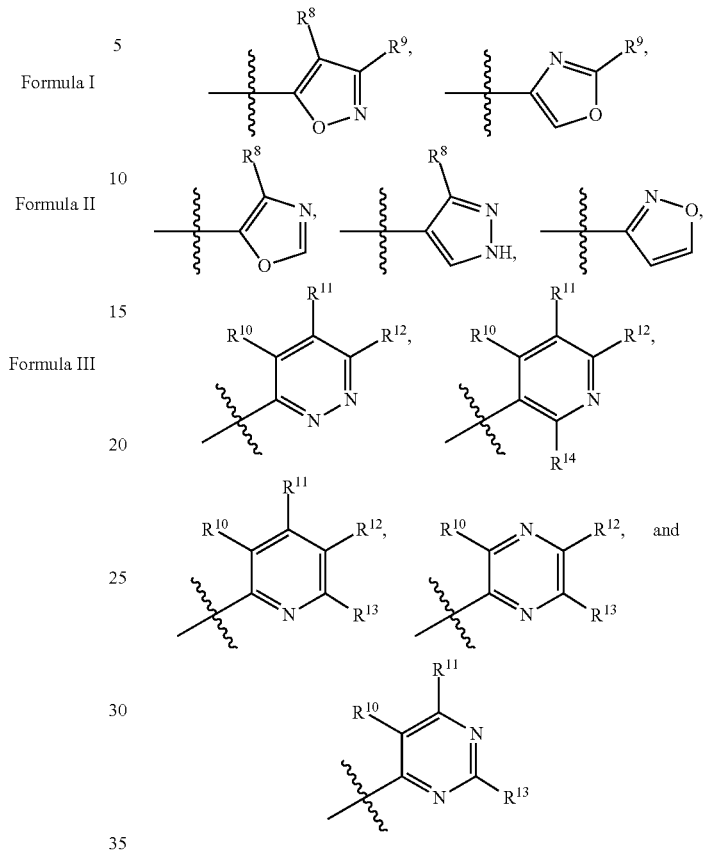

$X^1$ is S, CH, or NH;
$X^2$ is S, CH, or N;
$X^3$ is $CR^2$ or S;
$Y^1$ is $CR^7$ or N;
$Y^2$ is $CR^6$ or N;
$Y^3$ is $CR^5$ or N;
v is 0 or 1;
$R^1$, $R^2$, $R^8$ and $R^9$ are independently selected from H, D, $(C^1-C_3)$alkyl, $(C_1-C_3)$alkenyl, halo, cyano, hydroxyl, nitro, thiol, and amino;
$R^3$-$R^7$ and $R^{10}$-$R^{14}$ are independently selected from H, D, $(C^1-C_3)$alkyl, $(C_1-C_3)$alkenyl, halo, cyano, hydroxyl, nitro, thiol, amino, $OC(R^{15})_3$, $OCH(R^{15})_2$, $OCH2(R^{15})$,

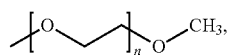

wherein n is an integer from 1 to 5; and
$R^{15}$ is independently H, halo, or a $(C_1-C_3)$alkyl.

In a particular embodiment, the disclosure provides for a compound that interacts with domain 2 of gp130 and which may lock gp130 into a non-permissive conformation and/or produce atypical gp130 homodimers, wherein the compound comprises the structure of Formula I, II or III:

Formula I

-continued

Formula II

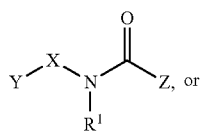

Formula III

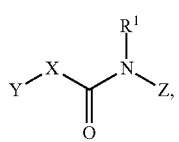

wherein,

X is selected from the group consisting of:

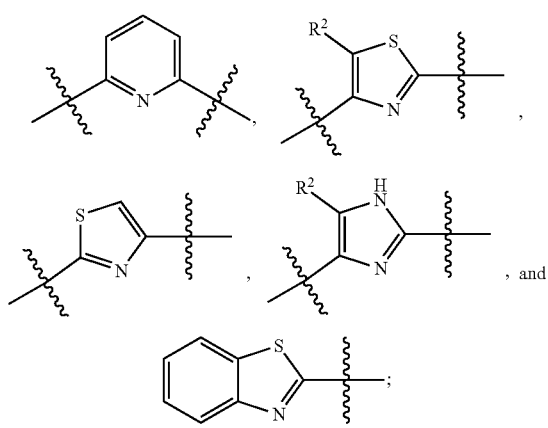

Y is selected from the group consisting of:

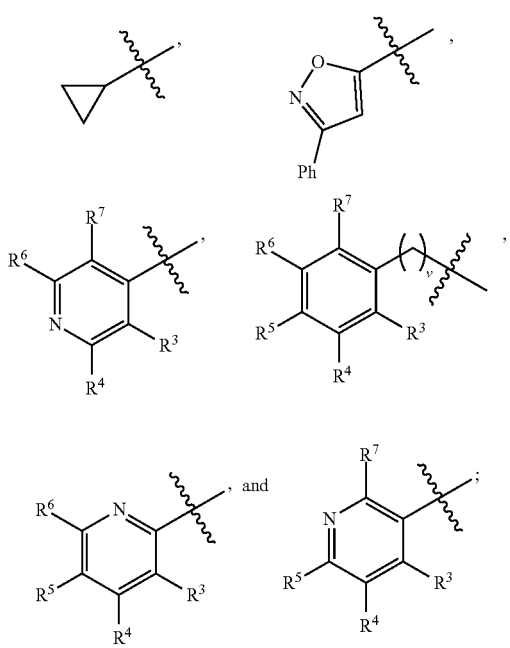

Z is selected from the group consisting of:

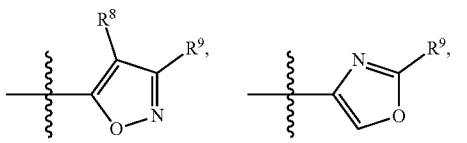

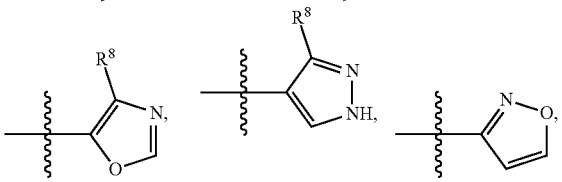

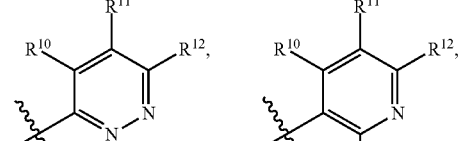

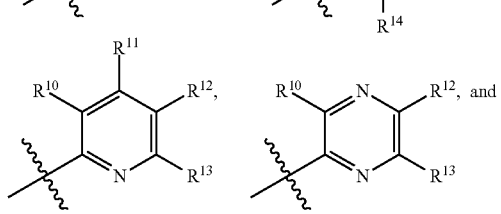

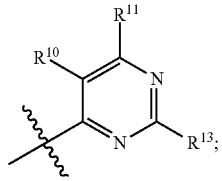

v is 0 or 1;

$R^1$, $R^2$, $R^8$ and $R^9$ are independently selected from H, D, $(C_1$-$C_3)$alkyl, $(C_1$-$C_3)$alkenyl, halo, cyano, hydroxyl, nitro, thiol, and amino;

$R^3$-$R^7$ and $R^{10}$-$R^{14}$ are independently selected from H, D, $(C_1$-$C_3)$alkyl, $(C_1$-$C_3)$alkenyl, halo, cyano, hydroxyl, nitro, thiol, amino, $OC(R^{15})_3$, $OCH(R^{15})_2$, $OCH_2(R^{15})$,

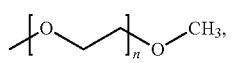

wherein n is an integer from 1 to 5; and $R^{15}$ is independently H, halo, or a $(C_1$-$C_3)$alkyl.

In a certain embodiment, the disclosure provides for a compound that interacts with domain 2 of gp130 and which locks gp130 into a non-permissive conformation and/or produce atypical gp130 homodimers, wherein the compound has a structure selected from the group consisting of:

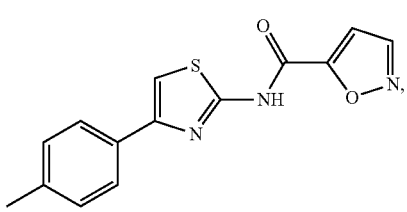

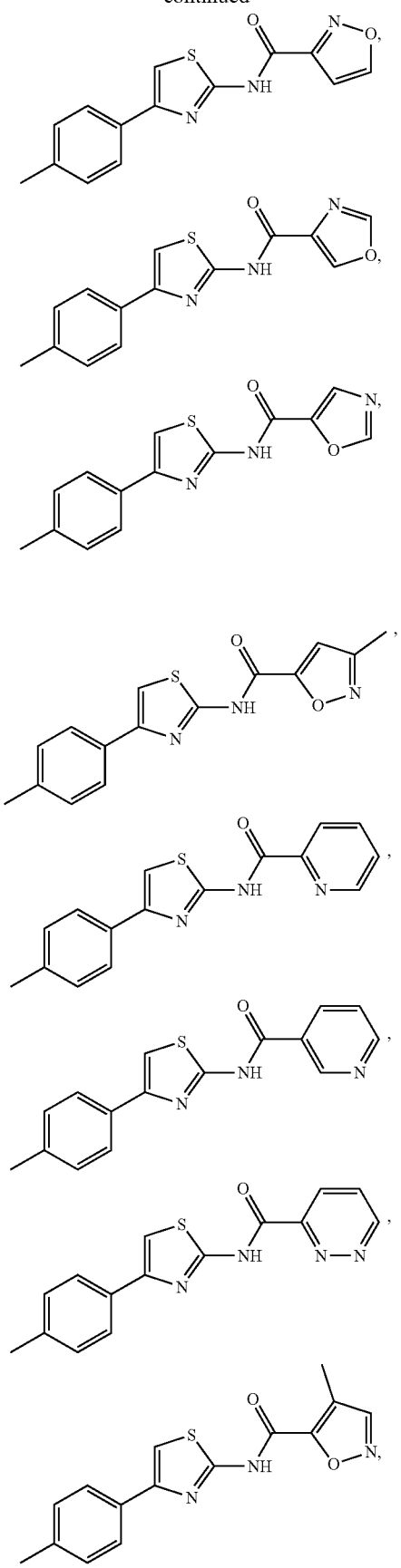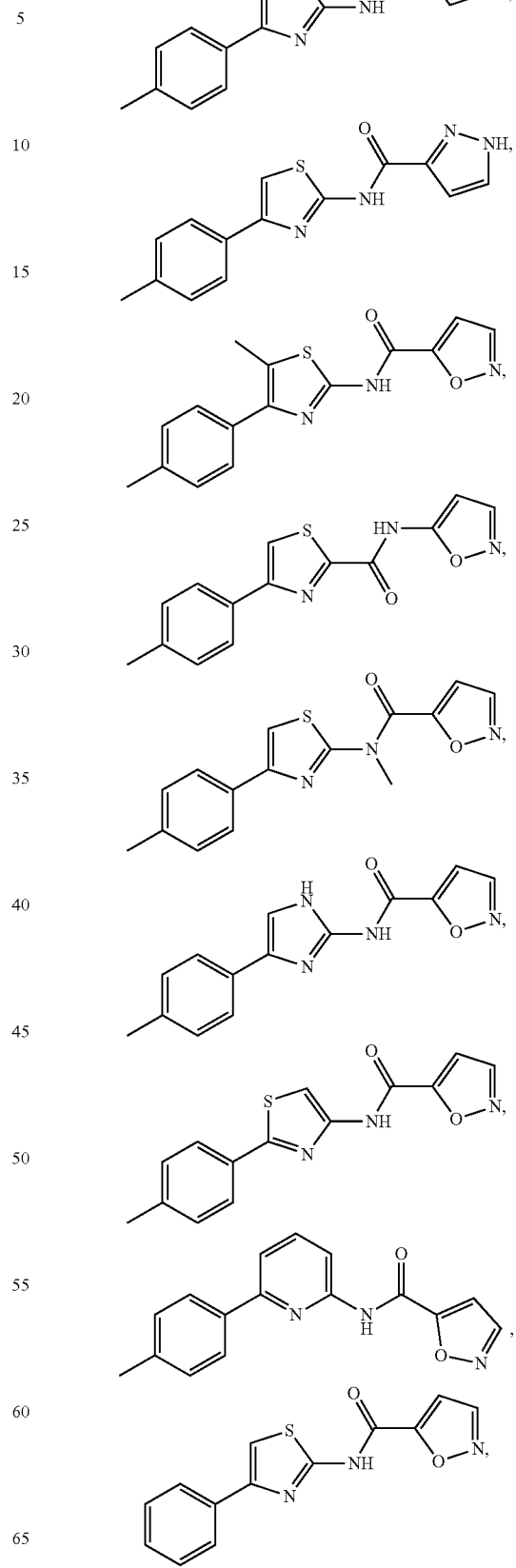

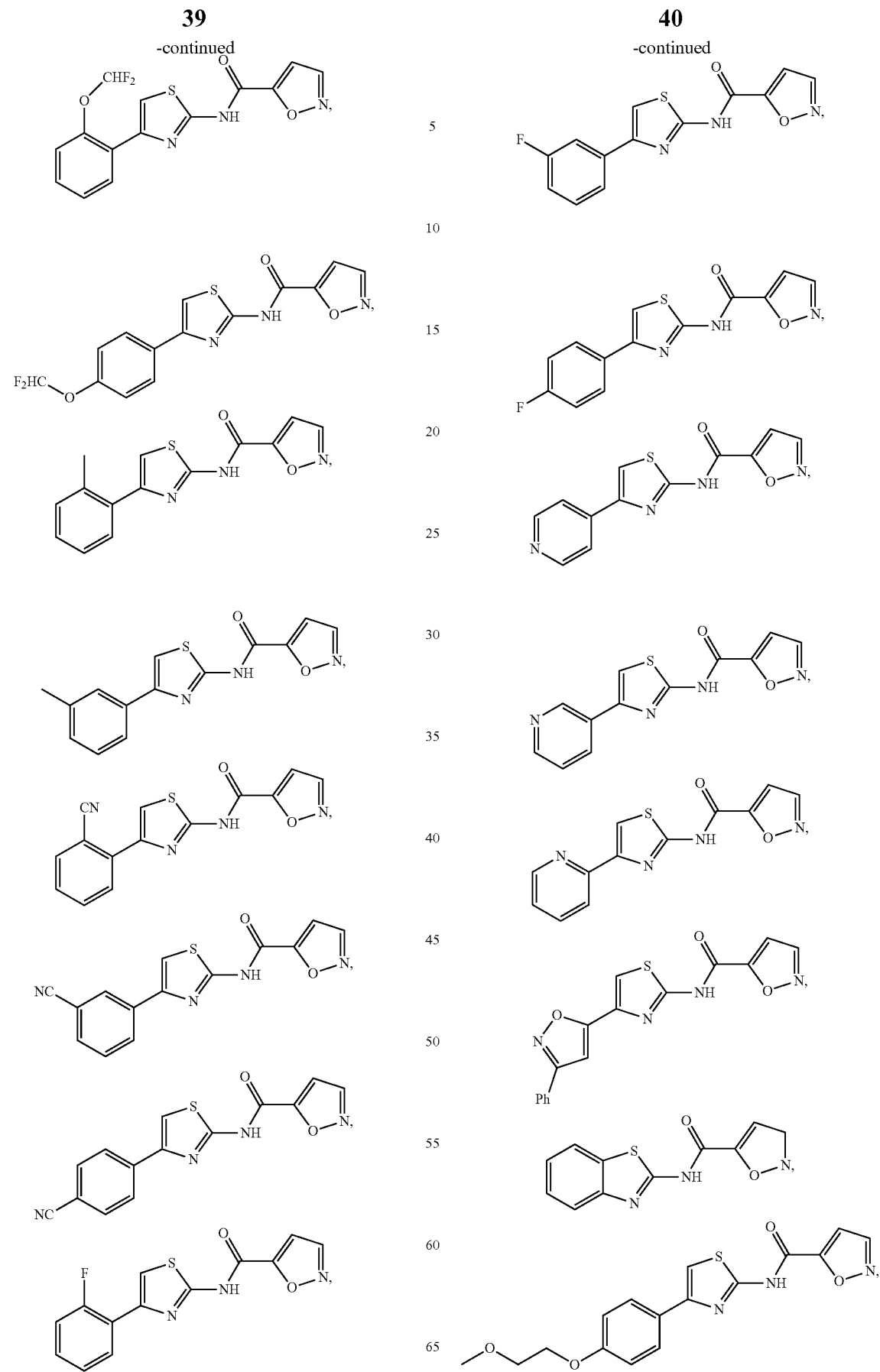

41
-continued
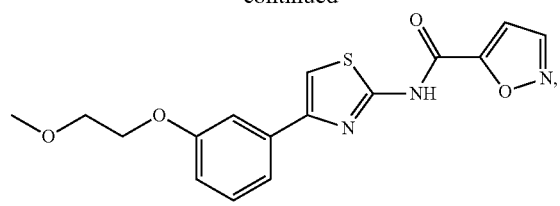
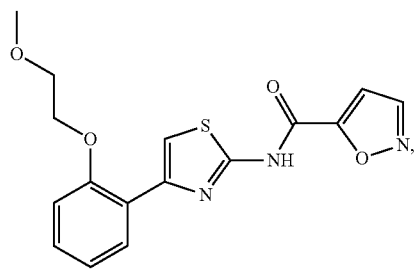
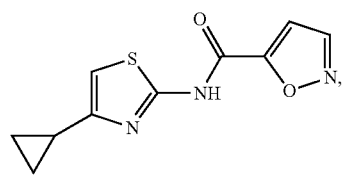
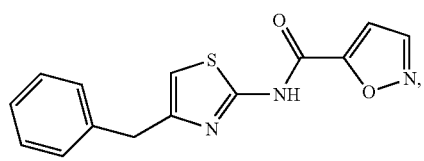
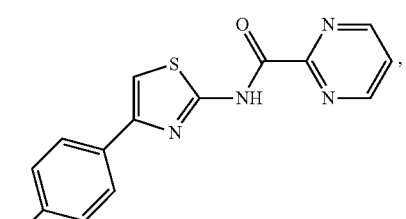
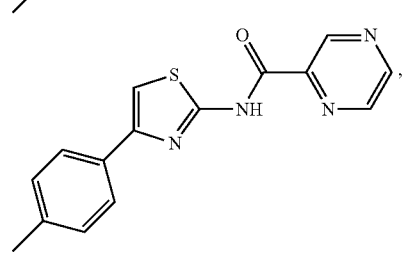
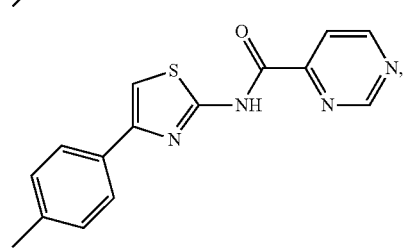
42
-continued
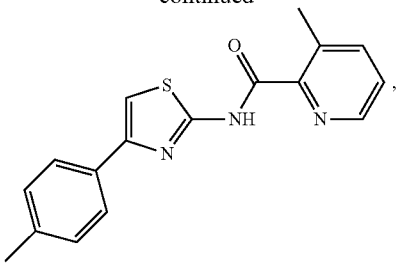
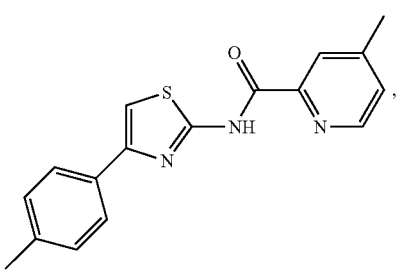
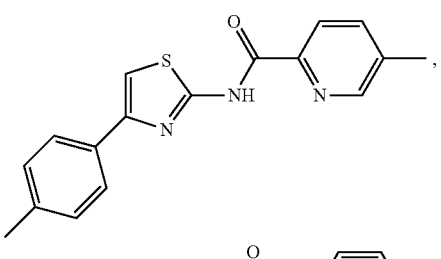
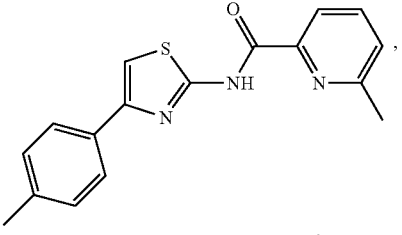
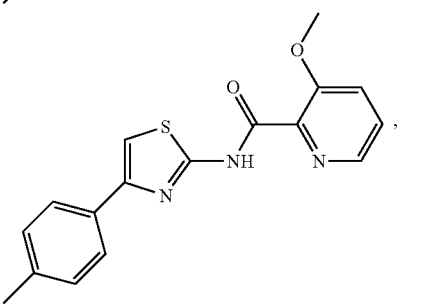
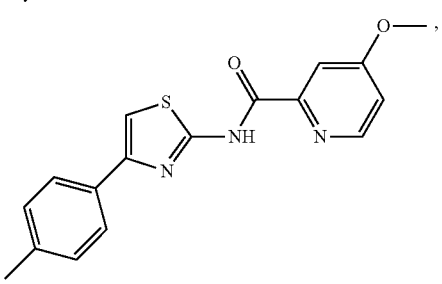

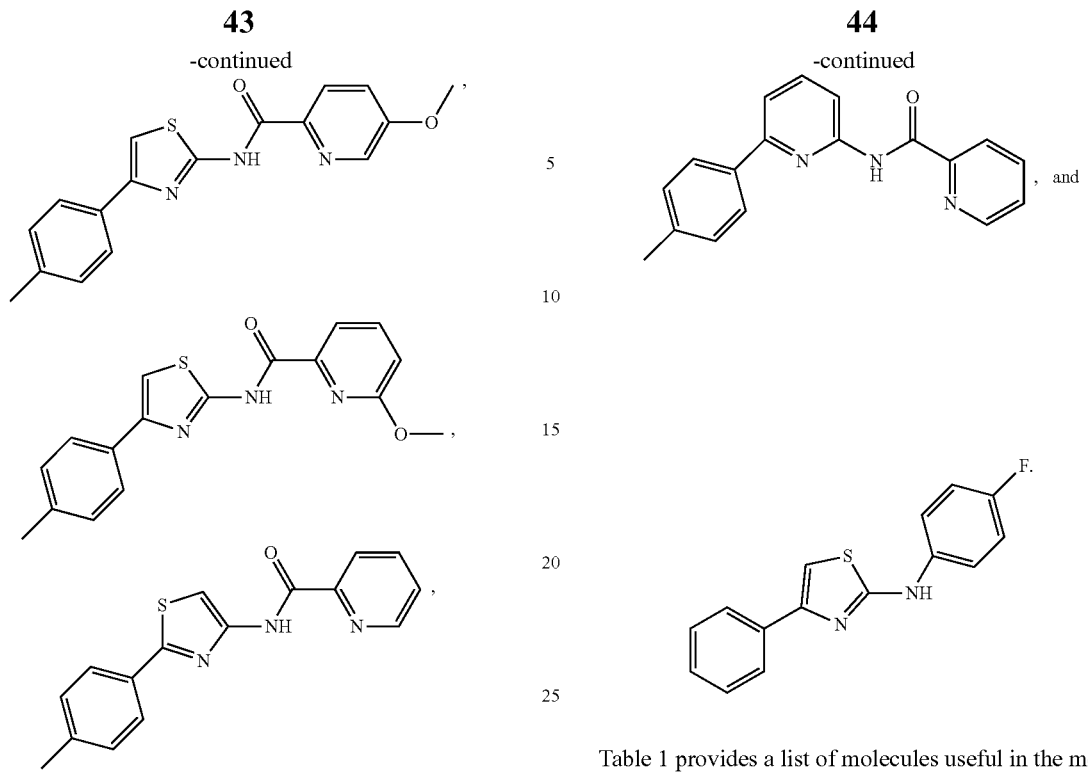
Table 1 provides a list of molecules useful in the methods and compositions of the disclosure.
TABLE 1
| COMPOUND/MOLECULE | NAME | MW | % purity |
|---|---|---|---|
| (structure) $C_{14}H_{11}N_3O_2S$ | B8 | 285.32 | 99.1 |
| (structure) $C_{15}H_{11}FN_2S$ | 423F | 270.33 | 99.5 |
| (structure) $C_{14}H_{11}N_3O_2S$ | B801 | 285.32 | 99.4 |

TABLE 1-continued
| COMPOUND/MOLECULE | NAME | MW | % purity |
|---|---|---|---|
| 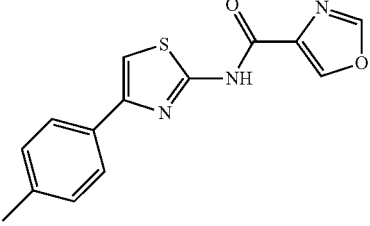<br>$C_{14}H_{11}N_3O_2S$ | B802 | 285.32 | 98.7 |
| 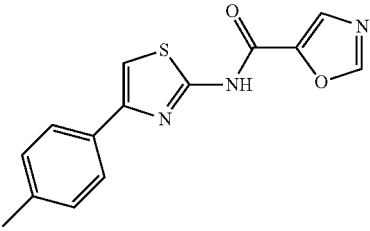<br>$C_{14}H_{11}N_3O_2S$ | B803 | 285.32 | 99.5 |
| 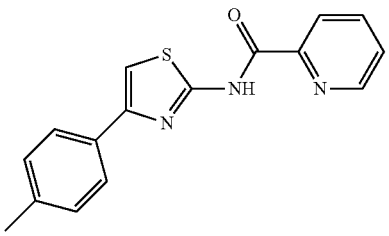<br>$C_{15}H_{13}N_3O_2S$ | B804 | 299.35 | 99.2 |
| 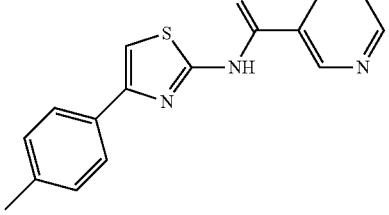<br>$C_{16}H_{13}N_3OS$ | B805 | 295.36 | 99.5 |
| <br>$C_{16}H_{13}N_3OS$ | B806 | 295.36 | 95.6 |

TABLE 1-continued
| COMPOUND/MOLECULE | NAME | MW | % purity |
|---|---|---|---|
| 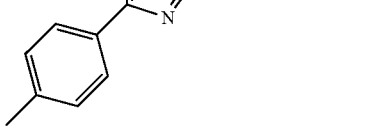<br>$C_{14}H_{12}N_4OS$ | B807 | 284.34 | 99.7 |
| 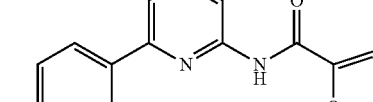<br>$C_{15}H_{13}N_3O_2S$ | B808 | 299.35 | 99.5 |
| 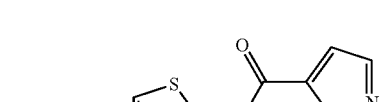<br>$C_{14}H_{11}N_3O_2S$ | B809 | 285.32 | 98.9 |
| <br>$C_{16}H_{13}N_3O_2$ | B810 | 279.3 | 99.5 |
| 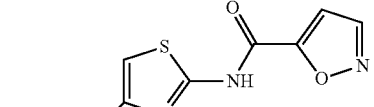<br>$C_{15}H_{13}N_3O_2S$ | B811 | 299.35 | 97.9 |
| 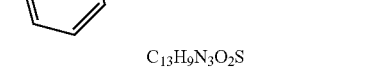<br>$C_{13}H_9N_3O_2S$ | B812 | 271.29 | 96.8 |

TABLE 1-continued

| COMPOUND/MOLECULE | NAME | MW | % purity |
|---|---|---|---|
| $C_{14}H_9F_2N_3O_3S$ (2-OCHF$_2$ phenyl isomer) | B813 | 337.30 | 99.5 |
| $C_{14}H_9F_2N_3O_3S$ (4-OCHF$_2$ phenyl isomer) | B814 | 337.30 | 99.5 |
| $C_{14}H_{11}N_3O_2S$ (2-methylphenyl) | B815 | 285.32 | 99.3 |
| $C_{14}H_8N_4O_2S$ (3-cyanophenyl) | B816 | 296.30 | 99.5 |
| $C_{14}H_8N_4O_2S$ (4-cyanophenyl) | B817 | 296.30 | 98.6 |
| $C_{13}H_8FN_3O_2S$ (2-fluorophenyl) | B818 | 289.28 | 98.9 |

TABLE 1-continued
| COMPOUND/MOLECULE | NAME | MW | % purity |
|---|---|---|---|
| 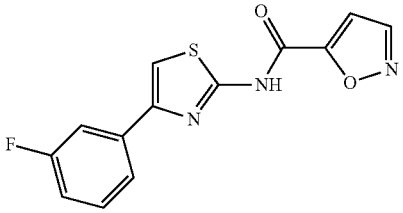 C₁₃H₈FN₃O₂S | B819 | 289.28 | 98.7 |
| 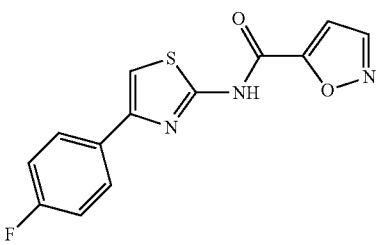 C₁₃H₈FN₃O₂S | B820 | 289.28 | 99.5 |
| 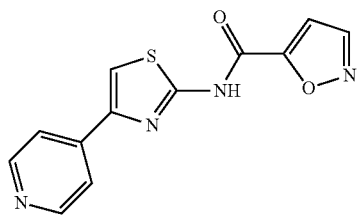 C₁₂H₈N₄O₂S | B821 | 272.28 | 96.5 |
| 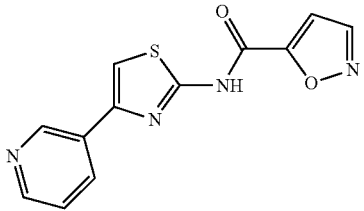 C₁₂H₈N₄O₂S | B822 | 272.28 | 99.8 |
| 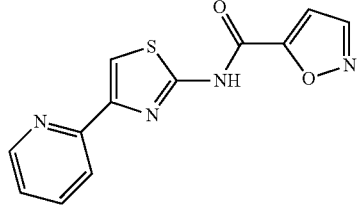 C₁₂H₈N₄O₂S | B823 | 272.28 | 95.3 |
| 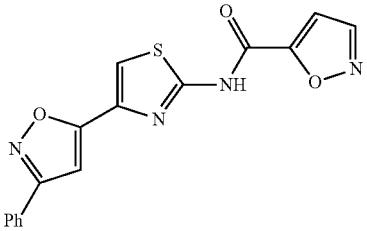 C₁₆H₁₀N₄O₃S | B824 | 338.34 | 99.2 |

TABLE 1-continued

| COMPOUND/MOLECULE | NAME | MW | % purity |
|---|---|---|---|
| C₁₁H₇N₃O₂S (benzothiazole-isoxazole carboxamide) | B825 | 245.26 | 99.5 |
| C₁₀H₉N₃O₂S (4-cyclopropyl-thiazole-isoxazole carboxamide) | B826 | 235.26 | 99.5 |
| C₁₄H₁₁N₃O₂S (4-(m-tolyl)thiazole-isoxazole carboxamide) | B827 | 285.32 | 99.0 |
| C₁₆H₁₅N₃O₄S (4-(4-(2-methoxyethoxy)phenyl)thiazole-isoxazole carboxamide) | B828 | 345.37 | 99.5 |
| C₁₆H₁₅N₃O₄S (4-(3-(2-methoxyethoxy)phenyl)thiazole-isoxazole carboxamide) | B829 | 345.37 | 99.5 |
| C₁₅H₁₂N₄OS (4-(p-tolyl)thiazole-pyrazine carboxamide) | B830 | 296.35 | 99.1 |

TABLE 1-continued

| COMPOUND/MOLECULE | NAME | MW | % purity |
|---|---|---|---|
| C₁₅H₁₂N₄OS | B831 | 296.35 | 98.8 |
| C₁₇H₁₅N₃OS | B832 | 309.39 | 99.1 |
| C₁₇H₁₅N₃OS | B833 | 309.39 | 98.3 |
| C₁₇H₁₅N₃OS | B834 | 309.39 | 96.0 |
| C₁₇H₁₅N₃O₂S | B835 | 325.39 | 97.9 |

TABLE 1-continued
| COMPOUND/MOLECULE | NAME | MW | % purity |
|---|---|---|---|
| 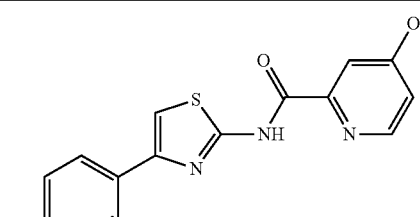<br>$C_{17}H_{15}N_3O_2S$ | B836 | 325.39 | 95.0 |
| 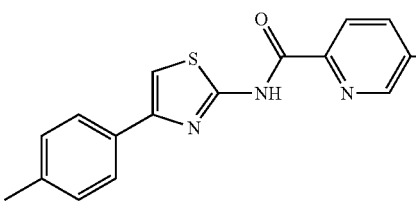<br>$C_{17}H_{15}N_3O_2S$ | B837 | 325.39 | 98.8 |
| 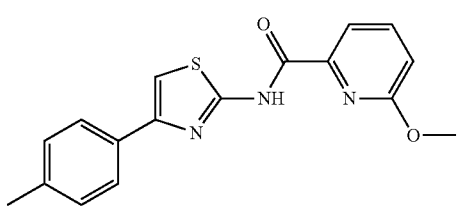<br>$C_{17}H_{15}N_3O_2S$ | B838 | 325.39 | 99.4 |
| 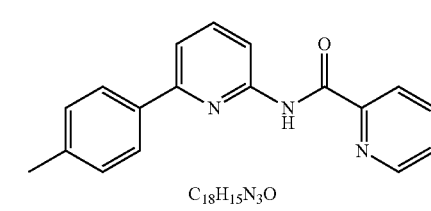<br>$C_{18}H_{15}N_3O$ | B839 | 289.34 | 99.5 |
| 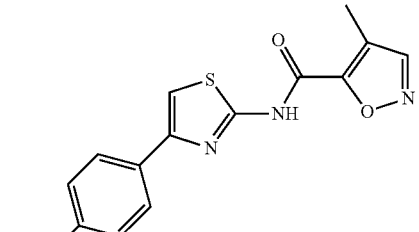<br>$C_{15}H_{13}N_3O_2S$ | B840 | 299.35 | |
| 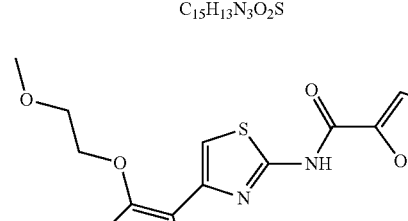<br>$C_{16}H_{15}N_3O_4S$ | B841 | 345.37 | |

TABLE 1-continued
| COMPOUND/MOLECULE | NAME | MW | % purity |
|---|---|---|---|
| 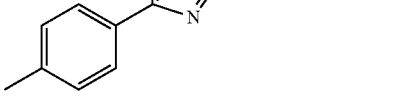 C$_{17}$H$_{15}$N$_3$OS | B842 | 309.39 | |
| 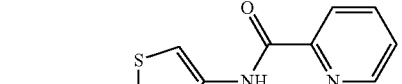 C$_{16}$H$_{13}$N$_3$OS | B843 | 295.36 | |
| 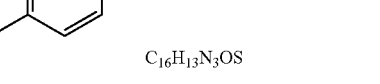 C$_{18}$H$_{17}$N$_3$O$_3$S | B844 | 355.41 | |
| 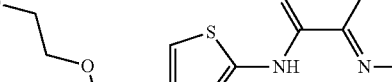 C$_{16}$H$_{13}$N$_3$OS | B845 | 295.36 | |
| 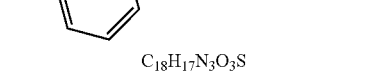 C$_{14}$H$_{11}$N$_3$O$_2$S | B846 | 285.32 | |
| 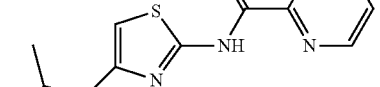 C$_{11}$H$_{13}$N$_3$O$_2$S | B847 | 251.3 | |

TABLE 1-continued

| COMPOUND/MOLECULE | NAME | MW | % purity |
|---|---|---|---|
| ![B848 structure] C₁₃H₁₅N₃OS | B848 | 261.34 | |
| ![B849 structure] C₁₆H₁₃N₃O₂ | B849 | 279.3 | |

CX-011 (B8) having the structure:

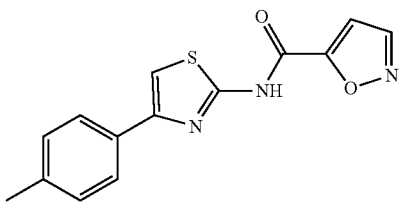 [SMILES: Cc1ccc(-c2csc(NC(=O)c3ccno3)n2)cc1]

is predicted to bind gp130 in the same binding pocket as RCGD 423, and it is hypothesized that it stabilizes an inactive conformation. The in vitro results, suggest a small molecule inhibitor of pro-inflammatory, pro-degenerative signaling mediated by IL-6 family cytokines through gp130 would have great clinical importance. Although a biologic against IL-6R is currently being tested as a therapeutic against OA, this therapy does not block the effects of oncostatin M (OSM) and LIF, two other IL-6 family members with pro-catabolic consequences on articular cartilage. Thus, small molecule gp130 inhibitor such as CX-011 (B8) and analogs thereof are useful for post-traumatic OA and have a different method of action. It is hypothesized that broad inhibition of IL-6 family cytokine signaling will interrupt the pro-inflammatory, pro-degenerative environment present post-injury. In the experiments described herein and below, the half-maximal inhibitory concentration (IC$_{50}$) of CX-011 (B8) on gp130 in rat, dog and human articular chondrocytes in the presence of IL-6 and OSM are examined. The anti-degenerative effects of CX-011 (B8) in two rat models of OA, focusing on proteoglycan loss, the levels of pro-catabolic enzymes and proliferation are examined. Together, the results demonstrate the fitness of CX-011 (B8) and analogs thereof to progress as a potential therapeutic candidate to combat OA.

The disclosure provides methods of treating inflammatory disorders, neoplasms, and cell proliferative disorders comprising contacting a subject or cell with any of the foregoing compounds. In other embodiments, the disclosure provides methods of modulating the production or induction of inflammation and/or inflammatory cytokines comprising contacting a cell or subject with a compound as described herein. In certain embodiments, the cell is a chondrocyte.

The invention is illustrated in the following examples, which are provided by way of illustration and are not intended to be limiting.

EXAMPLE

Figure 2A:
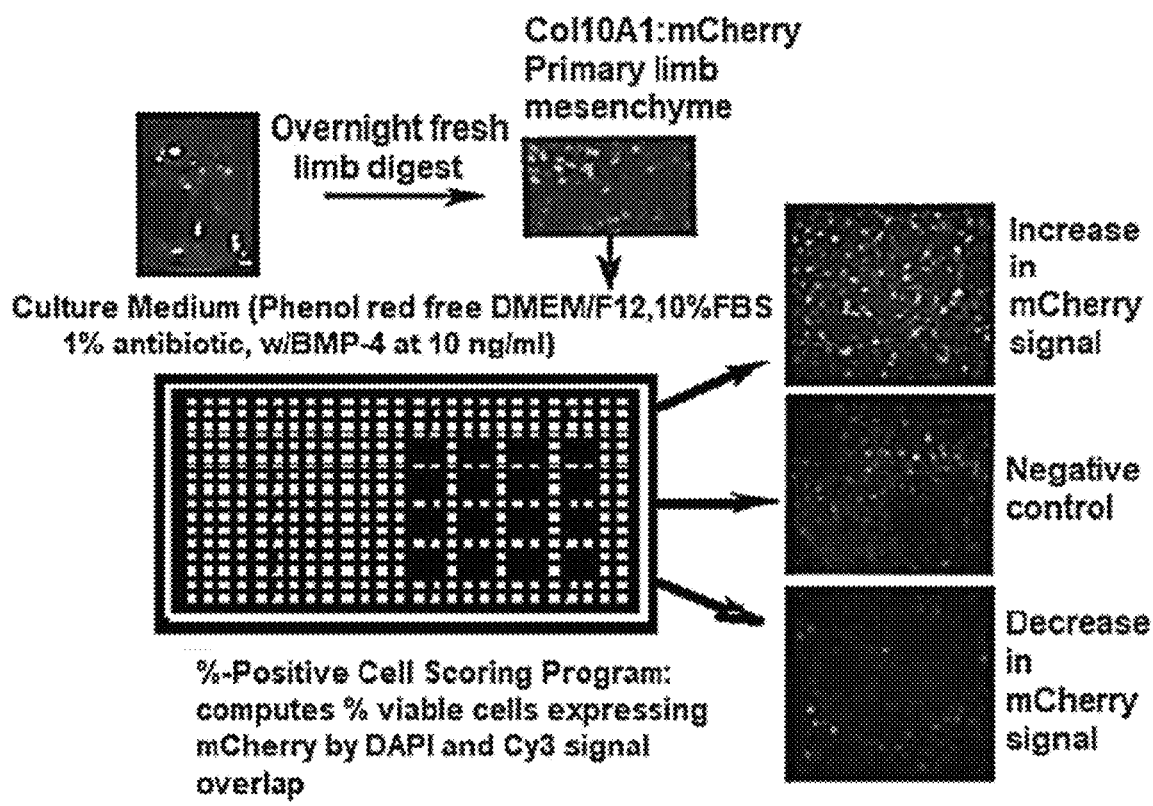
FIG. 2A-D shows (A) A screen of the ability of 170,000 compounds to inhibit a Col10a1-RFP reporter in limb bud mesenchymal cells identified RCGD 423 (B-C). The ability of the compound to inhibit hypertrophy was confirmed on human fetal articular chondrocytes (D).
Figure 2B:
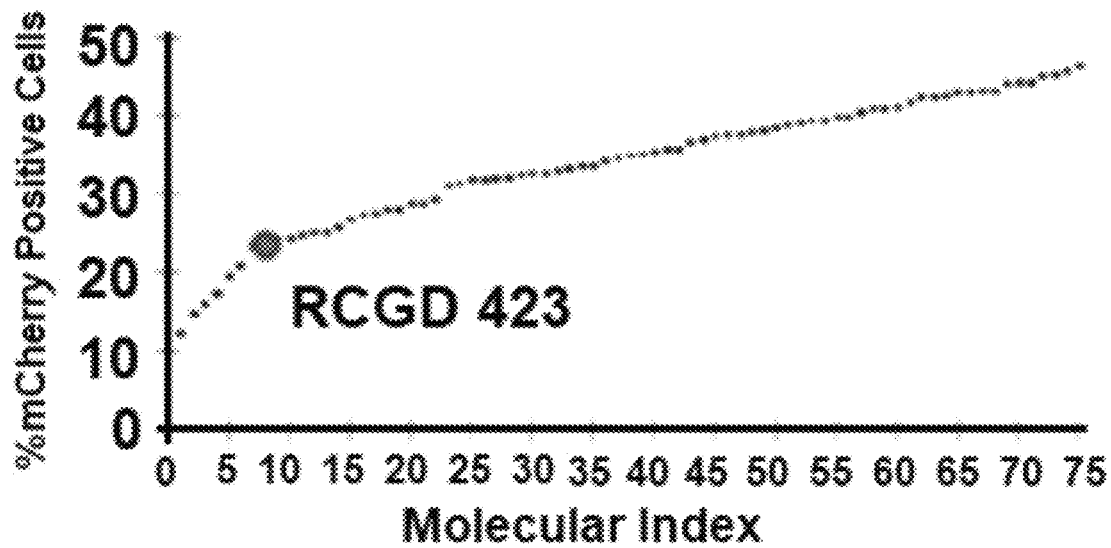
Figure 2C:
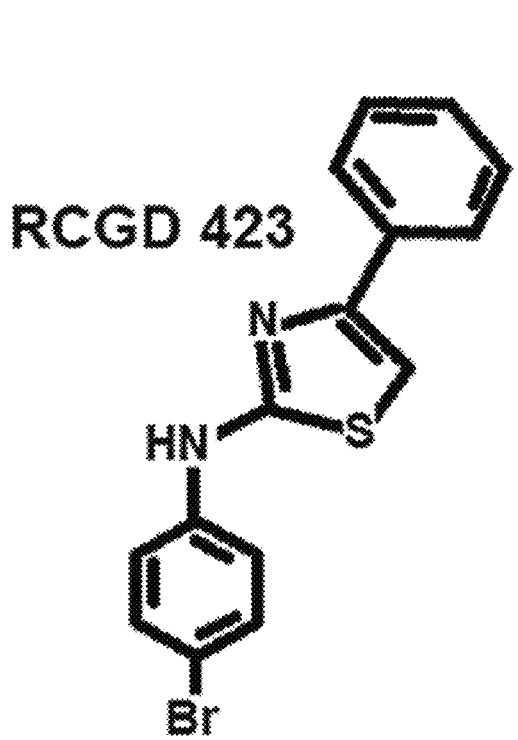
Figure 2D:
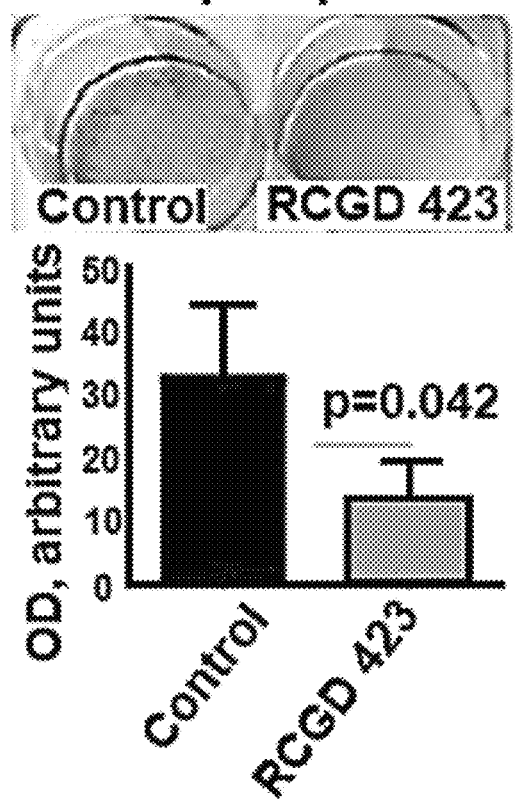

The gp130 co-receptor LIFR is expressed on a subset of superficial chondrocytes throughout human ontogeny. Based on these data, it is hypothesized that gp130 would also be expressed on these cells, and this was indeed the case (FIG. 1). Given the known (and mostly detrimental roles) of IL-6 family cytokines on articular chondrocytes, a high throughput screen was performed to identify small molecules that could potentially modulate gp130 signaling. In adult mice, IL-6/gp130 signaling drives Col10a1 expression and hypertrophy, which has been strongly associated with OA progression; ~170,000 compounds were thus screened for their ability to prevent increases in Col10-mCherry fluorescence in mouse limb mesenchymal cells stimulated with BMP-4, a strong driver of hypertrophy (FIG. 2). One primary hit, RCGD 423, emerged after secondary screening as it could prevent increases in alkaline phosphatase, a marker of hypertrophy, in fetal articular chondrocytes (FIG. 2D).

Figure 3:
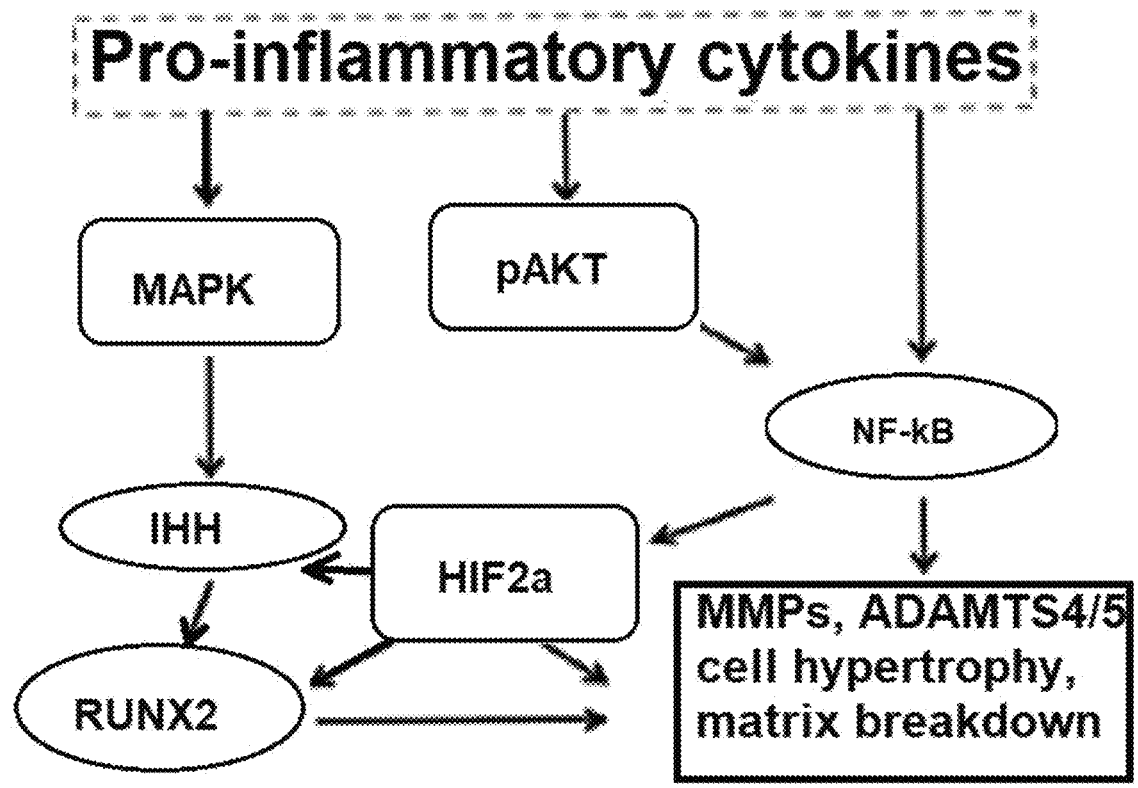
FIG. 3 shows a schematic of molecular and functional outcomes downstream of pro-inflammatory cytokines.
Figure 4A:
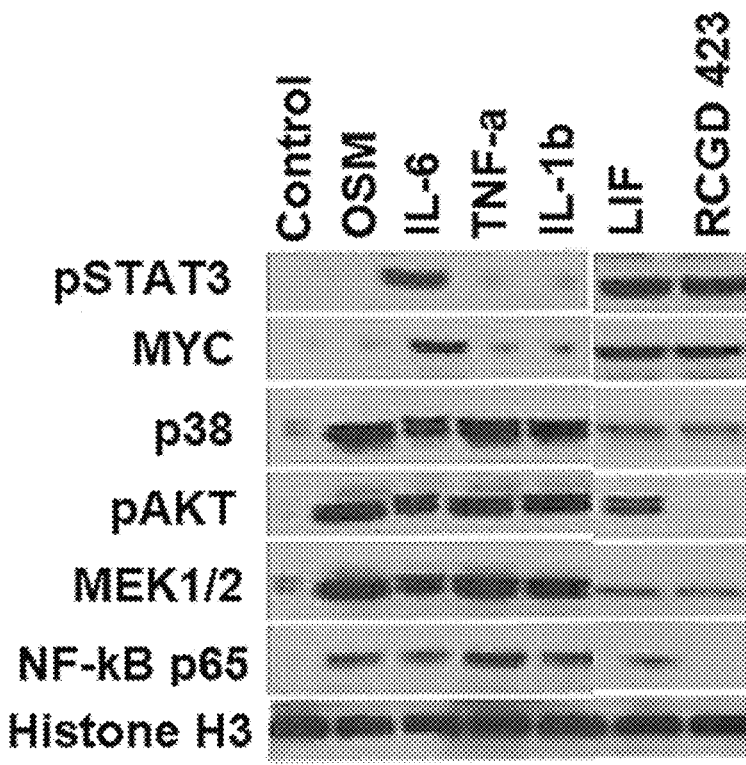
FIG. 4A-B shows IL-6 family cytokines activate the MAPK, AKT and NF-κB pathways in adult pig articular chondrocytes; RCGD 423 does not, despite shared increase in active STAT3 (pSTAT3) and MYC proteins.
Figure 4B:
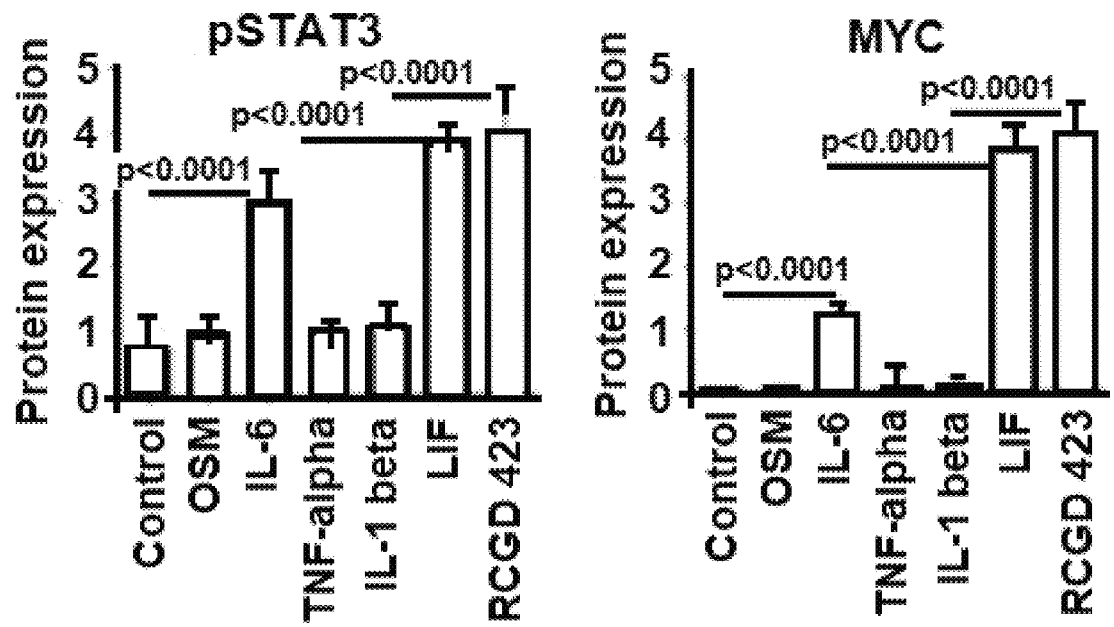
Figure 5A:
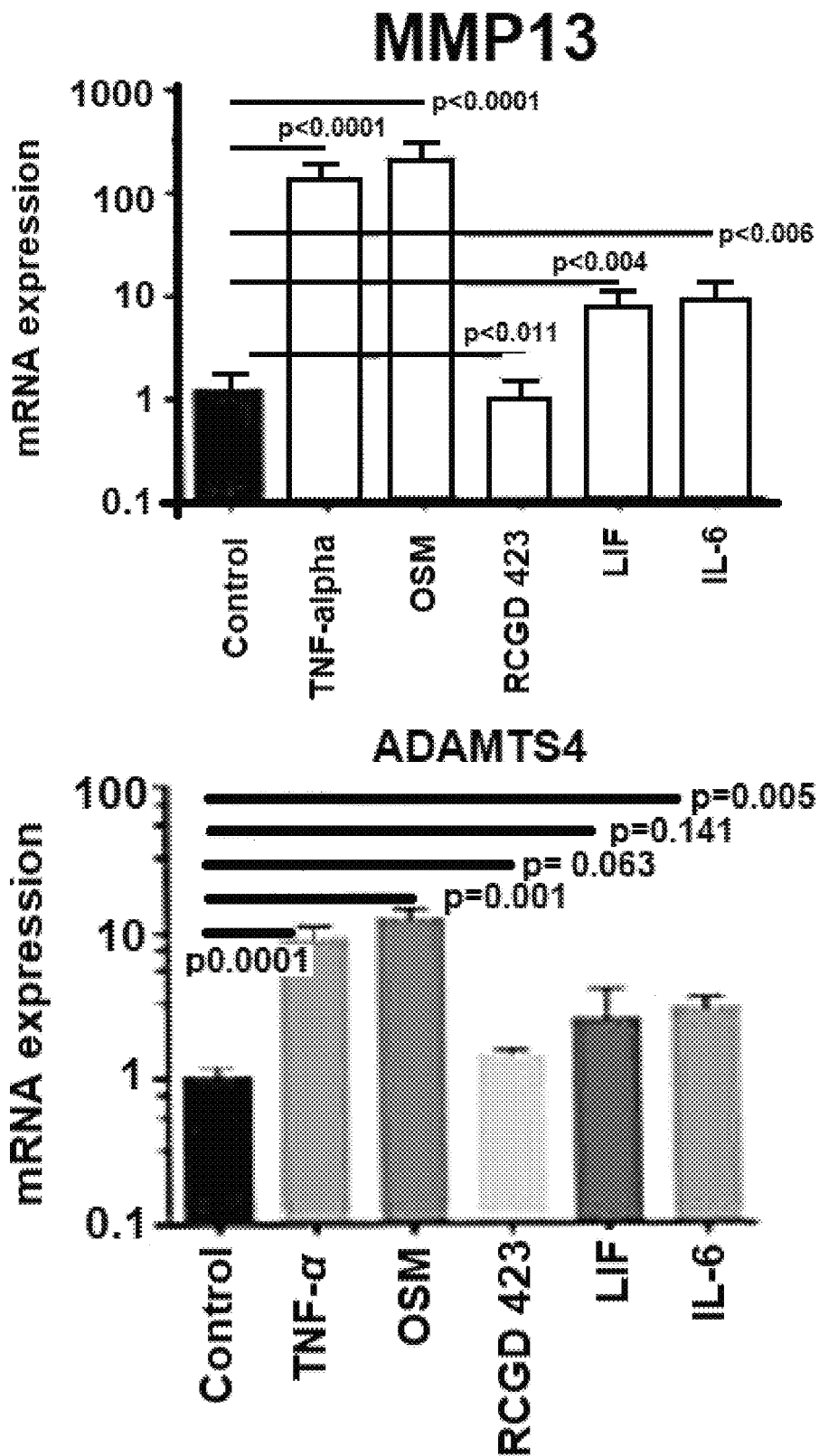
FIG. 5A-B shows (A) IL-6 family cytokines increase the expression of proteolytic enzymes while RCGD 423 does not. (B) Accumulation of pSTAT3 and MYC proteins induced by RCGD 423 can be blocked by chemical inhibition of JAK or gp130 proteins.
Figure 5A:
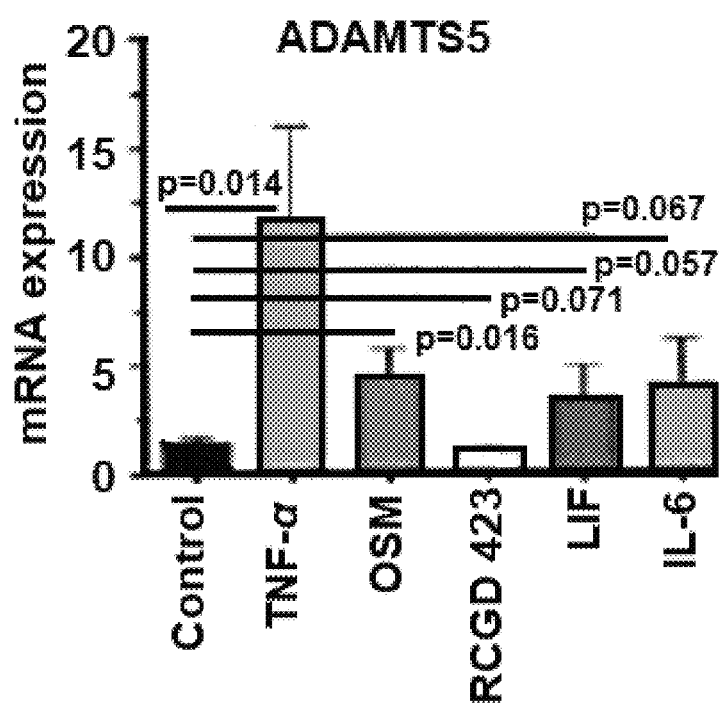
Figure 5B:
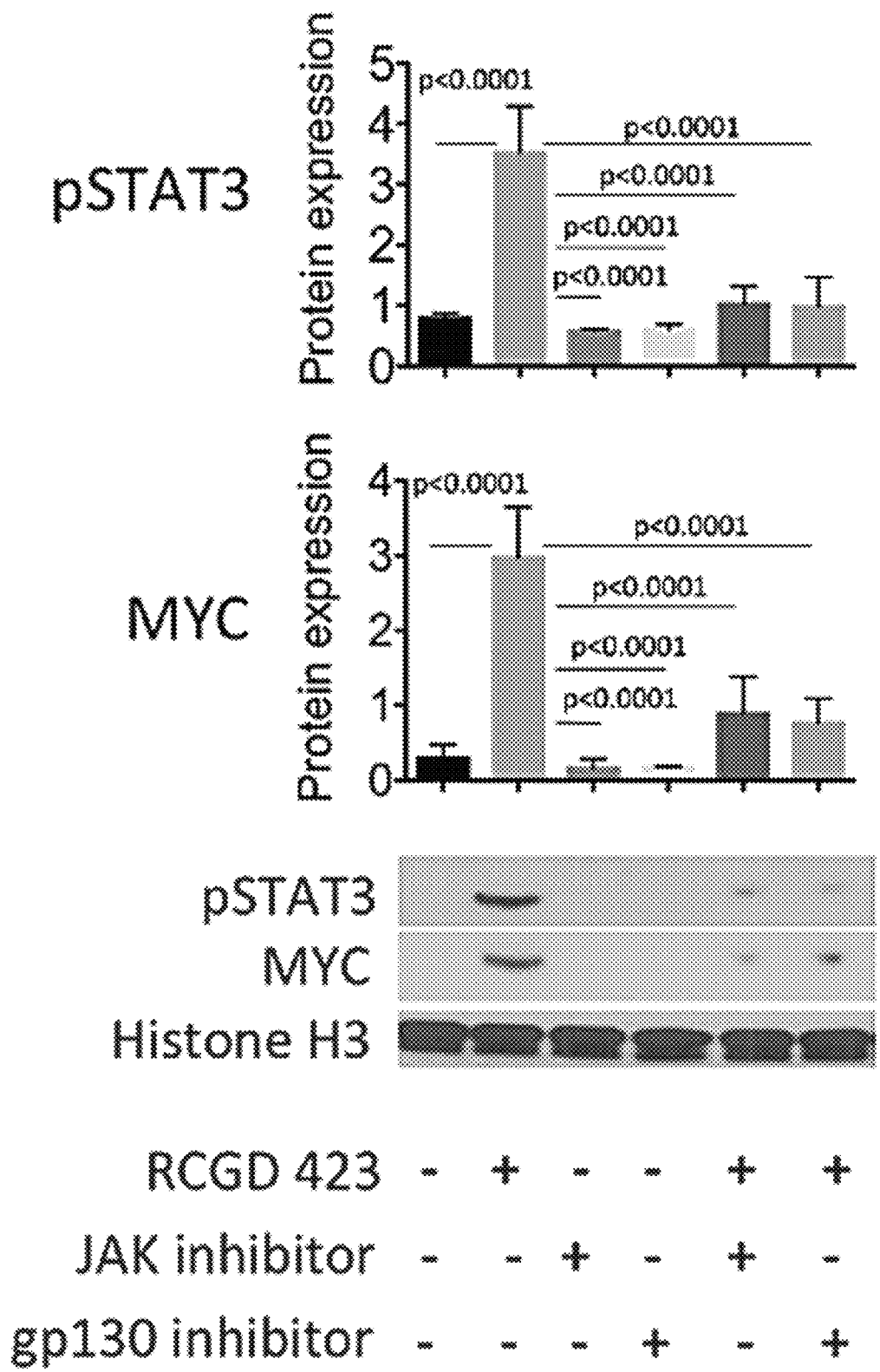
Figure 6:
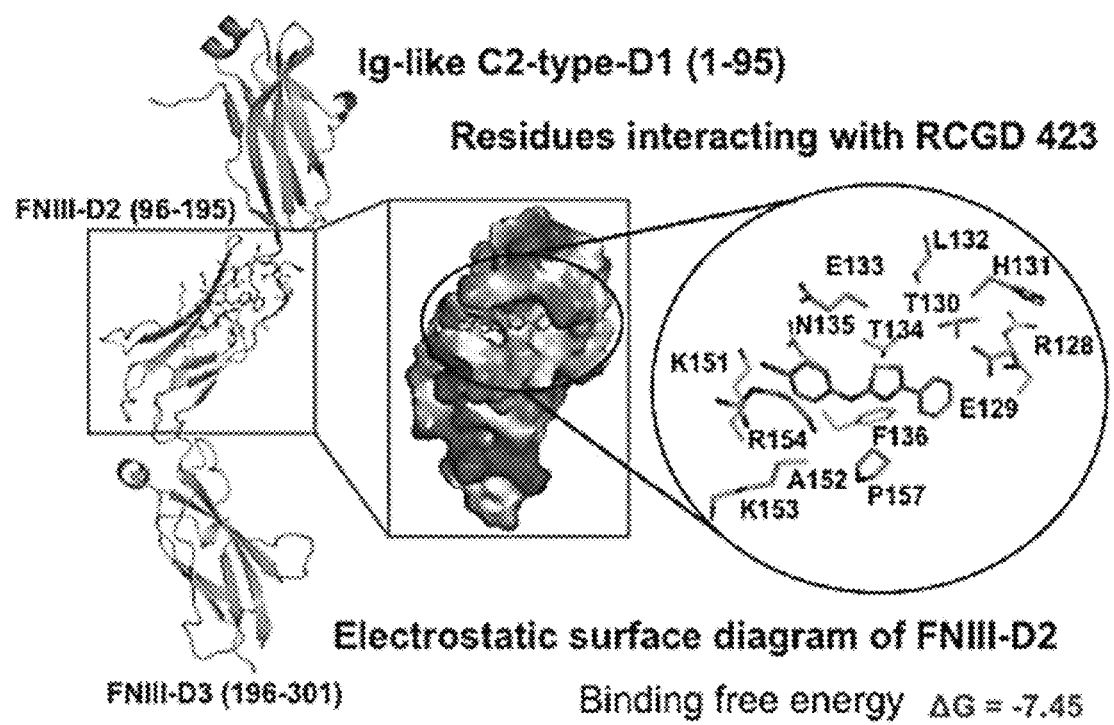
FIG. 6 shows molecular modeling of the proposed interaction between gp130 and RCGD 423. Oxygen, nitrogen; sulfur and bromine atom are shown.

To begin to address the mechanism of action of RCGD 423, adult pig chondrocytes were incubated with the drug, IL-6 family cytokines or the pro-catabolic cytokines TNF-α and IL-1β and measured levels of various proteins downstream of these cytokines that are known to drive catabolic responses (FIG. 3). These data revealed similarities among RCGD 423, IL-6 and LIF: all increased levels of active STAT3 and MYC proteins. However, while IL-6 and LIF activated the MAPK, AKT and NF-κB pathways, RCGD 423 did not evidence the same result (FIG. 4). This was confirmed by qPCR for the proteolytic enzymes ADAMTS4/5 and MMP13, which showed that most tested cytokines including LIF and IL-6 resulted in significant increases in the expression of these genes while RCGD 423 did not (FIG. 5). Based on these data, it was hypothesized that RCGD 423 interacted with gp130 to modify its signaling output. A small molecule inhibitor of gp130 prevented the accumulation pSTAT3 and MYC proteins following incubation of adult pig articular chondrocytes with RCGD 423, suggesting that the compound acts near the apex of the gp130-JAK-STAT3-MYC signaling cascade (FIG. 6). Based on these results, it was further hypothesized that RCGD 423 is a direct agonist of gp130, inducing activation in the absence of ligand.

To address this hypothesis, the interaction of RCGD 423 with the extracellular domain of gp130 was modeled using Swissdock and the results showed a putative high affinity binding site within domain 2 of gp130 (FIG. 6). Four of the main amino acids interacting with the halogenated ring of RCGD 423 (K151-R154) are of particular interest, as deletion of these residues has been shown to cause irreversible activation of gp130 signaling by promoting the formation of constitutively active homodimers, driving a gene expression response typical of high STAT3 activity. These findings show that K151-R154 are important for inhibiting inappropriate activation of gp130. Of note, another gp130 deletion mutant identified and tested demonstrated that loss of key residues in gp130 leads to unbridled gp130 signaling through non-canonical homodimers.

Figure 8:
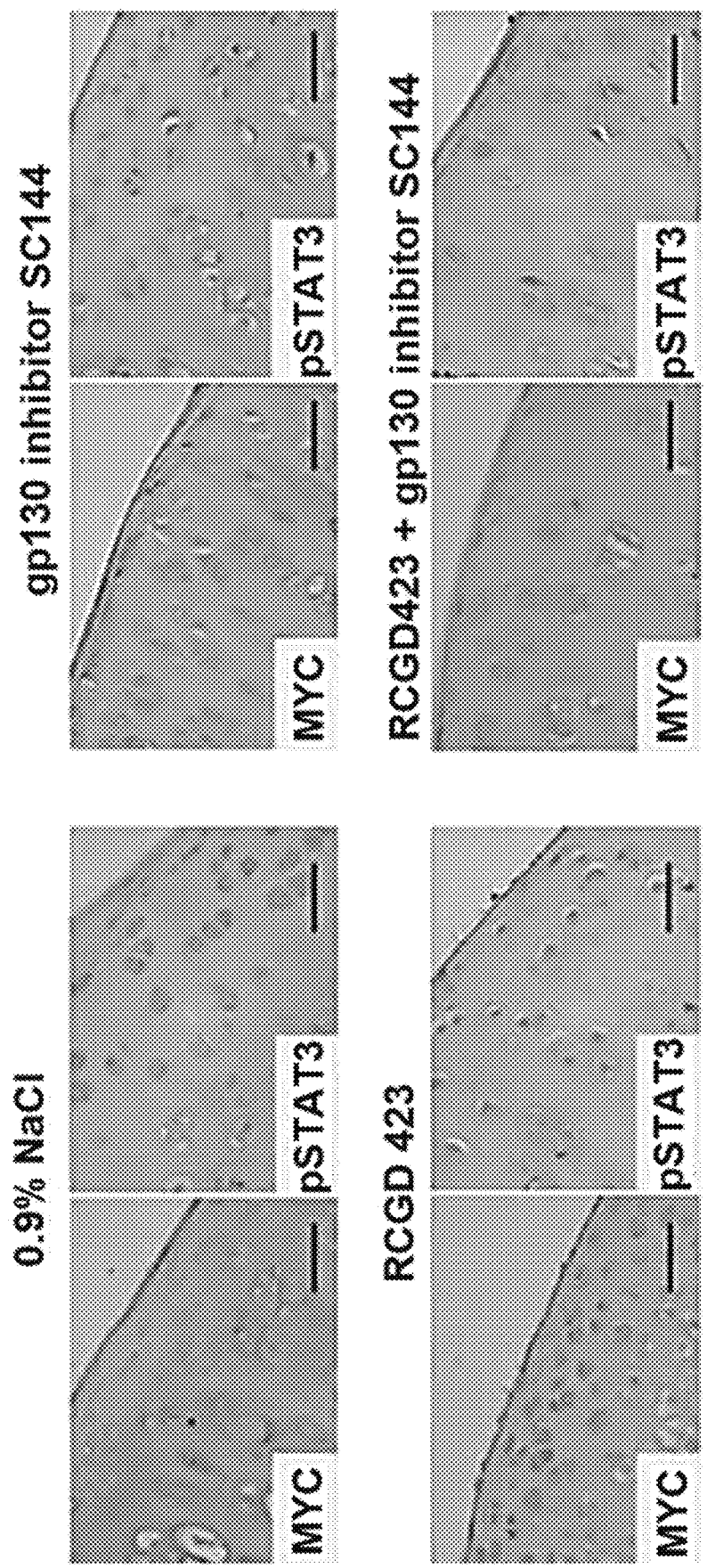
FIG. 8 shows Injection of RCGD 423 into rat joints increased pSTAT3 and MYC levels; this could be blocked by co-injection of the small molecule gp130 inhibitor SC144.
Figure 9:
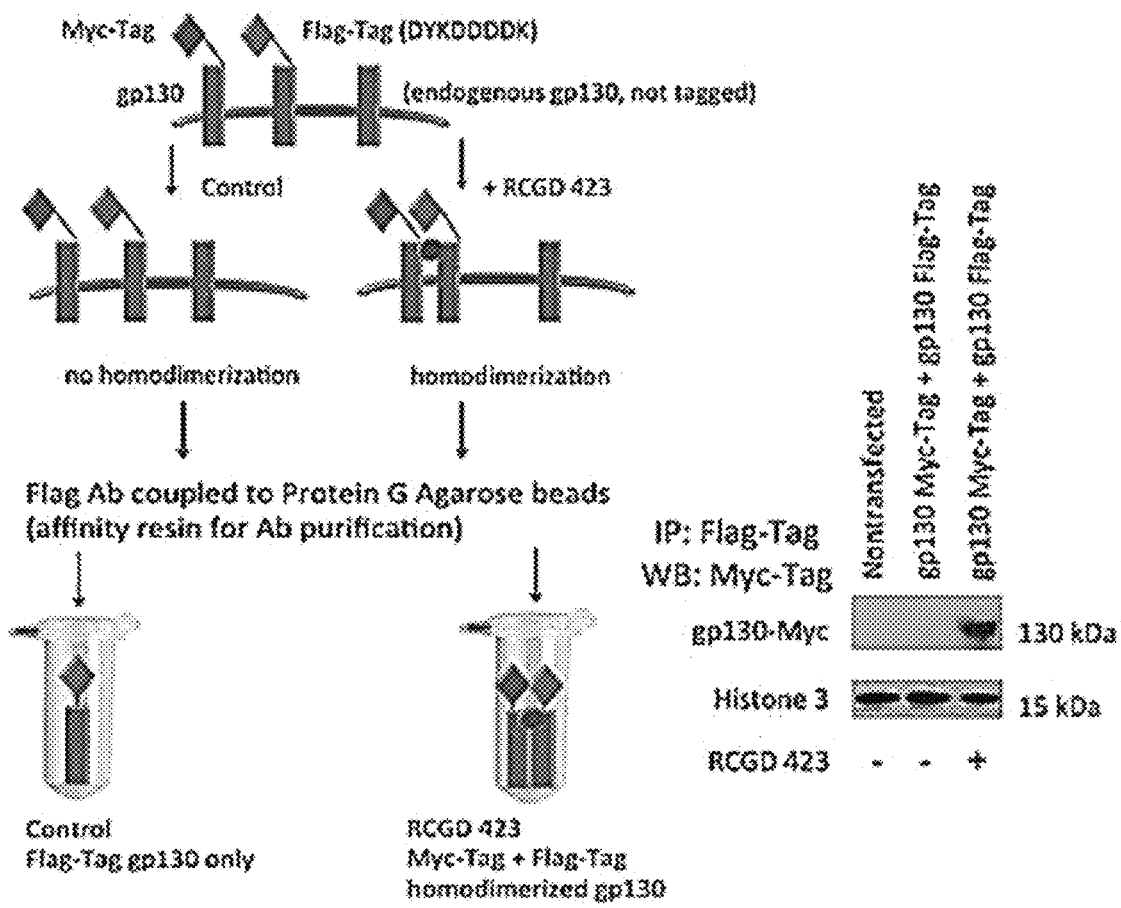
FIG. 9 shows Tagged versions of gp130 allow interrogation of hetero- vs. homodimeric signaling. gp130-Myc was only detectable in the presence of RCGD 423.

Based on this, it was hypothesized that RCGD 423 acts through gp130 by promoting stable homodimers in the absence of ligand. To confirm that RCGD 423 acts through gp130, the gp130 null cell line Ba/F3 cells was used. Ba/F3 cells were transfected with either full-length gp130 or a mutant gp130 lacking domain 2 (ΔD2), which contains the predicted binding site for RCGD 423 (FIG. 7). These data demonstrated that full-length gp130 is required for the activity of RCGD 423. To verify the specificity of RCGD 423 in vivo, the compound was injected into rat knees in the presence of the small molecule gp130 inhibitor SC144 or a blocking antibody specific for domain 2 of gp130. Inclusion of either antagonist completely inhibited signaling downstream of RCGD 423 (FIG. 8). The ability of RCGD 423 to act via inducing formation of gp130 homodimers was then examined by expressing tagged versions of gp130 in 293T cells. In this system, only homodimeric complexes can contain both tagged versions of gp130 (FIG. 9). The results demonstrated that only in the presence of RCGD 423 could gp130 homodimers be detected. Together, these results demonstrated that RCGD 423 is a direct gp130 agonist that acts by promoting formation of active gp130 homodimers in the absence of ligand.

Figure 10A:
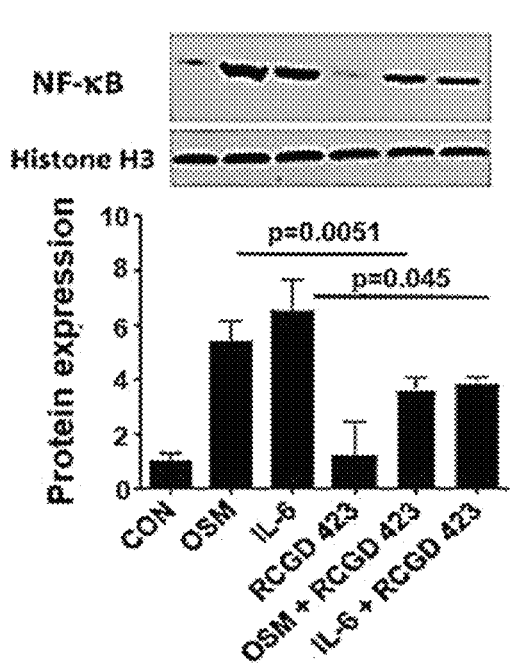
FIG. 10A-B shows RCGD 423 reduces signaling downstream of OSM and IL-6 (A) by competing for gp130 (B).
Figure 10B:
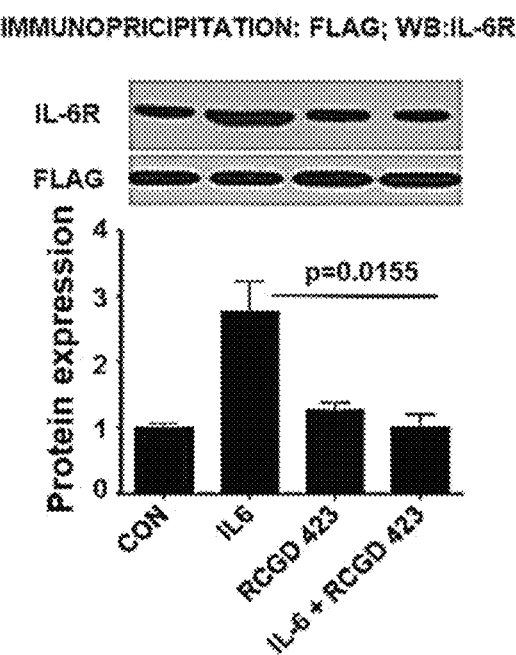
Figure 11:
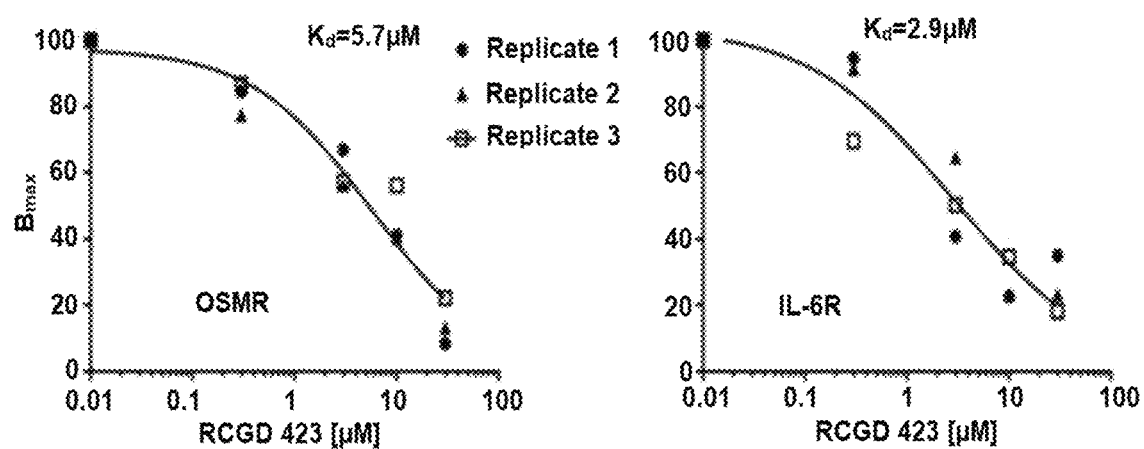
FIG. 11 shows RCGD 423 directly competes with OSMR and IL-6R for gp130 occupancy in chondrocytes. Adult human chondrocytes transfected with gp130-Flag were incubated with various concentrations of RCGD 423 in the presence of IL-6 or OSM; levels of immoprecipitated IL-6R or OSMR were used to calculate the dissociation constant ($K_d$).

Based on this mechanism of action, it was hypothesized that RCGD 423 could potentially inhibit signaling by IL-6 family cytokines due to the requirement for gp130 to interact with ligand/receptor complexes. This property would be of great interest due to the pro-inflammatory and pro-catabolic effects of these cytokines in the joint space. Incubation of human adult articular chondrocytes with RCGD 423 in combination with OSM or IL-6 significantly reduced increases in NF-κB protein, a major regulator of inflammation and catabolism (FIG. 10A). To assess whether RCGD 423 could directly compete for gp130 occupancy, human adult articular chondrocytes were transfected with tagged gp130 and then pulled down associated proteins±RCGD 423 and/or IL-6. These results demonstrated that in the presence of RCGD 423, gp130-IL-6R complexes were significantly reduced (FIG. 10B). These results were expanded to determine the dissociation constant ($K_d$), a measure of the affinity between gp130 and its binding partners OSMR and IL-6R, in the presence of RCGD 423 and either OSM (oncostatin M) or IL-6 (FIG. 11). These results demonstrated a strong ability of the compound to interfere with ligand-mediated gp130 heterodimerization. Taken together, these data identify an additional mechanism of action by which RCGD 423 could evidence disease-modifying activity.

Figure 12:
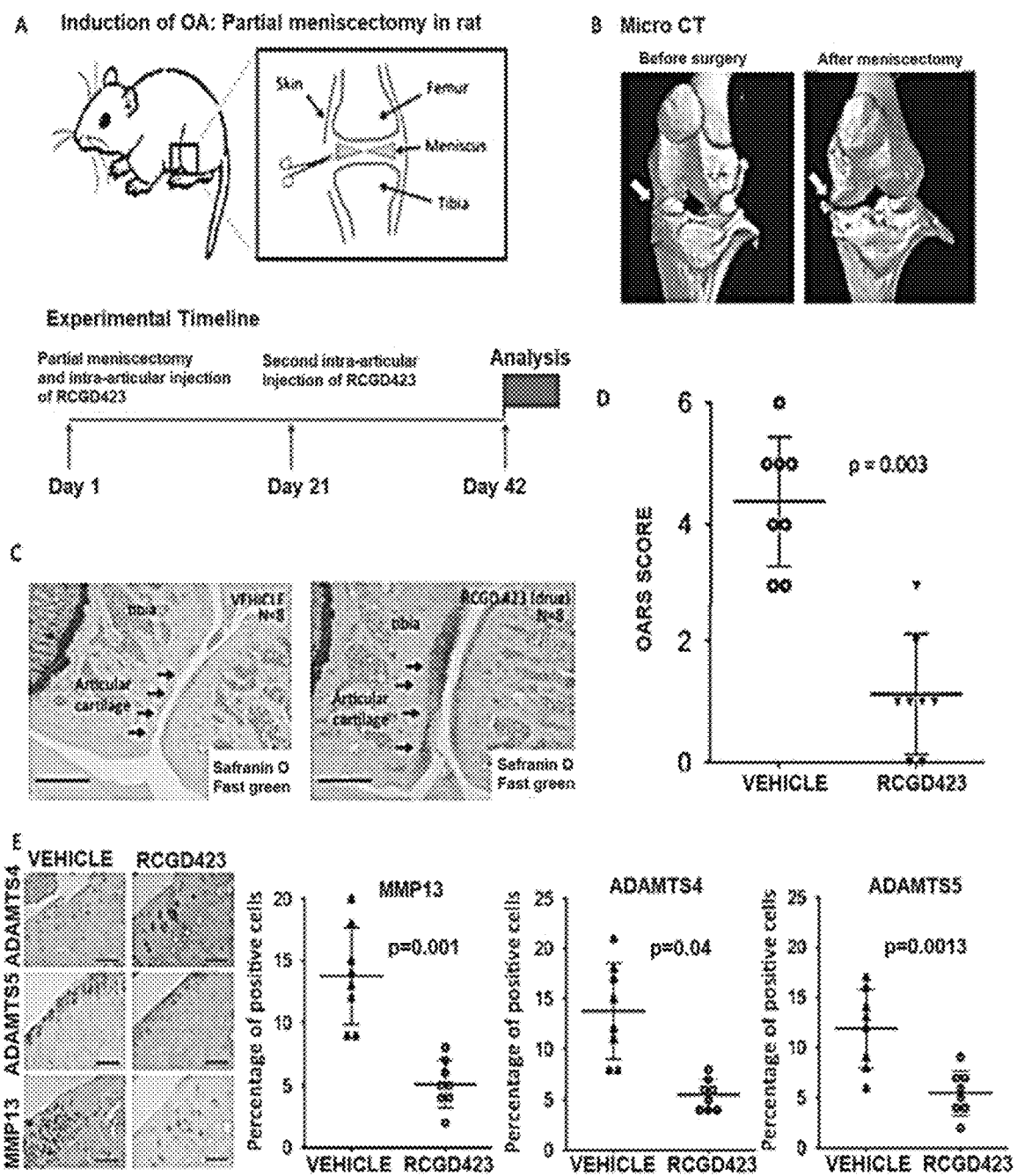
FIG. 12A-E shows A rat model of OA was validated (A and B) to assess the ability of RCGD 423 to prevent loss of Safranin O$^+$ hyaline cartilage (C) and joint degeneration (D); the drug also decreased the levels of catabolic enzymes (E).
Figure 13:
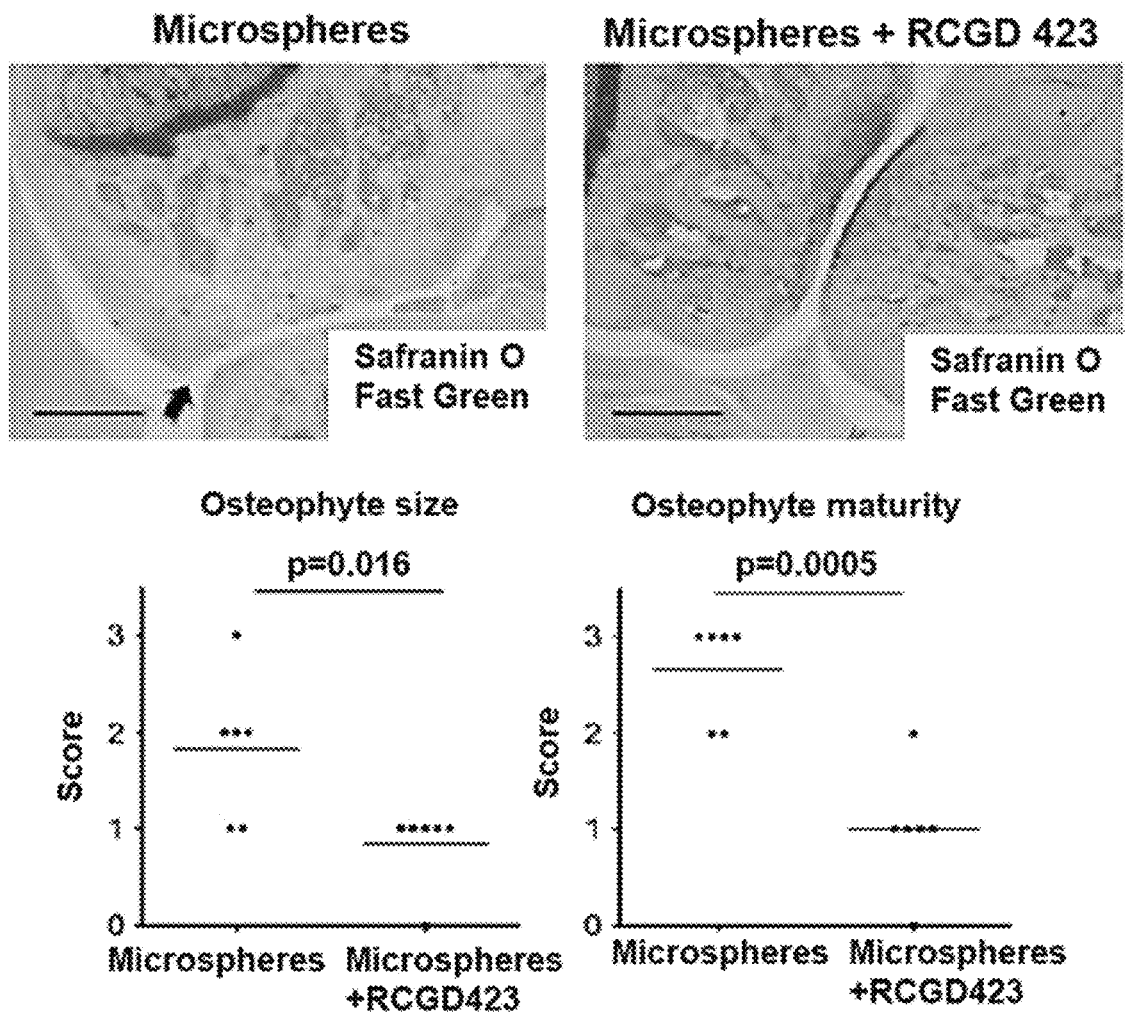
FIG. 13 shows Treatment of rats following partial menisectomy with RCGD 423 reduced the size and maturity of osteophytes (arrow).

Based on these results, it was hypothesized that RCGD 423 could evidence disease-modifying activity in a rat model of degenerative osteoarthritis. In this system, 50% of the meniscus is surgically removed, promoting joint instability similar to what is commonly observed in human OA and degeneration of articular cartilage in 3-6 weeks (FIGS. 12A and B). RCGD 423 loaded onto PLGA (poly(lactic-co-glycolic acid)) microspheres for slow release, or microspheres alone, were injected into the joint space at the time of surgery and 3 weeks later. This dosing interval was based on off-loading studies which showed continuous released of RCGD 423 from PLGA microspheres over 3-4 weeks in culture (data not shown). After 6 weeks, knees treated with RCGD 423 evidenced highly significantly lower OARSI scores, a histological measure of OA that increases with worsening cartilage loss and joint damage (FIGS. 12C and D). Moreover, RCGD 423 decreased the expression of proteolytic enzymes that promote cartilage loss following injury (FIG. 12E). In addition, the compound also inhibited both the formation and maturity of osteophytes in response to joint injury (FIG. 13). These results provide conclusive data that RCGD 423 prevents cartilage degeneration in vivo.

Figure 14A:
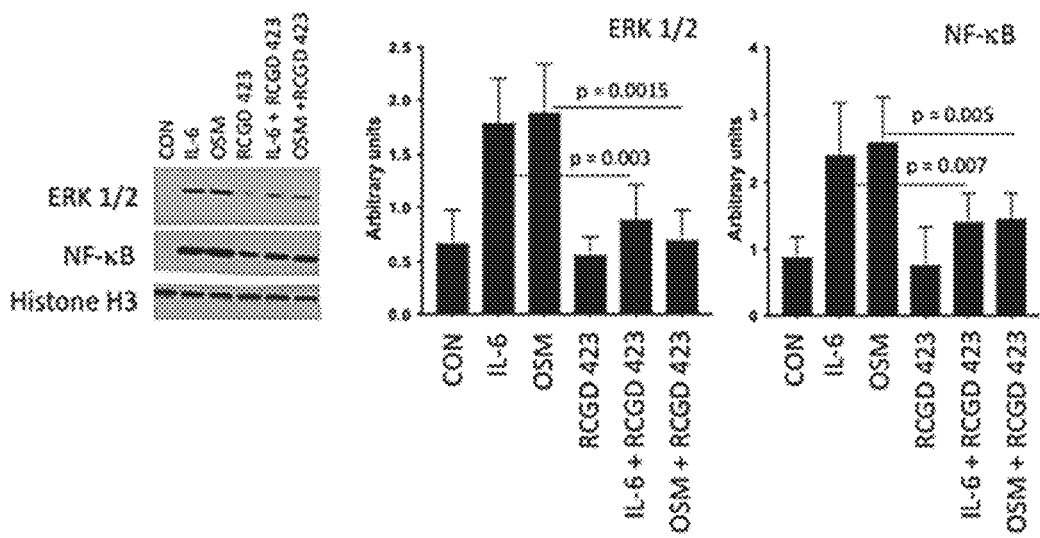
FIG. 14A-B shows RCGD 423 inhibits increases in ERK and NF-κB levels downstream of OSM and IL-6 in adult human (A) synoviocytes and (B) PBMCs.
Figure 14B:
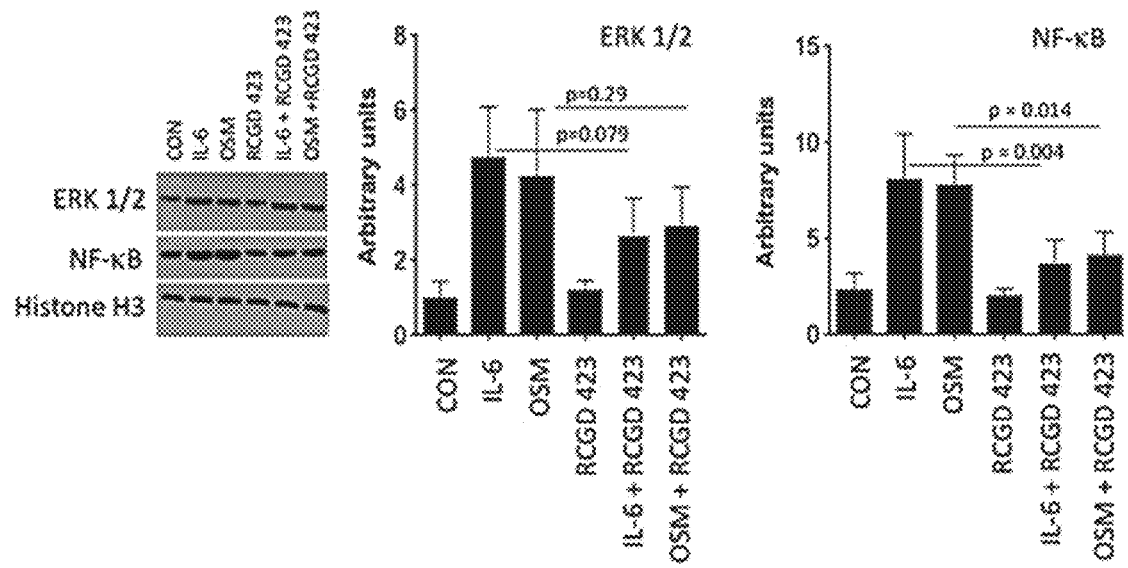

Pathogenesis of OA is a process driven by the entire joint, not just chondrocytes; both the synovium and infiltrating immune cells have been demonstrated to secrete not only IL-6, but other pro-inflammatory cytokines as well. Accordingly, the ability of RCGD 423 to suppress signaling downstream of IL-6 and OSM in synoviocytes and peripheral blood mononuclear cells was assessed (FIG. 14). These results demonstrate a potent suppression of signaling in these cell types which promote cartilage loss in injured joints, defining another potential mechanism by which RCGD 423 could interrupt the pro-degenerative cycle.

Based on these data, a small molecule modulator of gp130 signaling was identified that elicited a distinct molecular profile from IL-6 family cytokines: high levels of pSTAT3 and MYC, low induction of NF-κB and signaling through ligand-independent gp130 homodimers. Functionally, these effects result in a blockade of pro-inflammatory signaling downstream of IL-6 family cytokines, including increases in matrix-degrading enzymes; it was hypothesized that these are the cause of the anti-degenerative effects of RCGD 423 in vivo.

Figure 15A:
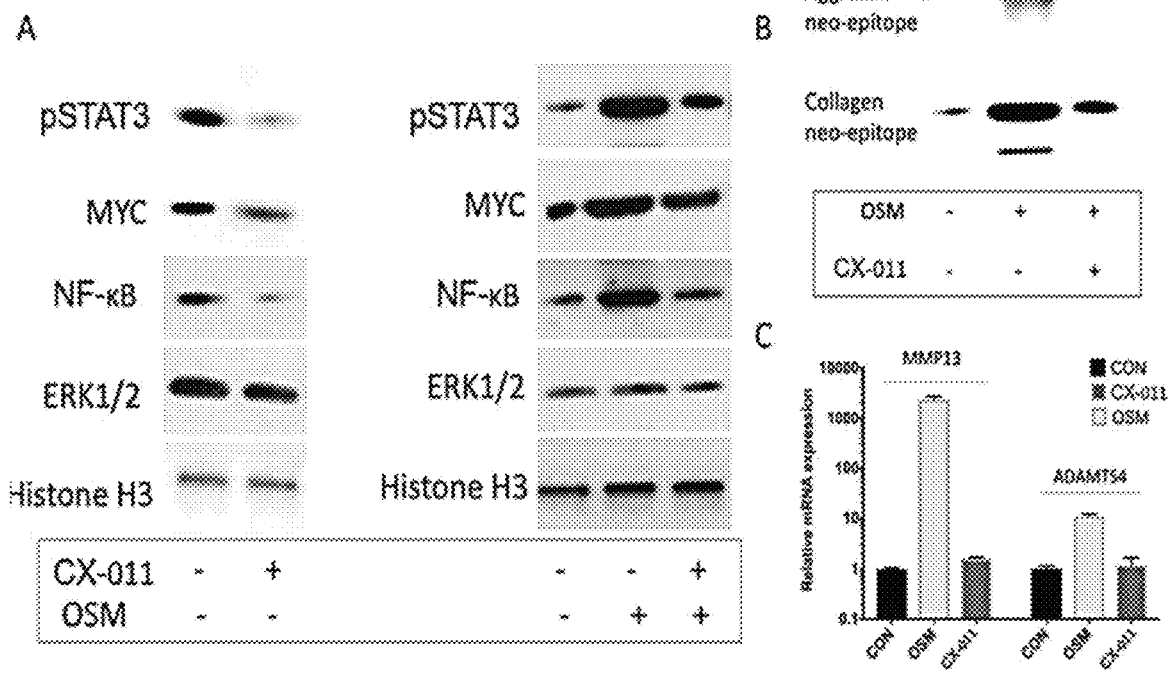
Figure 16A:
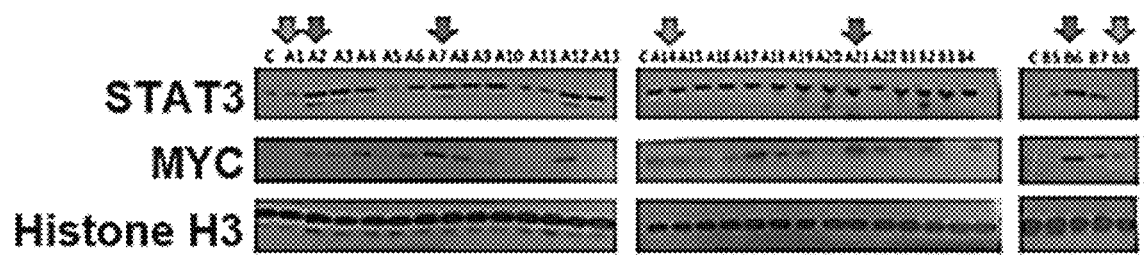
FIG. 16A-C shows Identification of novel prospective small molecule modulators of gp130 receptor. (A) Class 1 molecules (marked by red arrows) activate STAT3 and MYC signaling pathways wile Class 2 molecules (blue arrows) have no stimulatory effects on STAT3 and MYC signaling in chondrocytes as determined by western blot analysis. (B) Structures of the most prominent Class 1 and Class 2 molecules. (C) Shows additional molecules tested for effects on STAT and MYC signaling. All drugs were tested at 10 μM and assessed using Western Blot.
Figure 16B:
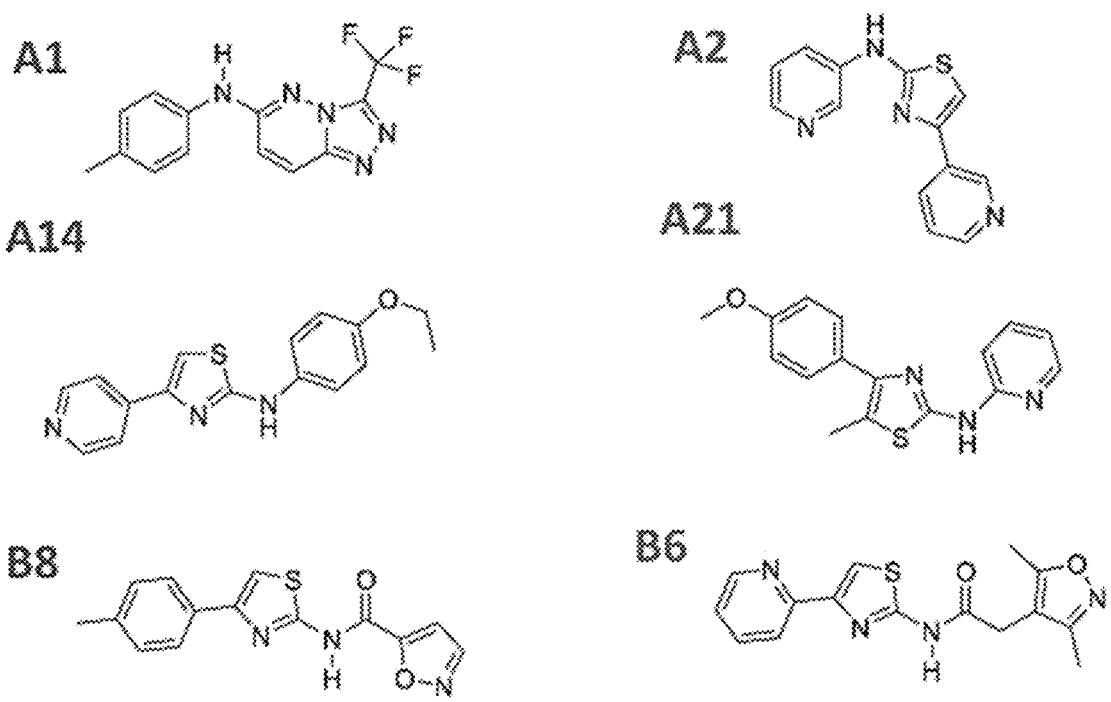
Figure 16C:
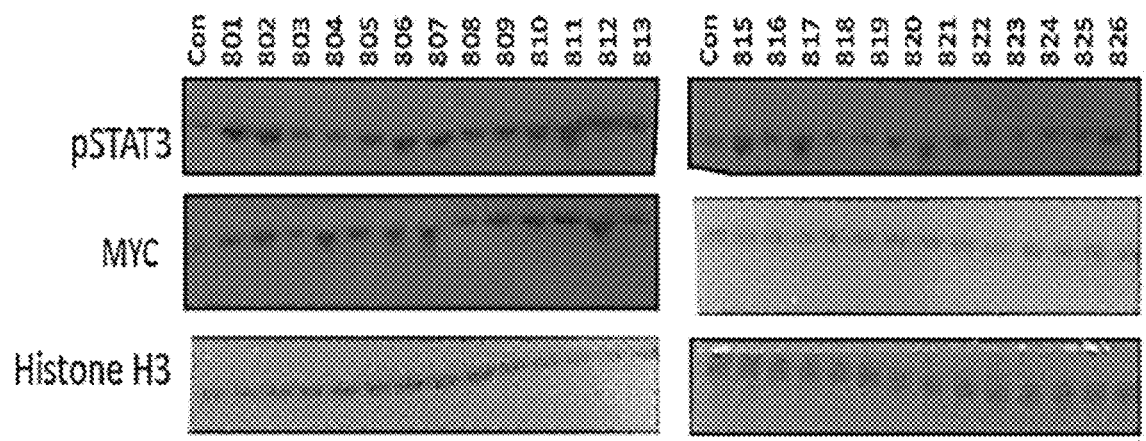
Figure 17:
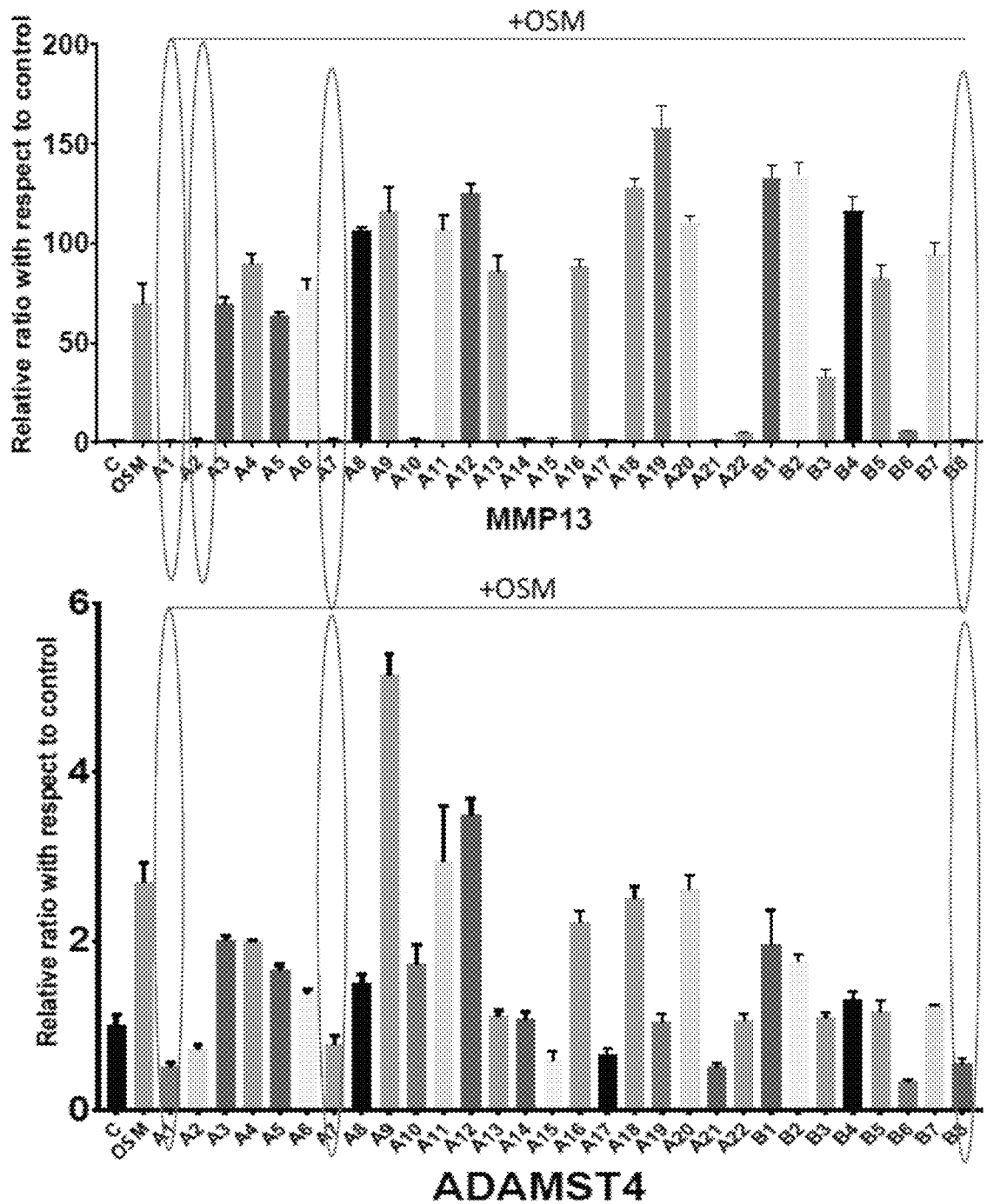
FIG. 17 shows Class 1 (red ovals) and Class 2 (blue ovals) molecules dramatically inhibit Inflammation-induced degradation of cartilage matrix proteins, as determined by measuring the levels MMP13 and ADAMTS4. Please note that pro-inflammatory cytokine oncostatin M (OSM) upregulates levels of MMP13 and ADAMTS proteases while in the presence of selected class 1 and 2 molecules this effect is mitigated.
Figure 18:
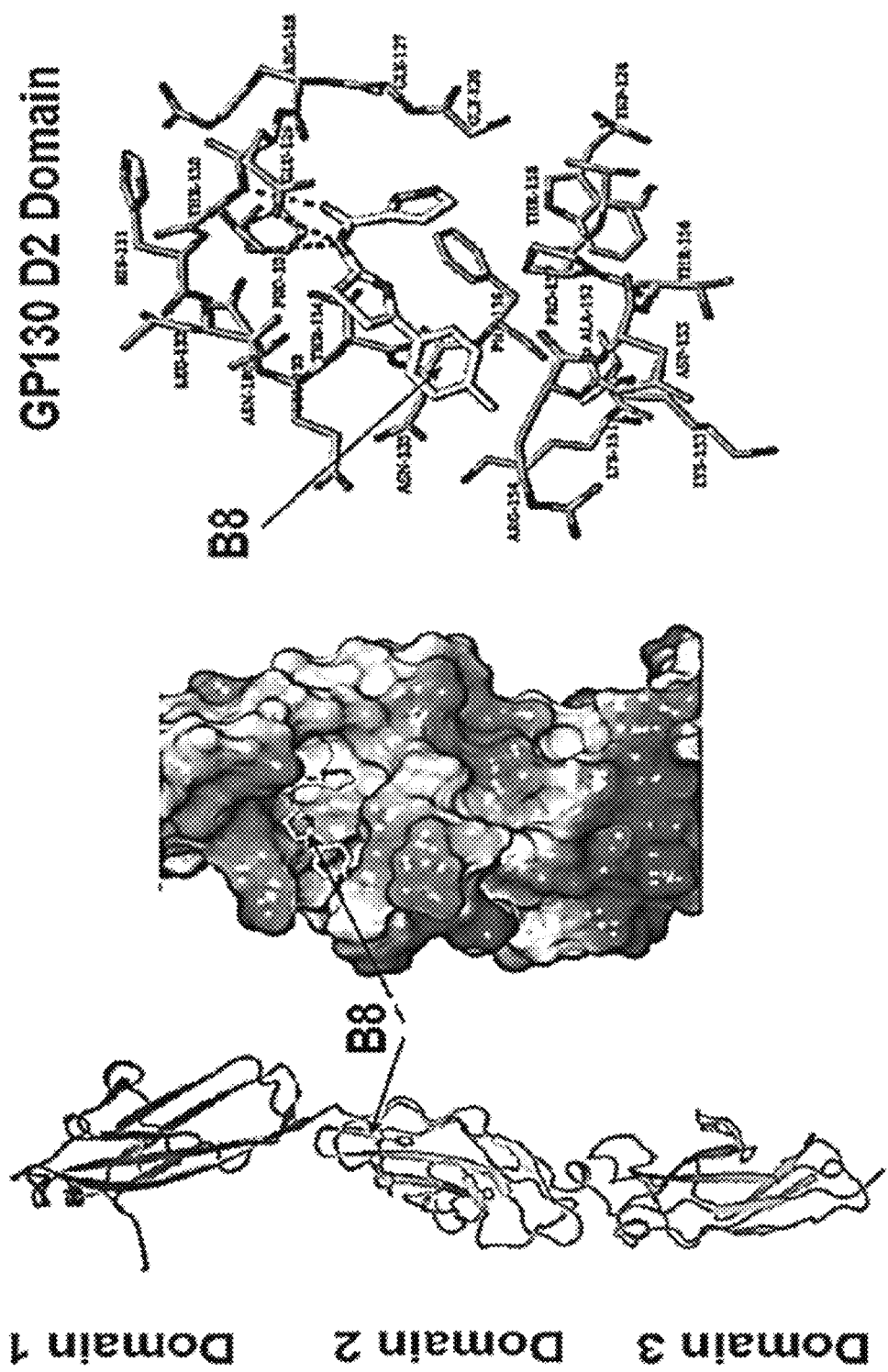
FIG. 18 shows possible binding mode for designed molecule B8 with GP130 D2 Primarily the interactions are hydrophobic in nature. The designed molecule1 is nicely fit in to the hydrophobic packet of the GP130 like RGD423. The residues interacting with the designed molecule1 are shown in stick representation. Fitness score: −1755.2 and DeltaG: −7.71 kcal/mol. SwissDoc Software.
Figure 19A:
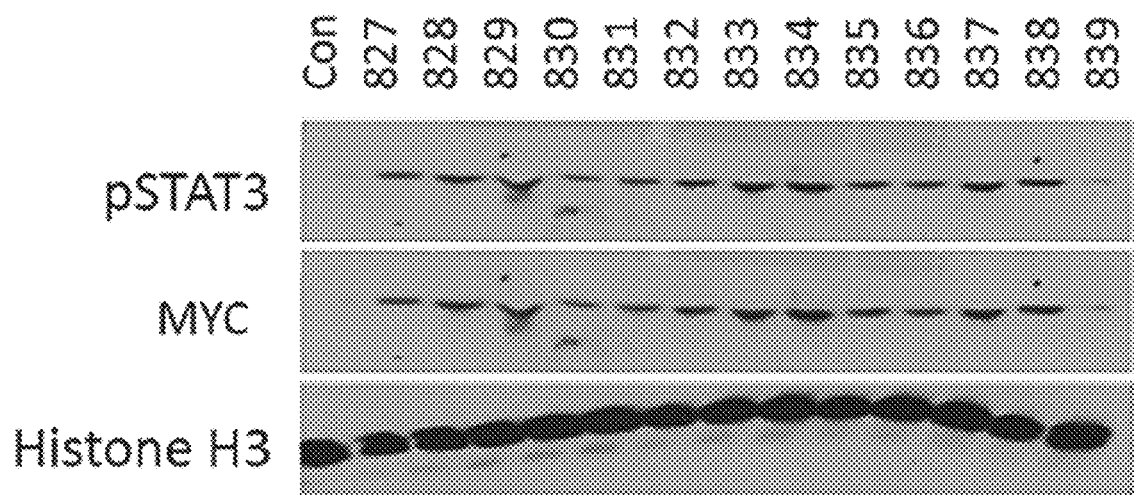
FIG. 19A-B shows that different test chemicals act as activators, neutral effectors or inhibitors for the expression of pSTAT3 and MYC in cultured porcine chondrocytes. All drugs tested at 10 μM and assessed using Western Blot.
Figure 19B:
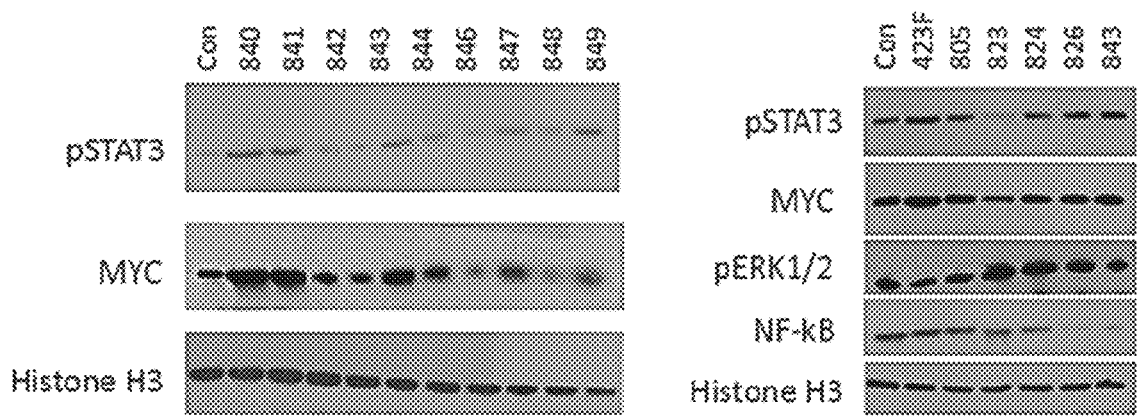
Figure 20:
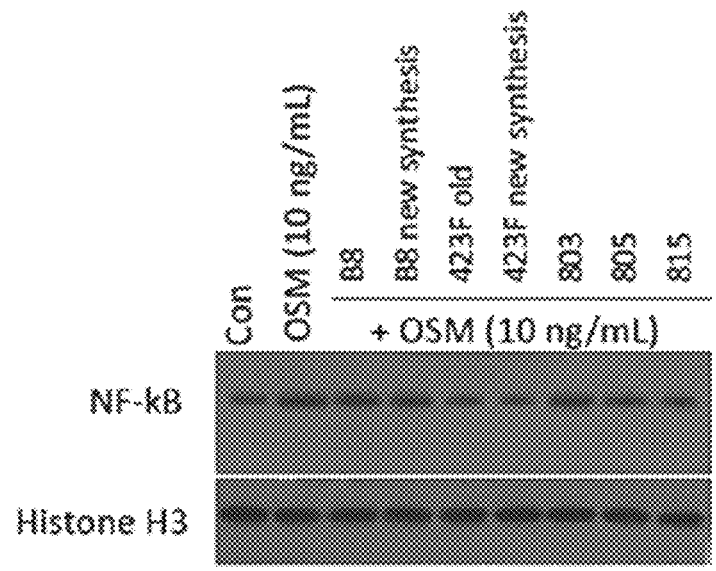
FIG. 20 shows that several analogs (e.g., B8, 803, 805 815) inhibit OSM-mediated activation of gp130. 423F is the positive control drug. Adult human articular chondrocytes from three independent donors were used to generate the results.
Figure 21:
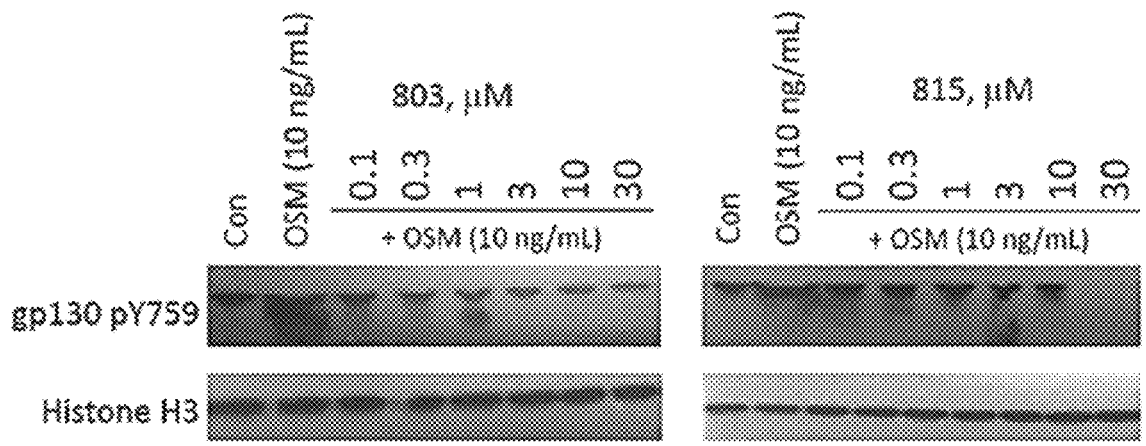
FIG. 21 shows that 803 and 815 inhibit OSM-mediate d activation of gp130. Adult human articular chondrocytes from three independent donors were used to generate the results.
Figure 22A:
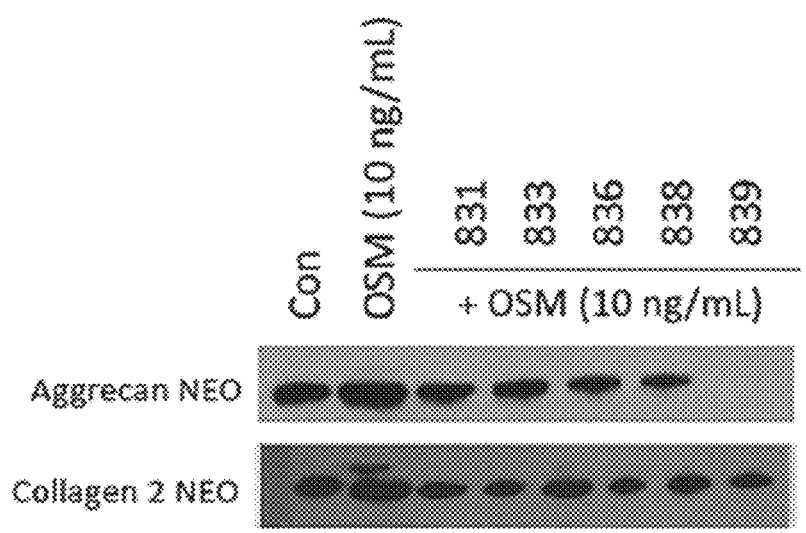
FIG. 22A-C show matrix degradation assays. Several analogs (e.g., 805, 839) strongly prevent the breakdown of collagen and aggrecan in pig articular cartilage explants driven by OSM as indicated by lower levels of degeneration epitopes for aggrecan (aggrecan-neo) and collegen 2 (collagen-neo).
Figure 22B:
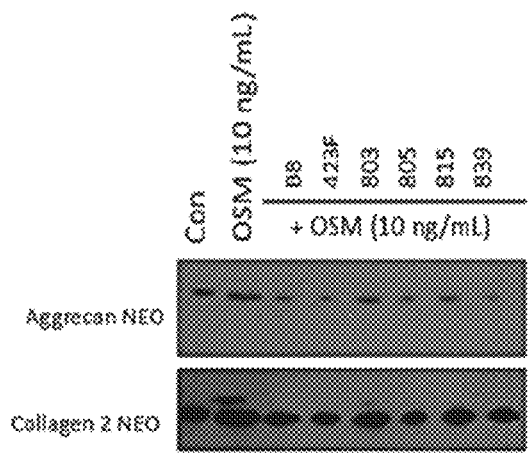
Figure 22C:
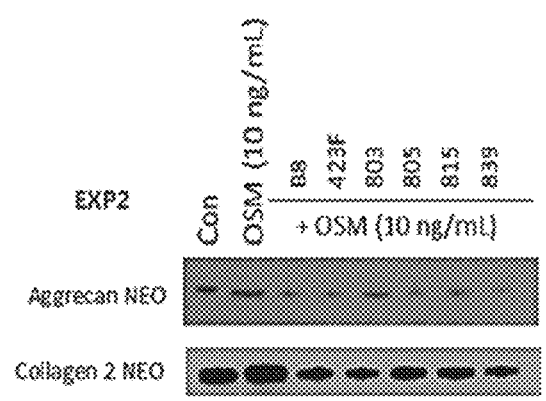
Figure 23:
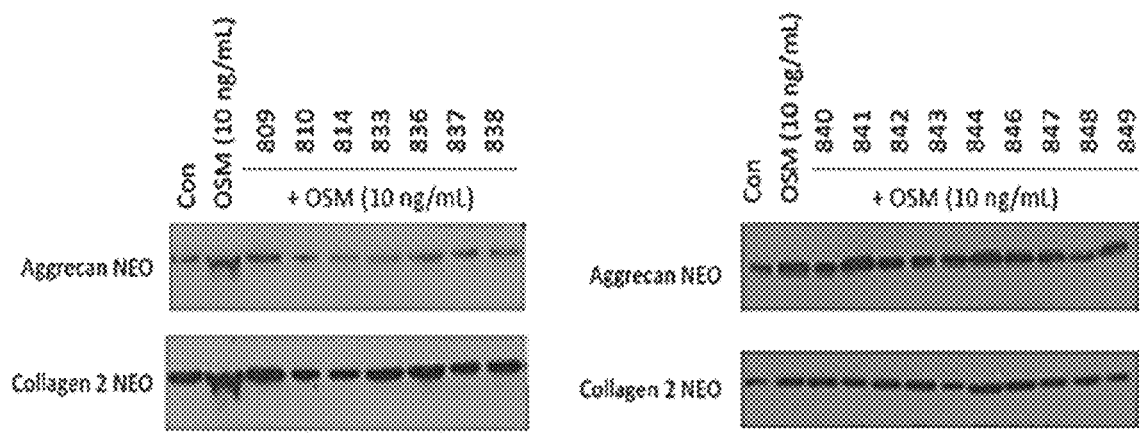
FIG. 23 shows that some pSTAT3 and MYC activating analogs (e.g., 810, 840) can also strongly prevent the breakdown of collagent and aggrecan in pig articular cartilage explants driven by OSM as indicated by lower levels of degeneration epitopes for aggrecan (aggrecan-neo) and collagen 2 (collagen-neo).
Figure 24:
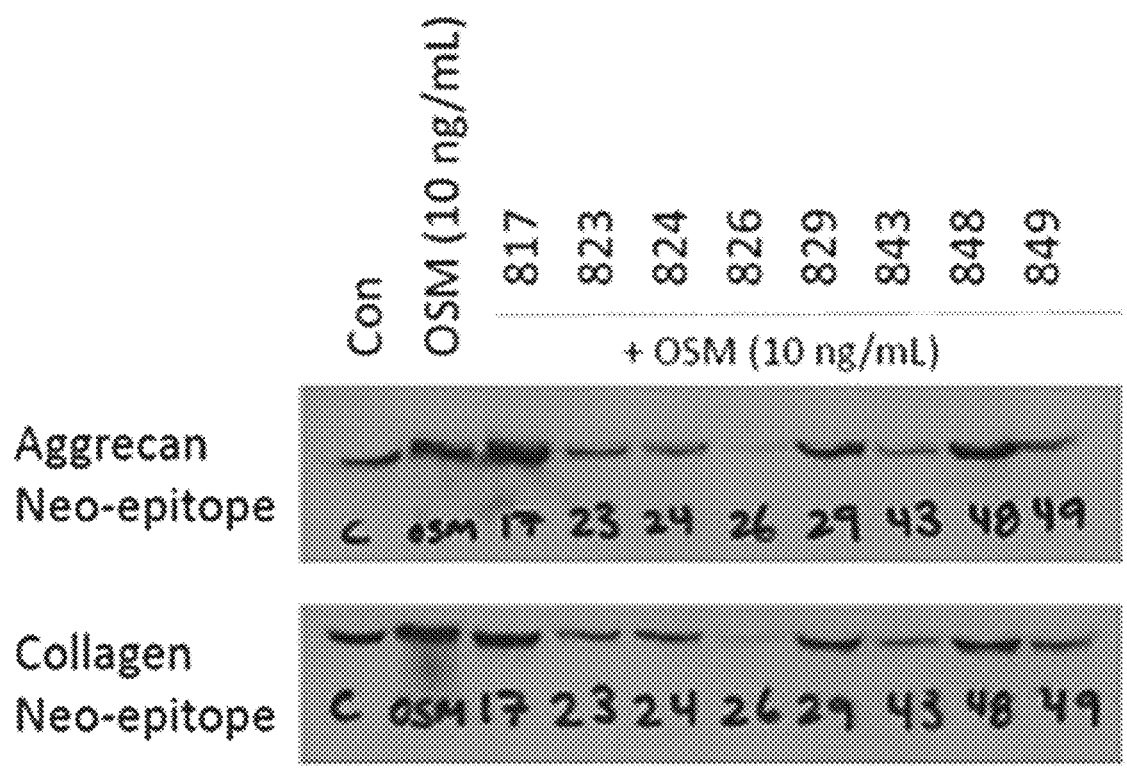
FIG. 24 shows that some analogs (e.g., 826, 843, 849) can still strongly prevent the breakdown of collagen and aggrecan in pig articular cartilage explants driven by OSM as indicated by lower levels of degeneration epitopes for aggrecan (aggrecan-neo) and collagen 2 (collagen-neo).
Figures 28A, 28B, 28C:
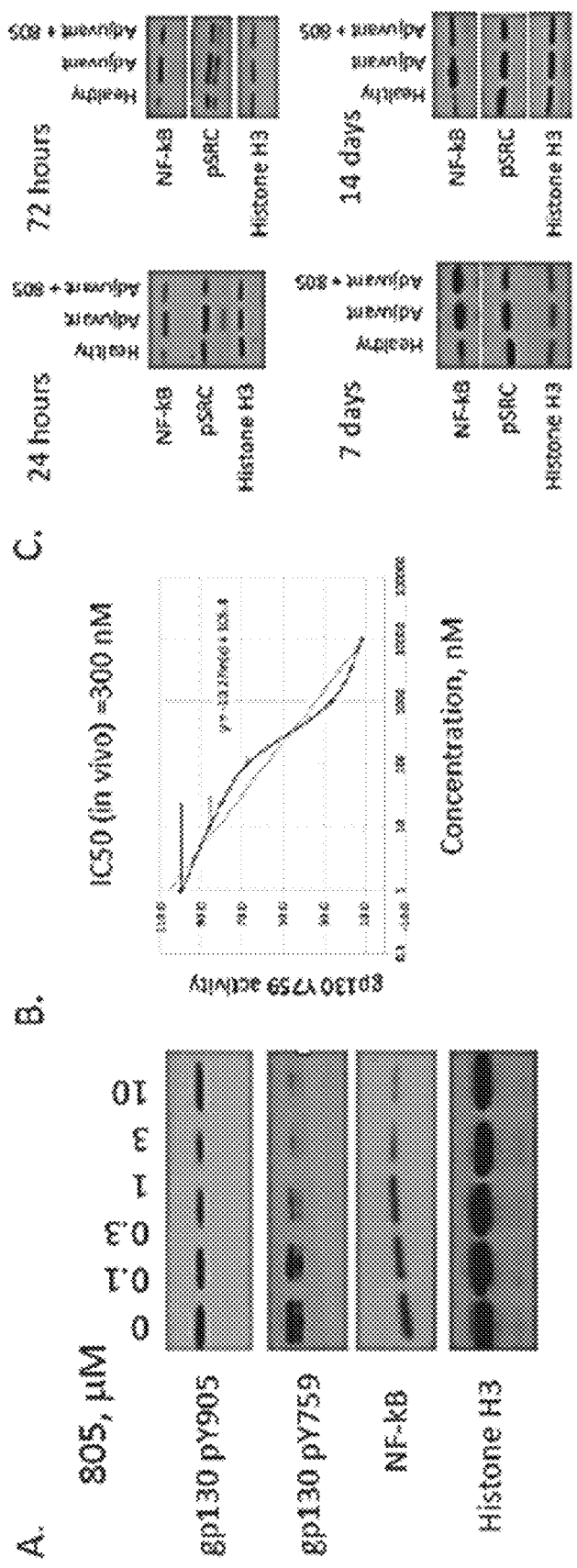
FIG. 28A-C shows 805 inhibits inflammatory response in vivo in a dose-dependent manner. Rat (Sprague-Dawley wild-type) were injected with Complete Freund's Adjuvant (CFA) to induce systemic inflammatory response. Drug (805) was injected intra-articularly; multiple doses (A and B, N=3). 805 showed prolonged effect preventing activation gp130 in sick animals as well as leading to lower activity of inflammatory indicators such as NF-kB and pSRC kinase.
Figure 29:
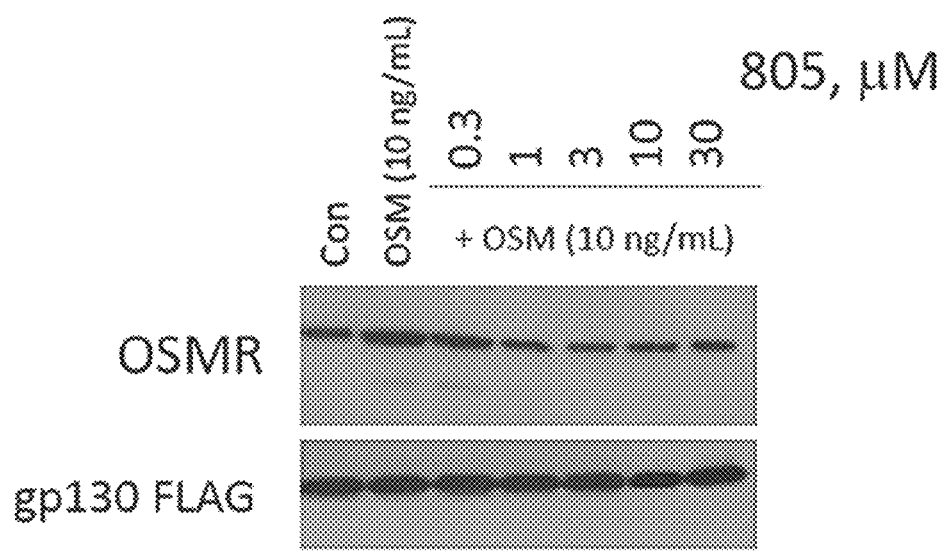
FIG. 29 shows a receptor competition assay. Adult human chondrocytes; IP-FLAG AB (transfected with gp130 FLAG plasmid), WB-OSMR. This assay shows that 805 disrupts the interaction between OSMR and gp130 in a concentration-dependent manner.
Figure 30:
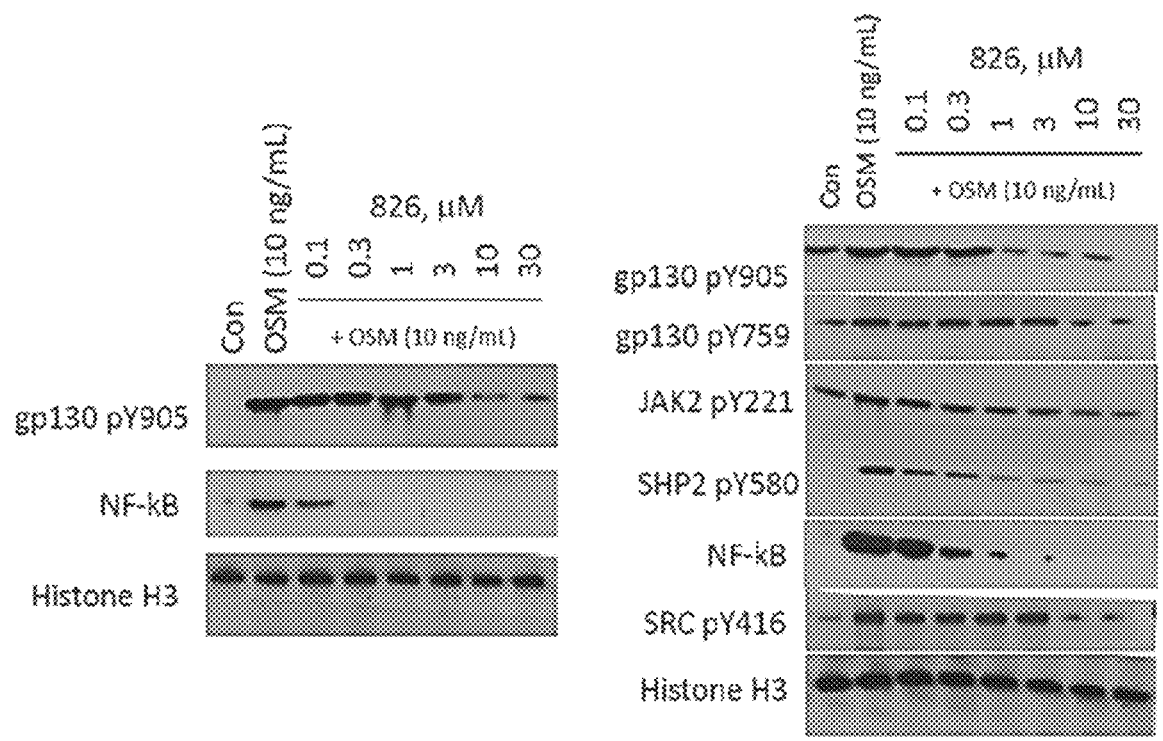
FIG. 30 shows that molecule 826 strongly inhibits OSM-mediated activation of gp130 and downstream effectors of chronic inflammation including JAK2, SHP2, NF-kB, and SRC. Adult human articular chondrocytes from three independent donors were used.
Figure 31:
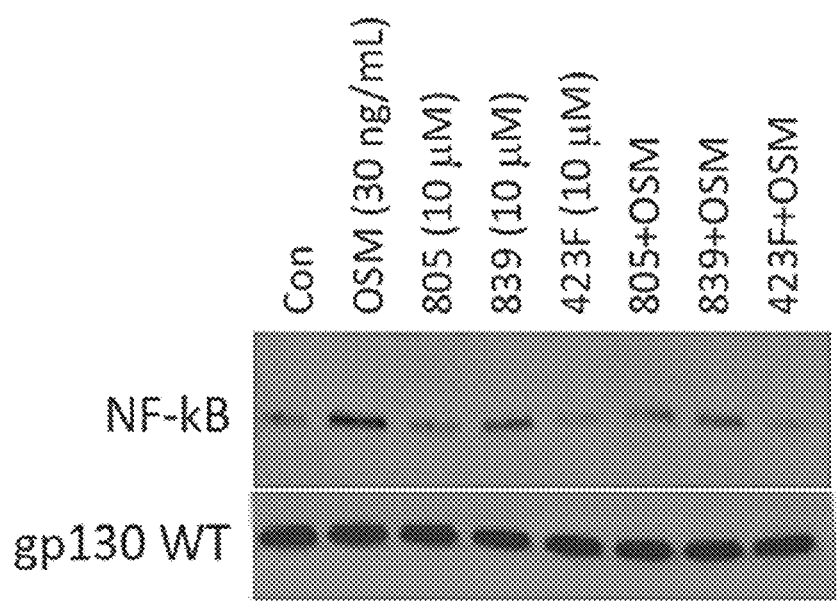
FIG. 31 shows molecules of the disclosure inhibit OSM-induced NF-kB activation in BaF3 via transgenic gp130. BaF3 cells were transfected with WT gp130 plasmid.
Figure 32:
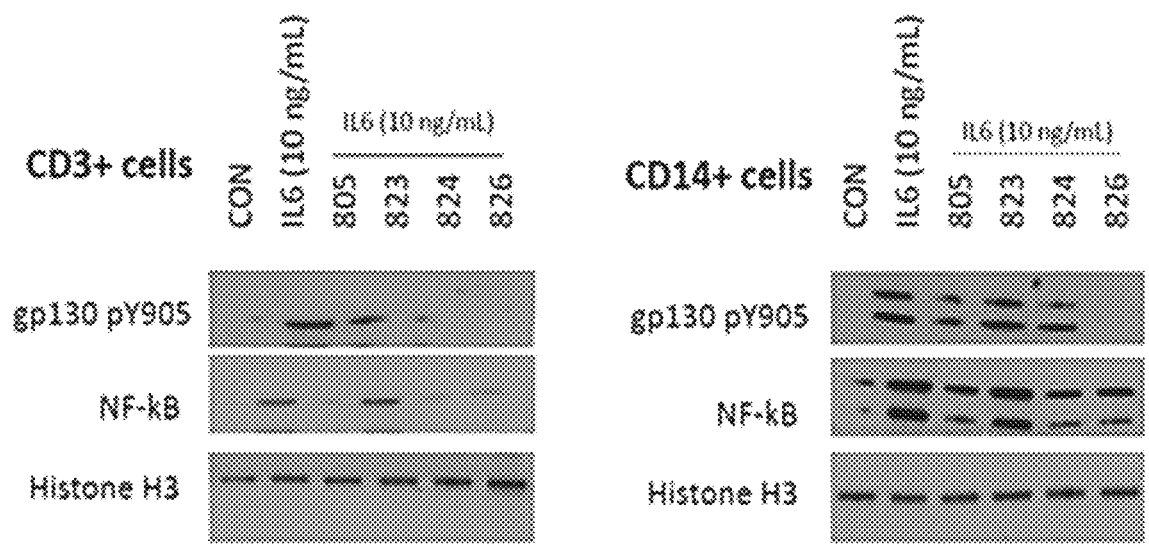
FIG. 32 shows molecules 805 and 826 strongly inhibit OSM-mediated activation of gp130 and downstream effectors of chronic inflammation including NF-kB in human immune cells. Cells from three independent donors were used to generate the results.
Figure 35:
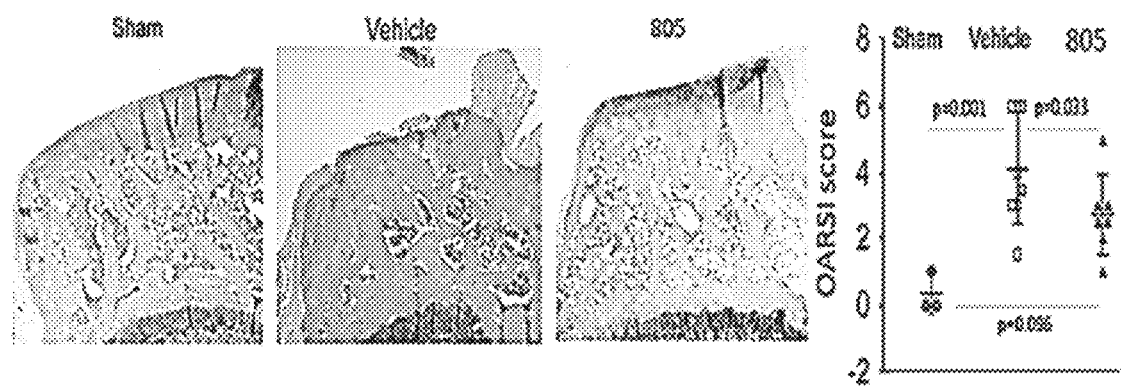
FIG. 35 shows that intra-articular injection of molecule 805 reduces cartilage degeneration following medial meniscal tear surgery.
Figure 36:
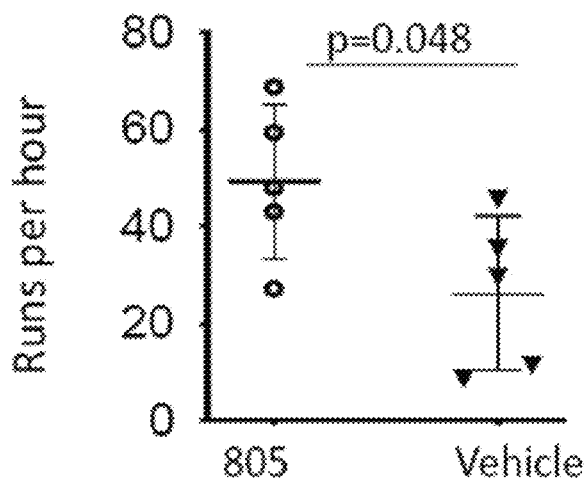
FIG. 36 shows a graph of pain assessment (spontaneous activity) in CFA-induced arthritis. Number of runs per hour was determined using a well-accepted activity wheel system installed in housing cages and equipped with an automatic counter. Control rats were treated with vehicle, molecule 805 was injected systemically (10 mg/kg) for 15 days.
Figure 37:
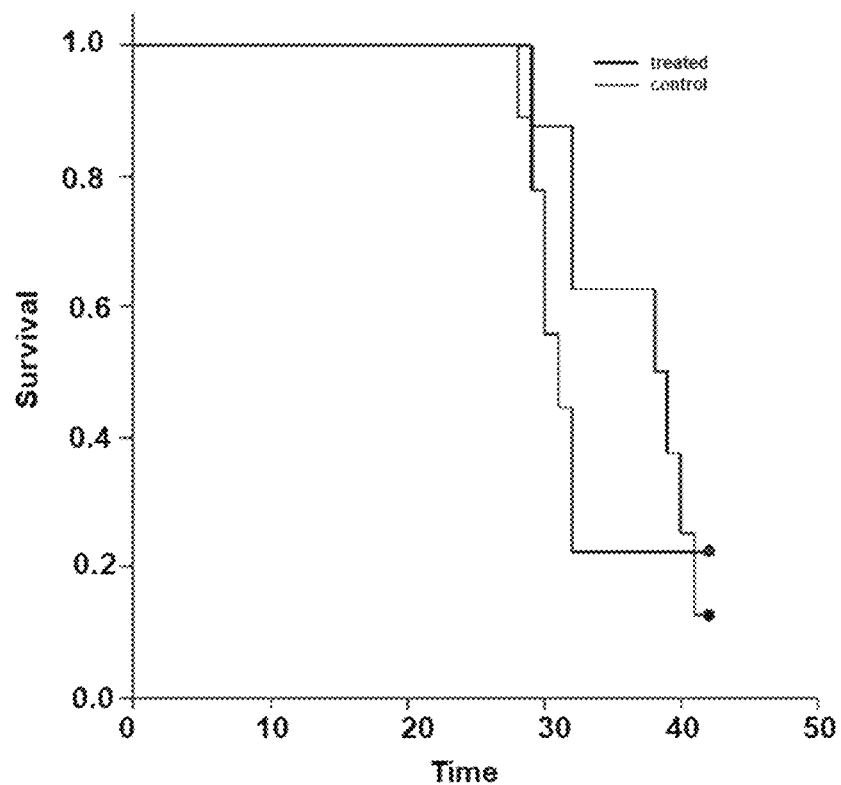
FIG. 37 shows survival analysis of NZM.2328 female mice, which spontaneously developed a lethal lupus nephritis-like syndrome with 90% penetrance survive longer when injected intraperitoneally twice weekly with 10 mg/kg of molecule 805.
Figure 38:
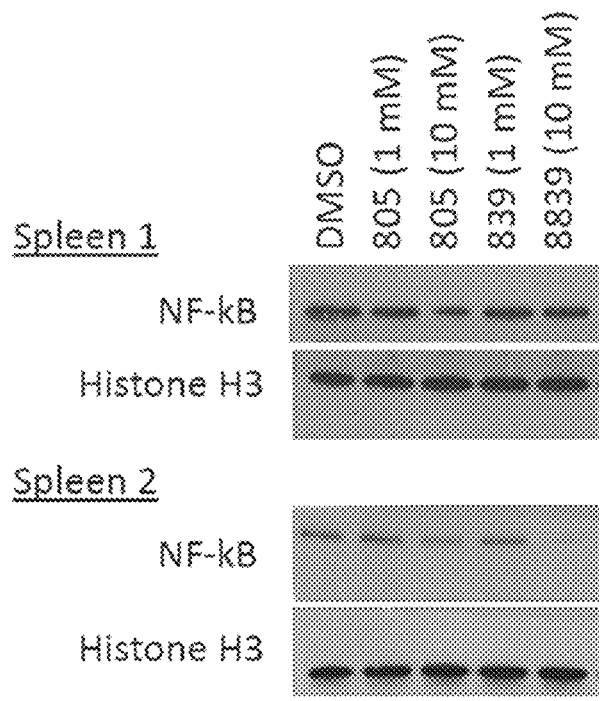
FIG. 38 are blots from NZM.2328 mice that spontaneously developed severe immune inflammatory disease similar to human lupus. Incubation of spleen cells obtained from these mice with molecules 805 and 839 results in significant reduction of inflammatory activity (marked with NF-kB) in these cells compared to control cells treated with DMSO.

Based on these data, derivatives of RCGD 423 were developed for several reasons. Firstly, RCGD 423 was a hit from a library; this made the depth of the discovery surrounding the technology less comprehensive. Additionally, the physical properties of RCGD 423 (solubility, potency, functional groups) could be improved. Significant gains in these areas could potentially result in a first-in-class injectable for the treatment of post-traumatic OA. Moreover, the potential risks associated with promoting MYC stabilization and proliferation in gp130+ cells as well as large increases in active STAT3 protein was of concern. Therefore, a cohort of structural variants based on the RCGD 423 scaffold were generated that were predicted to bind in the same pocket of gp130 and possess improved physical properties. These compounds were then screened in adult pig articular chondrocytes and cartilage explants, seeking compounds that could inhibit the catabolic effects of OSM but not drive increases in MYC and pSTAT3 protein levels. One analog, CX-011 (B8), stood out as it almost completely blocked the generation of aggrecan and collagen neoepitopes, indicative of strong anti-catabolic potential, and did not increase levels of pSTAT3 and MYC (FIGS. 15A and B). Moreover, CX-011 (B8) reduced the induction of proteolytic gene expression, further supporting the neoepitope data (FIG. 15C). Importantly, unlike some other analogs tested, CX-011 (B8) did not strongly effect basal levels of MYC and pSTAT3 proteins, which may play important roles in maintaining chondrocyte homeostasis (FIG. 15A). The interaction between CX-011 (B8) and gp130 was modeled, which suggested and strong binding of the compound to the same binding site occupied by RCGD 423. Together, these preliminary data identify CX-011 (B8) as a highly anti-inflammatory, anti-catabolic alternative to RCGD 423, with increased "drug-like" properties and reduced potential molecular liabilities.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating osteoarthritis comprising contacting a human subject in need thereof with a therapeutically effective amount of a pharmaceutical composition comprising a suspension of compound 805 in a pharmaceutically acceptable carrier formulated for injection:

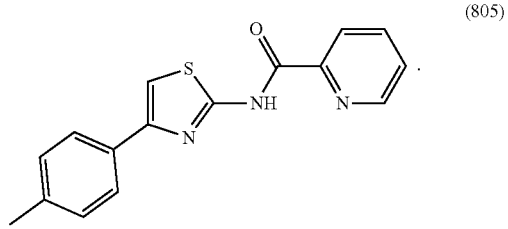 [SMILES: Cc1ccc(-c2csc(NC(=O)c3ccccn3)n2)cc1]

(805)

2. The method of claim 1, wherein the pharmaceutical composition further comprises hyaluronic acid.

3. The method of claim 1, further comprising contacting the subject with an additional therapeutic compound selected from the group consisting of glucocorticoid treatments, steroidals, local or general anesthetics, NSAIDS, low molecular weight heparins, anti-inflammatories, anti-TNF antibodies and soluble TNF receptors and cyclooxygenase-2 inhibitors.

4. The method of claim 1, wherein the composition is effective to treat osteoarthritis at less than about 10 mg/kg of body weight.

5. The method of claim 1, wherein the composition is sterilized by filtration.

6. The method of claim 1, wherein the pharmaceutical composition is formulated for injection into the knee or hip.

7. The method of claim 1, wherein the osteoarthritis affects the synovium by promoting infiltration and activation of immune cells.

* * * * *